US010456386B2

(12) United States Patent
Wraight et al.

(10) Patent No.: US 10,456,386 B2
(45) Date of Patent: Oct. 29, 2019

(54) PHARMACEUTICAL COMPOSITION COMPRISING BETAHISTINE

(71) Applicant: Otolanum AG, Zug (CH)

(72) Inventors: Christopher John Wraight, Blackburn (AU); Thomas Meyer, Zuchwil (CH)

(73) Assignee: OTOLANUM AG, Zug (CH)

( * ) Notice: Subject to any disclaimer, the term of this patent is extended or adjusted under 35 U.S.C. 154(b) by 0 days.

(21) Appl. No.: 15/887,388

(22) Filed: Feb. 2, 2018

(65) Prior Publication Data
US 2018/0214432 A1 Aug. 2, 2018

Related U.S. Application Data

(60) Provisional application No. 62/453,931, filed on Feb. 2, 2017.

(51) Int. Cl.
| | |
|---|---|
| *A61K 31/4402* | (2006.01) |
| *A61K 45/06* | (2006.01) |
| *A61K 47/10* | (2017.01) |
| *A61K 47/26* | (2006.01) |
| *A61K 47/32* | (2006.01) |
| *A61K 47/38* | (2006.01) |
| *A61K 9/00* | (2006.01) |
| *A61P 27/16* | (2006.01) |

(52) U.S. Cl.
CPC ........ *A61K 31/4402* (2013.01); *A61K 9/0043* (2013.01); *A61K 9/0073* (2013.01); *A61K 45/06* (2013.01); *A61K 47/10* (2013.01); *A61K 47/26* (2013.01); *A61K 47/32* (2013.01); *A61K 47/38* (2013.01); *A61P 27/16* (2018.01)

(58) Field of Classification Search
None
See application file for complete search history.

(56) References Cited

U.S. PATENT DOCUMENTS

| | | | |
|---|---|---|---|
| 4,229,428 A | 10/1980 | Cherqui et al. | |
| 5,897,858 A * | 4/1999 | Haslwanter | A61K 9/0043 |
| | | | 424/434 |
| 7,090,830 B2 | 8/2006 | Hale et al. | |
| 7,728,015 B2 * | 6/2010 | Barak | A61K 31/19 |
| | | | 514/357 |
| 7,737,165 B2 | 6/2010 | Barak | |
| 8,119,668 B2 | 2/2012 | Nelson et al. | |
| 8,242,148 B2 * | 8/2012 | Nelson | A61K 31/4402 |
| | | | 514/357 |
| 8,642,631 B2 * | 2/2014 | Anderson | A61K 31/4402 |
| | | | 514/357 |
| 2003/0001711 A1 | 1/2003 | Rabinowitz et al. | |
| 2006/0246012 A1 | 11/2006 | Rabinowitz et al. | |
| 2008/0066741 A1 | 3/2008 | LeMahieu et al. | |

FOREIGN PATENT DOCUMENTS

| | | | |
|---|---|---|---|
| EP | 0397025 | * | 11/1990 |
| EP | 0397025 A1 | | 11/1990 |
| WO | WO 2009/143572 A1 | | 12/2009 |

OTHER PUBLICATIONS

Bhise et al. in Asian Journal of Pharmaceutics 201-215 (2008) (Year: 2008).*
Marx et al. in Intranasal Drug Administration—An Attractive Delivery Route for Some Drugs (Chapter 13), Drug Discovery and Development—From Molecules to Medicine, pp. 299-320 (2015) (Year: 2015).*
Kovanaze (www.rxlist.com/kovanaze-drug.htm#description (retrieved from the internet Mar. 19, 2019) (Year: 2016).*
Tetracaine Hydrochloride at https://www.sigmaaldrich.com/content/dam/sigma-aldrich/docs/Sigma-Aldrich/Product_Information_Sheet/t7645pis.pdf (retrieved from the internet Mar. 19, 2019) (Year: 2019).*
Oxymetazolone Hydrochloride https://www.caymanchem.com/pdfs/23826.pdf (retrieved from the internet Mar. 19, 2019) (Year: 2019).*
Kovacaine at https://clinicaltrials.gov/ct2/show/study/NCT01302483) (retrieved from the internet Mar. 19, 2019) (Year: 2015).*
Shelton et al., "Histamine Receptors in the Human Nose," Clin. Otolaryngol., 1994, 19, 45-49 (Year: 1994).*
Gananca et al. in Braz J Otorhinolaryngol 77(4):499-503 (2011) (Abstract) (Year: 2011).*
Moorthy, G. et al. in Biopharm Drug Dispos. 36(7):429-439 (2015) (Year: 2015).*
Pathy et al. in Age Ageing. 6(3): 179-184 (1977) (Abstract) (Year: 1977).*
Adrion et al. BMJ 352:h6816, 1-16 (2016) (Year: 2016).*
Adrion, et al., "Efficacy and safety of betahistine treatment in patients with Meniere's disease: primary results of a long term, multicentre, double blind, randomised, placebo controlled, dose defining trial (BEMED trial)." BMJ (2016); 352: h6816, pp. 1-16.
Anderson, et al., "Effects of Betahistine HCl, Nicotinic Acid, and Histamine on Basilar Blood Flow in Anesthetized Dogs." Stroke (1971); 2: 409-415.
Barak, "Betahistine: what's new on the agenda?" Expert Opin. Lnvestig. Drugs (2008); 17 (5): 795-804.
Barak, et al., "A Randomized, Double-Blind, Placebo-Controlled Pilot Study of Betahistine to Counteract Olanzapine-Associated Weight Gain." Journal of Clinical Psychopharmacology (2016); 36 (3): 253-256.
Barak, et al., "Betahistine decreases olanzapine-induced weight gain and somnolence in humans." Journal of Psychopharmacology (2016); 30(3): 237-241.
Benecke, et al., "Effects of Betahistine on Patient-Reported Outcomes in Routine Practice in Patients with Vestibular Vertigo and Appraisal of Tolerability: Experience in the OSVaLD Study." International Tinnitus Journal (2010); 16 (1): 14-24.
Bertlich et al., "Histaminergic $H_3$-Heteroreceptors as a Potential Mediator of Betahistine-Induced Increase in Cochlear Blood Flow." Audiology & Neorology (2015); 20: 283-293.

(Continued)

*Primary Examiner* — Dennis Heyer
(74) *Attorney, Agent, or Firm* — Cooley LLP

(57) ABSTRACT

The present disclosure relates to a pharmaceutical composition comprising as active substance betahistine or a pharmaceutically acceptable salt thereof, for use in the treatment of otological or neurological disorders in a human subject by intranasal application.

20 Claims, 10 Drawing Sheets

(56) References Cited

OTHER PUBLICATIONS

Bertlich, et al., "Betahistine metabolites, Aminoethylpyridine, and Hydroxyethylpyridine increase cochlear blood flow in guinea pigs in vivo." International Journal of Audiology (2014); 53: 753-759.

Bowman, et al., "Possible Alternate Routes in the Metabolism of Betahistine in the Rannit." Proceedings of the Society for Experimental Biology and Medicine (May-Sep. 1972); 140: 1385-1388, 5 pages.

Burton MJ, J.A., "Betahistine for Ménière's disease or syndrome." Cochrane Database of Systematic Reviews (2001); Issue 1, Art. No. CD001873, 32 pages.

Chen, et al., "LC-MS-MS analysis of 2-pyridylacetic acid, a major metabolite of betahistine: application to a pharmacokinetic study in healthy volunteers." Xenobiotica (2003); 33(12): 1261-1271.

Dziadziola, et al., "Betahistine increases vestibular blood flow." Otolaryngology Head and Neck Surgery (1999); 120: 400-405.

El Nabarawi, et al., "Formulation and Evaluation of Betahistine Dihydrochloride Mucoadhesive Nasal Gels." 2014 AAPS Annual Meeting, Abstract R6044, 1 page. abstracts.aaps.org/Verify/AAPS2014/PosterSubmissions/R6044.pdf.

El Nabarawi, et al., "Transbuccal delivery of betahistine dihydrochloride from mucoadhesive tablets with a unidirectional drug flow: in vitro, ex vivo and in vivo evaluation." Drug Design, Development and Therapy (2016); 10: 4031-4045.

Estrada-Marín, et al., "Bioequivalence of Two Oral Tablet Formulations of Betahistine 24 Mg: Single-Dose, Open-Label, Randomized, Two-Period Crossover Comparison in Healthy Individuals." J Bioequiv Availab (2015); 7 (1): 001-004.

Guth, Paul S., "The pharmacology of betahistine in the context of the vestibular system." Acta Otorhinolaryngol Ital. (2001); 21(3 Suppl 66): 16-23.

Ihler, et al., "Betahistine Exerts a Dose-Dependent Effect on Cochlear Stria Vascularis Blood Flow in Guinea Pigs In Vivo." PLoS ONE (2012); 7(6): e39086, pp. 1-6.

International Search Report and Written Opinion for International Application No. PCT/EP2018/052695, dated Mar. 22, 2018, 14 pages.

Jeck-Theole and Wagner, "Betahistine A Retrospective Synopsis of Safety Data." Drug Safety (2006); 29 (11): 1049-1059.

Karapolat, et al., "Does betahistine treatment have additional benefits to vestibular rehabilitation?" Eur Arch Otorhinolaryogol (2010); 267: 1207-1212.

Lezius, et al., "High-dosage betahistine dihydrochloride between 288 and 480 mg/day in patients with severe Menie`re's disease: a case series." Eur Arch Otorhinolaryngol (2011); 268: 1237-1240.

Moorthy, et al., "Safety, tolerability and pharmacokinetics of 2-pyridylacetic acid, a major metabolite of betahistine, in a phase 1 dose escalation study in subjects with ADHD." Biopharmaceutics & Drug Disposition (2015); 36(7): 429-439.

Murdin, et al., "Betahistine for symptoms of vertigo." Cochrane Database of Systematic Reviews (2016); Issue 6. Art. No. CD010696, 63 pages.

Parfenov, et al., "Effectiveness of betahistine (48 mg/day) in patients with vestibular vertigo during routine practice: The VIRTUOSO study." PLoS ONE (2017); 12 (3): e0174114.

Pilicheva, et al., "Development and in vitro evaluation of mucoadhesive microsphere carriers for intranasal delivery of betahistine dihydrochloride." International Journal of Drug Delivery (2013); 5(4): 389-401.

Pilicheva, et al., "Investigation of betahistine dihydrochloride biocompatibility and nasal permeability in vitro." Journal of Applied Medicine (2016); 14(4): 299-305.

Provensi, et al., "The histaminergic system as a target for the prevention of obesity and metabolic syndrome." Neuropharmacology (2015); 106: 3-12. doi: 10.1016/j.neuropharm.2015.07.002.

Redon, et al., "Betahistine Treatment Improves the Recovery of Static Symptoms in Patients With Unilateral Vestibular Loss." Journal of Clinical Pharmacology (2011); 51: 538-548.

Strupp, et al., "Pharmacotherapy of vestibular and ocular motor disorders, including nystagmus." Journal of Neurology (2011); 258: 1207-1222.

Tighilet, et al., "Betahistine Dihydrochloride Treatment Facilitates Vestibular Compensation in the Cat." Journal of Vestibular Research (1995); 5(1): 53-66.

Tighilet, et al., "Dose- and duration-dependent effects of betahistine dihydrochloride treatment on histamine turnover in the cat." European Journal of Pharmacology (2005); 523: 54-63.

\* cited by examiner

PHARMACEUTICAL COMPOSITION COMPRISING BETAHISTINE

CROSS REFERENCE TO RELATED APPLICATIONS

The present application claims the benefit of priority to U.S. Provisional Application No. 62/453,931 filed on Feb. 2, 2017, the contents of which are hereby incorporated by reference in their entirety.

FIELD

The present disclosure generally relates to pharmaceutical compositions comprising betahistine or a pharmaceutically acceptable salt thereof, and methods of use thereof, for example, in the treatment of otological or neurological disorders.

BACKGROUND

Medicinal agents useful in the treatment of vestibular disorders or relieving symptoms of vestibular disorders, such as histamine, are known to act via the histaminergic system. Histamine is a potent bioactive substance that has been studied for nearly a century, acting as an aminergic neurotransmitter in the nervous system and as a local mediator in the gut, skin, and immune system peripherally and in the brain. Betahistine is a structural analog of histamine with similar pharmacologic properties, but without potentially severe side effects of histamine such as anaphylactic reactions.

Betahistine is known to have therapeutic benefits in the treatment of vestibular vertigo, e.g. in benign paroxysmal positional vertigo, vestibular neuritis, or Meniere's disease. The therapeutic effects of betahistine in Meniere's disease, a condition characterized by vertigo, tinnitus, hearing loss and the sensation of pressure or pain in the affected ear, have been evaluated in a large number of clinical trials. However, the results of the trials are controversial and the general opinion of the reviewers is that there is still insufficient evidence to say whether betahistine has any effect on Meniere's disease or not. Betahistine is also known to have therapeutic benefits in vestibular rehabilitation, e.g., significantly shortened time to recovery for postural stability and subjective visual vertical and head orientation in Meniere's patients following vestibular neurectomy.

Betahistine is also known to have therapeutic effects in the treatment of neurological disorders such as obesity, attention deficit hyperactivity disorder, cerebrovascular disease/dementia, narcolepsy/sleep disorders, Parkinson, addiction, schizophrenia, Gilles de la Tourette syndrome, or Alzheimer's disease.

In humans, betahistine is usually administered orally in the form of tablets or a solution, usually two to three times daily, up to 6 times a day. Betahistine is known for its short plasma half-life (3-4 h) which necessitates frequent administration and may lead to noncompliance, especially in elderly patients. In addition, after oral administration, betahistine is readily and almost completely absorbed from all parts of the gastro-intestinal tract. Following absorption, the drug is rapidly and almost completely metabolized into 2-pyridylacetic acid (2-PAA; which has no pharmacological activity) by monoamine oxidase. Due to its very high first pass metabolism, the absolute bioavailability of orally administered betahistine is estimated to be around 1% (SmPC). Accordingly, plasma levels of betahistine are very low.

Thus, the strong first-past effect following oral administration of betahistine limits the compound's efficacy in clinical practice, and substantially higher doses may indeed be necessary in order to achieve more pronounced results. Therefore, there is a need to provide improved pharmaceutical compositions comprising betahistine, and methods of administration thereof for the treatment of otological or neurological disorders, including inner ear dysfunctions, which provides increased efficacy and allows for a reduced frequency and/or daily dosage, as well as to attain a more rapid and prolonged effect.

SUMMARY OF THE DISCLOSURE

In various embodiments, the present disclosure is directed to pharmaceutical compositions for intranasal delivery to a human patient, comprising a solution or suspension of therapeutically effective amount of betahistine or a pharmaceutically acceptable salt thereof and a viscosity enhancing agent.

In particular embodiments, the present disclosure is directed to pharmaceutical compositions as described herein, wherein after a single intranasal administration to a human, the $C_{max}$ ranges from 80-125% of: about 640 pg/mL for a 5 mg betahistine dose; about 2000 pg/mL for a 10 mg betahistine dose; about 4000 pg/mL for a 20 mg betahistine dose; or about 10500 pg/mL for a 40 mg betahistine dose.

In particular embodiments, the present disclosure is directed to pharmaceutical compositions as described herein, wherein after a single intranasal administration to a human, the $AUC_{0-last}$ ranges from about 80%-125% of: about 210 pg*hr/mL for a 5 mg betahistine dose; about 500 pg*hr/mL for a 10 mg betahistine dose; about 1600 pg*hr/mL for a 20 mg betahistine dose; or about 3500 pg*hr/mL for a 40 mg betahistine dose.

In particular embodiments, the present disclosure is directed to pharmaceutical compositions as described herein, wherein after a single intranasal administration to a human, the $AUC_{0-inf}$ ranges from about 80%-125% of: about 275 pg*hr/mL for a 5 mg betahistine dose; about 700 pg*hr/mL for a 10 mg betahistine dose; about 1630 pg*hr/mL for a 20 mg betahistine dose; or about 3940 pg*hr/mL for a 40 mg betahistine dose.

In still other embodiments, the present disclosure is directed to methods of treating an inner ear dysfunction or inner ear disorder, or treating or alleviating symptoms of an inner ear disorder, or increasing cochlear blood flow or cerebral blood flow in a subject comprising intranasally administering any of the compositions disclosed herein to said subject.

DETAILED DESCRIPTION

Figure 1:
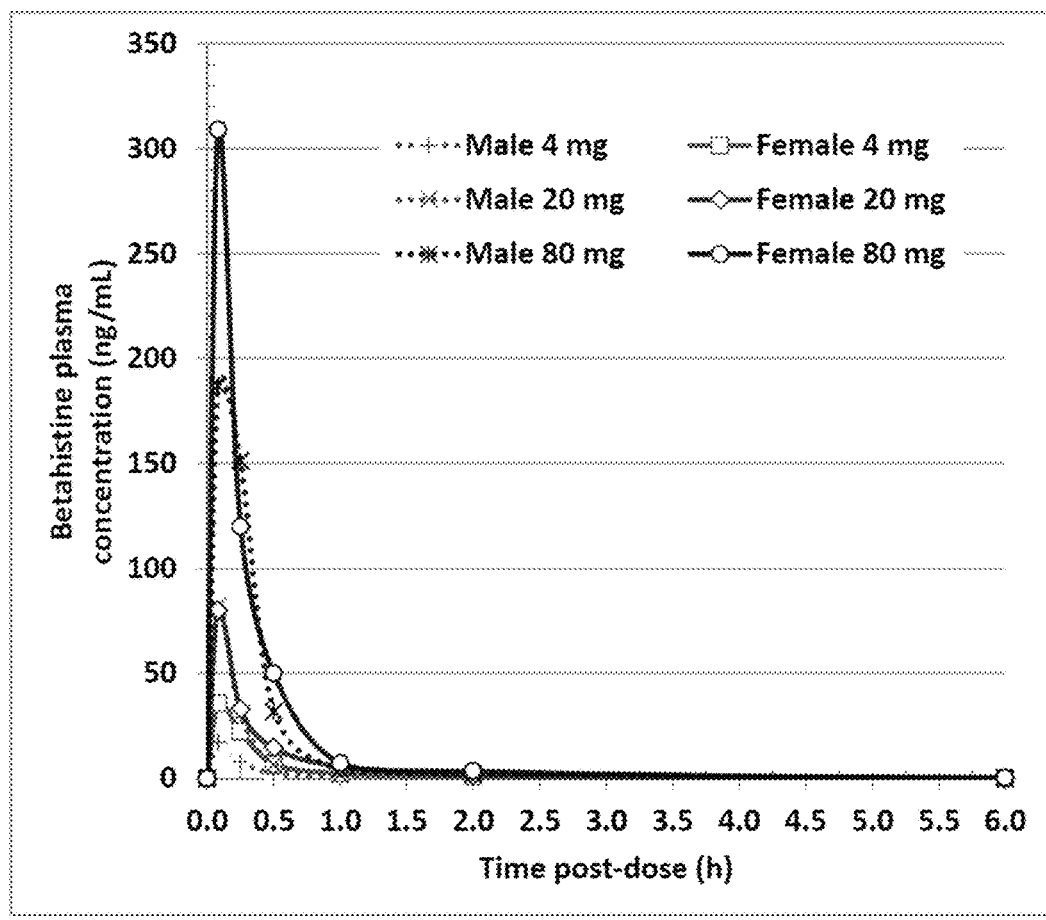
FIG. 1 shows the betahistine concentration in plasma from 6 beagle dogs following intranasal administration of a single dose of betahistine dihydrochloride 4, 20 or 80 mg over time.

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. In other contexts, the term "about" may refer to a value intermediate between adjacent values in a numerical sequence. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "treat," "treated," "treating" or "treatment" includes the diminishment or alleviation of at least one symptom associated or caused by the state, disorder or disease being treated. Treatment can be diminishment of one or several symptoms of a disorder or complete eradication of a disorder or a disease. Similarly, the term "prophylaxis" refers to the partial or total prevention of symptoms by administration of the active agent prior to the expected initiation of such symptoms.

As used herein, the term "subject," "individual" or "patient" is used interchangeably and refers to a vertebrate, preferably a mammal. Non-limiting examples include mice, dogs, rabbits, farm animals, sport animals, pets, and humans.

As used herein, "therapeutically effective amount" or an "effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition.

As used herein, the term "pharmaceutically acceptable salt of betahistine" refers to pharmaceutically acceptable acid addition salts of betahistine, especially those which are known to be non-toxic and are commonly used in the art of pharmaceutical formulation. In one embodiment, betahistine salt is an acid addition salt where the non-limiting example of the acid is selected from: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), or undecylenic acid. In another embodiment, suitable betahistine salts also include, but are not limited to, hydrochloride, hydrobromide, hydroiodide, tartrate, mesylate, citrate, phosphate, acetate, pamoate/embonate, nitrate, lactate, sulfate, methylsulfate, fumarate, oxalate, phthalate, maleate, and succinate. Further, betahistine salts may be a mono-salt or a bis-salt. In one embodiment, betahistine hydrochloride can be a betahistine monohydrochloride or a betahistine bis-hydrochloride.

In one embodiment of the present disclosure, the betahistine or a pharmaceutically acceptable salt thereof can be formulated in any form suited for administration by various pathways including nasally (e.g., solution, spray, drops, aerosol, gels, dry powders), orally (e.g., tablets, capsules, granules, syrups, elixirs, or powders) sublingually, buccally, parenterally (e.g., subcutaneous, intravenous, intramuscular, intrathecal, or intracisternal injection), or infusion techniques (e.g., as sterile injectable aqueous or non-aqueous solutions or suspensions), topically (e.g., drug-releasing skin patch, cream or ointment), intravaginally, by drench, transdermally, intradermally, pulmonary, by intra-uterine, by the use of an aerosol, or rectally (e.g., suppositories, in dosage unit formulations containing nontoxic, pharmaceutically acceptable vehicles or diluents). In one embodiment, the betahistine or a pharmaceutically acceptable salt thereof is formulated in any form suited for nasal or intranasal administration.

In one embodiment of the present disclosure, a pharmaceutical composition is provided comprising betahistine hydrochloride. In another embodiment, the pharmaceutical composition is provided comprising betahistine monohydrochloride. In another embodiment, the pharmaceutical composition is provided comprising betahistine dihydrochloride.

In one embodiment, the pharmaceutical composition comprises a particular polymorph of a betahistine or a pharmaceutically acceptable salt thereof. In one embodiment, the pharmaceutical composition comprises a particular polymorph of a betahistine or a pharmaceutically acceptable salt thereof is formulated in any form suited for nasal or intranasal administration.

In one embodiment of the present disclosure, a pharmaceutical composition is provided comprising betahistine or a pharmaceutically acceptable salt thereof. In particular embodiments, the pharmaceutical compositions of the present disclosure comprise solutions or suspensions of betahistine, or a pharmaceutically acceptable salt thereof. In another embodiment, a pharmaceutical composition is provided comprising betahistine or a pharmaceutically acceptable salt thereof and one or more viscosity agents or one or more pharmaceutically acceptable viscosity enhancing agents. Non limiting examples of suitable viscosity agents or viscosity enhancing agents include polyvinyl pyrrolidone, polyvinyl alcohol, methylcellulose, carboxymethyl cellulose-Na, hydroxyethylcellulose, hydroxypropyl cellulose, hydroxypropyl methylcellulose, polyethylene-oxide, Carbopol, polyethylene glycol, propylene glycol, glycerin, alginates, carrageenan, pectins, maltodextrin, sodium starch glycolate, tragacanth gum; gum arabic, microcrystalline cellulose and derivatives thereof. In one embodiment, the viscosity enhancing agent is polyvinyl pyrrolidone.

In another embodiment, the present disclosure is directed to a pharmaceutical composition comprising betahistine or a pharmaceutically acceptable salt thereof and one or more viscosity agents is an intranasal pharmaceutical composition. In one embodiment, the one or more viscosity agents in the formulation for intranasal administration allows the formulation to be retained at the application site long enough for the betahistine or a pharmaceutically acceptable salt thereof to be absorbed. In another embodiment, the presence of one or more viscosity agents in the formulation for intranasal administration does not prevent the formulation to be sprayed into the nasal cavity.

In one embodiment, the pharmaceutical compositions of the present disclosure have a viscosity in the range of about 0.1 cps to about 1000 cps or about 1 cps to about 100 cps. In one embodiment, the viscosity of the pharmaceutical composition of the present disclosure is about 0.1 cps, about 0.5 cps, about 1 cps, about 5 cps, about 10 cps, about 15 cps, about 20 cps, about 25 cps, about 30 cps, about 40 cps, about 45 cps, about 50 cps, about 55 cps, about 60 cps, about 65 cps, about 70 cps, about 75 cps, about 80 cps, about 85 cps, about 90 cps, about 95 cps, about 100 cps, about 105 cps, about 110 cps, about 115 cps, about 120 cps, about 125 cps, about 130 cps, about 135 cps, about 140 cps, about 145 cps, about 150 cps, about 175 cps, about 200 cps, about 250 cps, about 300 cps, about 350 cps, about 400 cps, about 450 cps, about 500 cps, about 550 cps, about 600 cps, about 650 cps, about 700 cps, about 750 cps, about 800 cps, about 850 cps, about 900 cps, about 950 cps, or about 1000 cps. In one embodiment, the viscosity of the pharmaceutical compositions described herein can be measured by the USP <911> Viscosity method.

In one embodiment, the pharmaceutical compositions of the present disclosure for nasal delivery have a viscosity of about 0.5 cps to about 10.5 cps, about 1 cps to about 10 cps, or about 1 cps to about 7 cps. In one embodiment, the pharmaceutical composition of the present disclosure for nasal delivery has a viscosity of about 0.5 cps, about 0.6 cps, about 0.7 cps, about 0.8 cps, about 0.9 cps, about 1.0 cps, about 1.1 cps, about 1.2 cps, about 1.3 cps, about 1.4 cps, about 1.5 cps, about 1.6 cps, about 1.7 cps, about 1.8 cps, about 1.9 cps, about 2.0 cps, about 2.1 cps, about 2.2 cps, about 2.3 cps, about 2.4 cps, about 2.5 cps, about 2.6 cps, about 2.7 cps, about 2.8 cps, about 2.9 cps, about 3.0 cps, about 3.1 cps, about 3.2 cps, about 3.3 cps, about 3.4 cps, about 3.5 cps, about 3.6 cps, about 3.7 cps, about 3.8 cps, about 3.9 cps, about 4.0 cps, about 4.1 cps, about 4.2 cps, about 4.3 cps, about 4.4 cps, about 4.5 cps, about 4.6 cps, about 4.7 cps, about 4.8 cps, about 4.9 cps, about 5.0 cps, about 5.1 cps, about 5.2 cps, about 5.3 cps, about 5.4 cps, about 5.5 cps, about 5.6 cps, about 5.7 cps, about 5.8 cps, about 5.9 cps, about 6.0 cps, about 6.1 cps, about 6.2 cps, about 6.3 cps, about 6.4 cps, about 6.5 cps, about 6.6 cps, about 6.7 cps, about 6.8 cps, about 6.9 cps, about 7.0 cps, about 7.1 cps, about 7.2 cps, about 7.3 cps, about 7.4 cps, about 7.5 cps, about 7.6 cps, about 7.7 cps, about 7.8 cps, about 7.9 cps, about 8.0 cps, about 8.1 cps, about 8.2 cps, about 8.3 cps, about 8.4 cps, about 8.5 cps, about 8.6 cps, about 8.7 cps, about 8.8 cps, about 8.9 cps, about 9.0 cps, about 9.1 cps, about 9.2 cps, about 9.3 cps, about 9.4 cps, about 9.5 cps, about 9.6 cps, about 9.7 cps, about 9.8 cps, about 9.9 cps, about 10.0 cps, about 10.1 cps, about 10.2 cps, about 10.3 cps, about 10.4 cps, about 10.5 cps, or any range between any of these values. In one embodiment, the pharmaceutical compositions of the present disclosure for nasal delivery are in an intranasal composition. In one embodiment, the viscosity of the pharmaceutical compositions described herein can be measured by the USP <911> Viscosity method.

In one embodiment, the pharmaceutical compositions of the present disclosure comprise one or more pharmaceutically acceptable moisturizing agents. Non-limiting examples of such moisturizing agents include glycerin, ethylene glycol, propylene glycol, propylene glycol 400, hexalene glycol, butylene glycol, dextrose, glyceryl triacetate, polydextrose, glycerol, glyceryl triacetate, sorbitol, and mannitol. In various embodiments, the pharmaceutical compositions of the present disclosure can include mixtures of pharmaceutically acceptable moisturizing agents.

In one embodiment, the one or more moisturizing agents are selected from glycerin, polyethylene glycol 400 and propylene glycol. In one embodiment, the pharmaceutical compositions of the present disclosure comprise glycerin. In another embodiment, the pharmaceutical composition of the present disclosure comprises polyethylene glycol 400. In other embodiments, the pharmaceutical composition of the present disclosure comprises propylene glycol. In some embodiments, the pharmaceutical compositions of the present disclosure comprise glycerin, polyethylene glycol 400 and propylene glycol.

In one embodiment, the pharmaceutical compositions of the present disclosure comprising one or more pharmaceutically acceptable moisturizing agents are intranasal pharmaceutical compositions. In one embodiment, one or more moisturizing agents in the intranasal pharmaceutical composition for intranasal administration moisturize the nasal mucosa, nasal tissues, and/or nasal membrane. In one embodiment, one or more moisturizing agents in the intranasal pharmaceutical composition for intranasal administration reduce irritation in the nasal cavity after administration. In some embodiments, the intranasal pharmaceutical composition of the present disclosure comprises glycerin, polyethylene glycol 400 and propylene glycol.

In another embodiment, a pharmaceutical composition is provided comprising betahistine or a pharmaceutically acceptable salt thereof, one or more viscosity agents, and one or more moisturizing agent. In one embodiment, the pharmaceutical composition is an intranasal pharmaceutical composition.

In one embodiment, the pharmaceutical compositions of the present disclosure comprise one or more pharmaceutically acceptable carriers and/or one or more pharmaceutically acceptable excipients.

In one embodiment, the pharmaceutical compositions of the present disclosure further comprise one or more additives, including but not limited to, preservatives, agents influencing osmolarity, complexing agents (such as, for example, sodium edetate), surfactants, agents which influence the pH and tonicity, and sensory masking agents. In one embodiment, the pharmaceutical composition of the present disclosure for intranasal delivery further comprises one or more additives, including but not limited to, preservatives, agents influencing osmolarity, complexing agents (such as, for example, sodium edetate), surfactants, agents which influence the pH and tonicity, and sensory masking agents.

Non-limiting examples of additives and/or excipients include benzyl alcohol, benzalkonium chloride, carboxymethyl cellulose sodium/cellulose microcrystalline, propylparaben, methylparaben, phenethyl alcohol, chlorobutanol, EDTA, ethanol, ascorbic acid, hydrochloric acid, sulfuric acid, sodium hydroxide, potassium phosphate, sodium phosphate, sodium citrate, sodium chloride, anhydrous dextrose, butylated hydroxyanisole, butylated, hydroxytoluene, PEG 400, PEG 3500, polyoxyl 400 stearate, polysorbate 20, polysorbate 80, glycerin, propylene glycol, glyceryl triacetate, glycerol, ethylene glycol, sorbitol, mannitol, and alginates, carrageenan, pectins, tragacanth gum, gum arabic.

For the purposes of this disclosure, the pharmaceutical composition comprising betahistine or a pharmaceutically acceptable salt thereof, may be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injections as used herein include administration through catheters.

The pharmaceutical composition disclosed herein can be formulated in accordance with the routine procedures adapted for desired administration route. Accordingly, a pharmaceutical composition herein can take such forms as suspensions, solutions or emulsions in oily or aqueous vehicles, and can contain formulatory agents such as suspending, stabilizing and/or dispersing agents. Alternatively, the betahistine or a pharmaceutically acceptable salt thereof can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In one embodiment, pharmaceutically acceptable carriers are well known to those skilled in the art and include, but are not limited to, buffer solutions, saline, and water. In one embodiment, a pharmaceutically acceptable carrier includes about 0.01 to about 0.1 M phosphate buffer or saline (e.g., 0.8% saline). In one embodiment, the buffer solution comprises sodium phosphate dibasic and sodium phosphate monobasic. In such embodiments, the buffering agent adjusts the pH of the composition within a range suitable to permit rapid absorption of betahistine through the nasal mucosa, and to minimize irritation. For example, pH can be controlled to fall within a range of about 4 to about 9, including pH values of about 4, about 4.2, about 4.4, about 48, about 5, about 5.2, about 5.4, about 5.6, about 5.8, about 6, about 6.2, about 6.4, about 6.8, about 7, about 7.2, about 7.4, about 7.6, about 7.8, about 8, about 8.2, about 8.4, about 8.6, about 8.8, or about 9, inclusive of all ranges between any of these values. In one embodiment, the pharmaceutical composition of the present disclosure has a pH value of about 5. In another embodiment, the pharmaceutical composition of the present disclosure having a pH value of about 5 demonstrates improved solubility and stability of betahistine or a pharmaceutically acceptable salt thereof when compared to a composition with greater pH value.

Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, alcoholic/aqueous solutions (such as ethanol/water), glycerol and or glycerol/aqueous mixtures, emulsions or suspensions, including saline and buffered media. Oral carriers can be elixirs, syrups, capsules, tablets and the like.

Liquid carriers suitable for use in the present application can be used in preparing solutions, suspensions, or emulsions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). If the compositions of the present invention are administered from pressurized containers (e.g., pressurized, metered dose dispensers), the liquid carrier for pressurized compositions disclosed herein can be a halogenated hydrocarbon, hydrocarbon, carbon dioxide, or other pharmaceutically acceptable propellant.

Solid carriers suitable for use in the present application (e.g., when the compositions are provided as a intranasal dry powder) include, but are not limited to, inert substances such as lactose, starch, glucose, methyl-cellulose, magnesium stearate, dicalcium phosphate, mannitol and the like.

Flavoring agents and flavor enhancers may make the dosage form more palatable to the patient, in the event that some of the intranasally administered composition is ingested. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Sensory masking agent can be used to taste mask and/or odor mask sensation in connection with the administration of the pharmaceutical composition. In one embodiment, odor masking agent can include scented aromatic masking agent. In one embodiment, any known sensory masking agents which is known in the pharmaceutical literature can be considered.

Compositions of the present disclosure may also include a dye using any pharmaceutically acceptable colorant to improve their appearance and/or facilitate patient identification of the product and unit dosage level in liquid pharmaceutical compositions of the present invention where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions and/or combinations may contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, quaternary ammonium compounds such as benzethonium chloride, benzoxonium chloride, benzododecinium bromide, alkyltrimethilammonium bromide, cetrimonium bromide, benzalkonium chloride, phenylethyl alcohol, benzoic acid and esters and salts thereof, e.g. $C_1$-$C_7$-alkyl esters of 4-hydroxybenzoic acid, such as methyl 4-hydroxybenzoate, sodium methyl 4-hydroxybenzoate or propyl 4-hydroxybenzoate, butylated hydroxyl toluene, butylated hydroxyanisole, cetylpyridinium chloride, cetrimide; parabens and derivatives such as propylparaben or methylparaben; alkyl acids, such as potassium sorbate, sorbic acid, calcium sorbate, sodium sorbate; biguanides, e.g. chlorhexidine or nasally acceptable salts thereof, e.g. chlorhexidine digluconate, chlorhexidine acetate or chlorhexidine chloride, 2-phenoxyethanol; boric acids; phenols such as 4-chlorocresol, 4-chloroxylenol, dichlorophene or hexachlorophene and chelators such as ethylenediamine tetraacetic acid (EDTA) or ethylenediamine-N,N'-disuccinic acid (EDDS) may be added at levels safe for administration to improve storage stability.

A liquid composition and/or combination may also contain additives or excipients such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The pharmaceutical compositions and/or pharmaceutical combinations of the invention may be in the form of an aqueous or oleaginous suspension. In one embodiment, the pharmaceutical composition and/or pharmaceutical combinations of the invention may be in the form of a sterile aqueous or oleaginous suspension. This suspension may be formulated according to the known art using suitable dispersing or wetting agents and suspending agents. The sterile solution or suspension may be dissolved or dispersed in a non-toxic pharmaceutically acceptable diluent or solvent, such as a solution in 1,3-butane-diol or prepared as a lyophilized powder for delivery as a dry powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides.

Dosage forms include powders or liquids capable of administration via vaporization or an aerosol, or as a dry powder. Dosing can be controlled through the use of a metered pump dispensing device, such as are known in the art.

In one embodiment of the present disclosure, the betahistine or a pharmaceutically acceptable salt thereof can be formulated in any way suited for nasal or intranasal administration. In one embodiment of the present disclosure, an intranasal pharmaceutical composition is provided comprising betahistine hydrochloride. In another embodiment, the intranasal pharmaceutical composition is provided comprising betahistine monohydrochloride. In another embodiment, the intranasal pharmaceutical composition is provided comprising betahistine dihydrochloride.

In another embodiment, an intranasal pharmaceutical composition comprises betahistine free base. In another embodiment, an intranasal pharmaceutical composition comprises betahistine pharmaceutically acceptable salts selected from betahistine hydrochloride, betahistine dihydrochloride, betahistine fumarate, betahistine maleate, betahistine tartrate, betahistine citrate, betahistine succinate, betahistine phthalate and betahistine mesylate, betahistine hydrobromide, betahistine hydroiodide, betahistine mesylate, betahistine phosphate, betahistine acetate, betahistine pamoate/embonate, betahistine nitrate, betahistine lactate, betahistine sulfate, betahistine methylsulfate, betahistine oxalate, or any other pharmaceutically acceptable betahistine salt disclosed herein or known in the art.

In one embodiment, to improve nasal delivery and retention, the betahistine or a pharmaceutically acceptable salt thereof may be encapsulated with cyclodextrins, or formulated with other agents expected to enhance delivery and retention in the nasal mucosa.

In one embodiment, the present disclosure provides sustained or controlled release formulations of betahistine. For example, bioadhesive polymers have shown good potential for nasal formulations and can control the rate and extent of drug release. Additionally, the prolonged contact time afforded by bioadhesive polymers at the site of absorption can improve drug bioavailability. Thus, nasal formulations comprising bioadhesive polymers, e.g. chitosan microspheres, are contemplated by the present disclosure. Various biocompatible and biodegradable polymers that may be used to formulate sustained release nasal compositions include poly-vinyl alcohol, chitosan, carbopol, alginate, hydroxypropyl methylcellulose, hydroxypropyl cellulose, starch and gellan gum. In some embodiments, liposomal formulations may also be used to provide sustained release. In other embodiments, nasal microparticles or microspheres comprising albumin, starch, dextran and/or chitosan may be used to provide sustained release. These and other sustained nasal drug delivery systems are reviewed by Ghori et al. (*American Journal of Pharmacological Sciences*, 2015, Vol. 3, No. 5, 110-119), which is incorporated by reference herein in its entirety for all purposes.

In some embodiments, controlled release nasal delivery systems disclosed in U.S. Pat. No. 8,574,622, which is incorporated by reference herein in its entirety for all purposes, may be used to provide sustained release of the active.

In some embodiments, formulations comprising absorption enhancers may be used to provide sustained release. The purpose of absorption enhancement in intranasal drug delivery is to facilitate or increase the uptake of the drug. This can be achieved by either prolonging the residence time to obtain a larger time frame for absorption, or by increasing the permeation of the mucosal tissue. Absorption enhancement is achieved through mucoadhesion or in situ gelling for a prolonged residence time, sometimes a combination thereof, or enhancing permeation by weakening cellular junctions or increasing the fluidity of membrane bilayers. Accordingly, formulations comprising mucoadhesive excipients and/or in situ gelling agents may be used for intranasal delivery of betahistine. For example, in one embodiment, sustained release formulations comprising mucoadhesive excipients such as carbomers, cellulose derivates, starch derivates, or chitosans may be used in the present invention.

In another embodiment, sustained release formulations are in the form of in situ nasal gelling systems comprising stimulus responsive polymers. Stimulus responsive polymers include polymers that alter the rheological characteristics of in situ gelling formulations upon contact with the nasal mucosa due to changes in temperature, pH, or ions. Examples of stimulus responsive polymers or in situ gelling agents include, but are not limited to, poloxamers, pectin, and chitosan-based polymers. In one embodiment, in situ gelling systems may further comprise mucoadhesive excipients such as carbopol 934P, chitosan, sodium carboxymethyl cellulose (NaCMC), hydroxypropyl methylcellulose (HPMC), hydroxypropyl cellulose and methylcellulose. In some embodiments, nasal formulations comprising stimulus responsive polymers, which may optionally further comprise mucoadhesive excipients, e.g. those disclosed in Chonkar et al., *Indian J Pharm Sci.*, 2015 July-August; 77(4): 367-375, incorporated by reference herein in its entirety for all purposes, may be used as sustained release formulations to carry out the present invention. In other embodiments, mucoadhesive microspheres comprising betahistine dihydrochloride disclosed in Pilicheva et al. (*International Journal of Drug Delivery*, 2013, 5(4): 389-401), incorporated by reference herein in its entirety for all purposes, may be adapted for intransal delivery of betahistine in accordance with the present invention.

In some embodiments, formulations comprising absorption enhancers such as alkyl glycosides disclosed in U.S. Pre-Grant Publication Nos. 2006/0045868, 2006/0045869, 2008/0299079 or formulations comprising soybean-derived steryl glycoside and sterol mixtures as absorption enhancers (Ando et al., Biological and Pharmaceutical Bulletin, 21(8), 862-865) may be used to provide sustained release, each of these documents is herein incorporated by reference for all purposes. In some other embodiments, formulations comprising micelles of sodium glycocholate or micelles of sodium glycocholate mixed with fatty acid (e.g. linoleic acid) as absorption enhancers may be used as sustained release formulations. Other examples of absorption enhancers include cyclodextrins, phospholipids, and chitosans.

Exemplary nasal formulations based on thermogelling polymers such as poloxamers are disclosed by Sharma et al. (Drug Dev Ind Pharm. 2014 July; 40(7):869-78); Cho et al. (J Pharm Sci. 2011 February; 100(2):681-91); Choi et al. (Int Forum Allergy Rhinol. 2017 July; 7(7):705-711); and Balakrishnan et al. (Molecules. 2015 Mar. 4; 20(3):4124-35), each of these documents is incorporated by reference herein in its entirety for all purposes. Formulations disclosed in these references may be adapted for intransal delivery of betahistine in accordance with the present invention.

In one embodiment, the pharmaceutical composition of the present disclosure comprises ingredients disclosed in Table 1. In another embodiment, the pharmaceutical composition of the present disclosure is substantially similar to the composition disclosed in Table 1. In one embodiment, the pharmaceutical composition of the present disclosure comprises ingredients disclosed in Table 1 with varying amounts of each ingredient.

TABLE 1

Sample Betahistine Formulation

| Ingredient | Amount | Concentration (mg/ml) |
|---|---|---|
| Betahistine dihydrochloride | 5 g* | 50.0 |
| Benzalkonium chloride | 20 mg | 0.2 |
| Glycerin | 100 mg | 1.0 |
| Edetate Disodium | 20 mg | 0.2 |
| Polyvinyl Pyrrolidone | 1.25 g | 12.5 |
| Polyethylene Glycol 400 | 3.75 g | 37.5 |
| Sodium Phosphate Dibasic | 97.5 mg | 0.975 |
| Propylene Glycol | 2 g | 20 |
| Sodium Phosphate Monobasic | 552.5 mg | 5.525 |
| 1M Sodium Hydroxide | 4.38 mL** | pH 5.0 |
| Water for Injecton | To 100 ml | |

For 200 mg/mL betahistine dihydrochloride formulation,
*20 g of betahistine dihydrochloride and
**9.3 mL 1M sodium hydroxide can be substituted.

Pharmacokinetics

In one embodiment, the pharmaceutical composition of the present disclosure provides detectable $C_{max}$ of betahistine in human plasma concentration after single dose administration of the pharmaceutical composition of the present disclosure. In one embodiment, the $C_{max}$ of betahistine in human plasma concentration after single dose administration of the pharmaceutical composition of the present disclosure is at least about 0.2 ng/mL or at least about 0.5 ng/mL. In one embodiment, the $C_{max}$ is measured after a single dose administration of about 1 mg to about 250 mg of betahistine or a pharmaceutically acceptable salt. In one embodiment, the $C_{max}$ is measured after a single dose administration of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt. In other embodiments, the $C_{max}$ for a 5 mg betahistine dose, administered intranasally, ranges from about 80% to about 125% of about 640 pg/mL; about 80% to about 125% of about 2000 pg/mL for a 10 mg betahistine dose, administered intranasally; about 80% to about 125% of about 4000 pg/mL for a 20 mg betahistine dose, administered intranasally; and about 80% to about 125% of about 10500 pg/mL for a 40 mg betahistine days, administered intranasally. In other embodiments, the $C_{max}$ for a 5 mg betahistine dose, administered intranasally, ranges from about 80% to about 125% of about 230 to about 1260 pg/mL; about 80% to about 125% of about 790 to about 3470 pg/mL for a 10 mg betahistine dose, administered intranasally; about 80% to about 125% of about 1900 to about 8300 pg/mL for a 20 mg betahistine dose, administered intranasally; and about 80% to about 125% of about 8000 to about 16000 pg/mL for a 40 mg betahistine dose, administered intranasally.

In one embodiment, the $C_{max}$ for a 5 mg betahistine dose, administered intranasally, ranges from about 80% to about 125% of about 500 pg/mL, 550 pg/mL, 600 pg/mL, 650 pg/mL, 700 pg/mL, 750 pg/mL, 800 pg/mL, 850 pg/mL, 900 pg/mL, 950 pg/mL, 1000 pg/mL, 1050 pg/mL, 1100 pg/mL, 1150 pg/mL, 1200 pg/mL, 1250 pg/mL, 1300 pg/mL, 1350 pg/mL, 1400 pg/mL, 1450 pg/mL, 1500 pg/mL, 1550 pg/mL, 1600 pg/mL, 1650 pg/mL, 1700 pg/mL, 1750 pg/mL, 1800 pg/mL, 1850 pg/mL, 1900 pg/mL, 1950 pg/mL, 2000 pg/mL, 2050 pg/mL, 2100 pg/mL, 2150 pg/mL, 2200 pg/mL, 2250 pg/mL, 2300 pg/mL, 2350 pg/mL, 2400 pg/mL, 2450 pg/mL, 2500 pg/mL, 2550 pg/mL, 2600 pg/mL, 2650 pg/mL, 2700 pg/mL, 2750 pg/mL, 2800 pg/mL, 2850 pg/mL, 2900 pg/mL, 2950 pg/mL, or about 3000 pg/mL.

In other embodiments, the $C_{max}$ for a 5 mg betahistine dose, administered intranasally, ranges from about 80% to about 125% of about 600 to about 3000 pg/mL, about 600 to about 2800 pg/mL, about 600 to about 2600 pg/mL, about 600 to about 2400 pg/mL, about 600 to about 2200 pg/mL, about 600 to about 2000 pg/mL, about 600 to about 1800 pg/mL, about 600 to about 1600 pg/mL, about 600 to about 1400 pg/mL, about 600 to about 1200 pg/mL, about 600 to about 1000 pg/mL, about 500 to about 2500 pg/mL, about 500 to about 2300 pg/mL, about 500 to about 2100 pg/mL, about 500 to about 1900 pg/mL, about 500 to about 1700 pg/mL, about 500 to about 1500 pg/mL, about 500 to about 1300 pg/mL, or about 500 to about 1100 pg/mL.

In one embodiment, the $C_{max}$ for a 10 mg betahistine dose, administered intranasally, ranges from about 80% to about 125% of about 1800 pg/mL, 2000 pg/mL, 2200 pg/mL, 2400 pg/mL, 2600 pg/mL, 2800 pg/mL, 3000 pg/mL, 3200 pg/mL, 3400 pg/mL, 3600 pg/mL, 3800 pg/mL, 4000 pg/mL, 4200 pg/mL, 4400 pg/mL, 4600 pg/mL, 4800 pg/mL, 5000 pg/mL, 5200 pg/mL, 5400 pg/mL, 5600 pg/mL, 5800 pg/mL, 6000 pg/mL, 6200 pg/mL, 6400 pg/mL, 6600 pg/mL, 6800 pg/mL, 7000 pg/mL, 7200 pg/mL, 7400 pg/mL, 7600, 7800 pg/mL, or about 8000 pg/mL.

In other embodiments, the $C_{max}$ for a 10 mg betahistine dose, administered intranasally, ranges from about 80% to about 125% of about 1800 to about 4500 pg/mL, about 2000 to about 5000 pg/mL, about 2200 to about 5500 pg/mL, about 2500 to about 5500 pg/mL, about 1600 to about 3000 pg/mL, about 1600 to about 3300 pg/mL, or about 1600 to about 3500 pg/mL. In one embodiment, the $C_{max}$ for a 20 mg betahistine dose, administered intranasally, ranges from about 80% to about 125% of about 3600 pg/mL, 3800 pg/mL, 4000 pg/mL, 4200 pg/mL, 4400 pg/mL, 4600 pg/mL, 4800 pg/mL, 5000 pg/mL, 5200 pg/mL, 5400 pg/mL, 5600 pg/mL, 5800 pg/mL, 6000 pg/mL, 6200 pg/mL, 6400 pg/mL, 6600 pg/mL, 6800 pg/mL, 7000 pg/mL, 7200 pg/mL, 7400 pg/mL, 7600 pg/mL, 7800 pg/mL, 8000 pg/mL, 8200 pg/mL, 8400 pg/mL, 8600 pg/mL, 8800 pg/mL, or 9000 pg/mL.

In other embodiments, the $C_{max}$ for a 20 mg betahistine dose, administered intranasally, ranges from about 80% to about 125% of about 3000 to about 8000 pg/mL, about 3000 to about 7700 pg/mL, about 3000 to about 7500 pg/mL, about 3000 to about 7300 pg/mL, about 3000 to about 7100 pg/mL, about 3000 to about 6900 pg/mL, about 3000 to about 6700 pg/mL, about 3000 to about 6500 pg/mL, about 3000 to about 6300 pg/mL, about 3000 to about 6100 pg/mL, about 3000 to about 5800 pg/mL, about 3000 to about 5600 pg/mL, about 3000 to about 5400 pg/mL, about 3000 to about 5200 pg/mL, about 3000 to about 5000 pg/mL, about 3250 to about 8000 pg/mL, about 3250 to about 7750 pg/mL, about 3250 to about 7500 pg/mL, about 3250 to about 7250 pg/mL, about 3250 to about 7000 pg/mL, about 3250 to about 6800 pg/mL, about 3250 to about 6600 pg/mL, about 3250 to about 6400 pg/mL, about 3250 to about 6200 pg/mL, about 3250 to about 6000 pg/mL, about 3250 to about 5800 pg/mL, about 3250 to about 5600 pg/mL, about 3250 to about 5400 pg/mL, about 3250 to about 5200 pg/mL, about 3250 to about 5000 pg/mL, about 3250 to about 4800 pg/mL, about 3500 to about 8000 pg/mL, about 3500 to about 7800 pg/mL, about 3500 to about 7600 pg/mL, about 3500 to about 7400 pg/mL, about 3500 to about 7200 pg/mL, about 3500 to about 7000 pg/mL, about 3500 to about 6800 pg/mL, about 3500 to about 6600 pg/mL, about 3500 to about 6400 pg/mL, about 3500 to about 6200 pg/mL, about 3500 to about 6000 pg/mL, about 3500 to about 5800 pg/mL, about 3500 to about 5600 pg/mL, about 3500 to about 5300 pg/mL, about 3500 to about 5100 pg/mL, about 3700 to about 7500 pg/mL, about 3700 to about 7200 pg/mL, about 3700 to about 7000 pg/mL, about 3700 to about 6800 pg/mL, about 3700 to about 6500 pg/mL, about 3700 to about 6300 pg/mL, about 3700 to about 6100 pg/mL, about 3700 to about 5900 pg/mL, about 3700 to about 5700 pg/mL, about 3700 to about 5500 pg/mL, about 3700 to about 5300 pg/mL, or about 3700 to about 5100 pg/mL.

In one embodiment, the $C_{max}$ for a 40 mg betahistine dose, administered intranasally, ranges from about 80% to about 125% of about 8000 pg/mL, 8500 pg/mL, 9000 pg/mL, 9500 pg/mL, 9800 pg/mL, 10000 pg/mL, 10300 pg/mL, 10500 pg/mL, 10750 pg/mL, 11000 pg/mL, 11250 pg/mL, 11500 pg/mL, 11750 pg/mL, 12000 pg/mL, 12250 pg/mL, 12500 pg/mL, 12750 pg/mL, 13000 pg/mL, 13250 pg/mL, 13500 pg/mL, 13750 pg/mL, 14000 pg/mL, 14250 pg/mL, 14500 pg/mL, 14750 pg/mL, 15000 pg/mL, 15250 pg/mL, 15500 pg/mL, 15750 pg/mL, 16000 pg/mL, 16500 pg/mL, 17000 pg/mL, 17500 pg/mL, 18000 pg/mL, 18500 pg/mL, 19000 pg/mL, 19500 pg/mL, or 20000 pg/mL.

In other embodiments, the $C_{max}$ for a 40 mg betahistine dose, administered intranasally, ranges from about 80% to about 125% of about 8000 to about 20000 pg/mL, about 8000 to about 19000 pg/mL, about 8000 to about 18500 pg/mL, about 8000 to about 18000 pg/mL, about 8000 to about 17500 pg/mL, about 8000 to about 17000 pg/mL, about 8000 to about 16500 pg/mL, about 8000 to about 16000 pg/mL, about 8000 to about 15500 pg/mL, about 8000 to about 15000 pg/mL, about 8000 to about 14500 pg/mL, about 8000 to about 14000 pg/mL, about 8000 to about 13500 pg/mL, about 8000 to about 13000 pg/mL, about 8000 to about 12500 pg/mL, about 9000 to about 19500 pg/mL, about 9000 to about 19000 pg/mL, about 9000 to about 18500 pg/mL, about 9000 to about 18000 pg/mL, about 9000 to about 17500 pg/mL, about 9000 to about 17000 pg/mL, about 9000 to about 16500 pg/mL, about 9000 to about 16000 pg/mL, about 9000 to about 15500 pg/mL, about 9000 to about 15000 pg/mL, about 9000 to about 14500 pg/mL, about 9000 to about 14000 pg/mL, about 9000 to about 13500 pg/mL, about 9000 to about 13000 pg/mL, about 10000 to about 18500 pg/mL, about 10000 to about 18000 pg/mL, about 10000 to about 17500 pg/mL, about 10000 to about 17000 pg/mL, about 10000 to about 16500 pg/mL, about 10000 to about 16000 pg/mL, about 10000 to about 15500 pg/mL, about 10000 to about 15000 pg/mL, about 10000 to about 14500 pg/mL, or about 10000 to about 14000 pg/mL.

In one embodiment, the $C_{max}$ for a 60 mg betahistine dose, administered intranasally, ranges from about 80% to about 125% of about 14000 pg/mL, 14250 pg/mL, 14500 pg/mL, 14750 pg/mL, 15000 pg/mL, 15250 pg/mL, 15500 pg/mL, 15750 pg/mL, 16000 pg/mL. 16250 pg/mL, 16500 pg/mL, 16750 pg/mL, 17000 pg/mL, 17250 pg/mL, 17500 pg/mL, 17750 pg/mL, 18000 pg/mL, 18250 pg/mL, 18500 pg/mL, or 19000 pg/mL.

In other embodiments, the $C_{max}$ for a 60 mg betahistine dose, administered intranasally, ranges from about 80% to about 125% of about 13500 to about 19000 pg/mL, about 13500 to about 18500 pg/mL, about 13500 to about 18250 pg/mL, about 13500 to about 18000 pg/mL, about 13500 to about 17750 pg/mL, about 13500 to about 17500 pg/mL, about 13500 to about 17250 pg/mL, about 13500 to about 17000 pg/mL, about 13500 to about 16500 pg/mL, about 13500 to about 16000 pg/mL, about 14000 to about 19000 pg/mL, about 14000 to about 18500 pg/mL, about 14000 to about 18250 pg/mL, about 14000 to about 18000 pg/mL, about 14000 to about 17750 pg/mL, about 14000 to about 17500 pg/mL, about 14000 to about 17250 pg/mL, about 14000 to about 17000 pg/mL, about 14000 to about 16500 pg/mL, about 14000 to about 16000 pg/mL, about 14500 to about 18500 pg/mL, about 14500 to about 18250 pg/mL, about 14500 to about 18000 pg/mL, about 14500 to about 17750 pg/mL, about 14500 to about 17500 pg/mL, about 14500 to about 17250 pg/mL, about 14500 to about 17000 pg/mL, or about 14500 to about 16500 pg/mL.

In one embodiment, the $C_{max}$ for a 80 mg betahistine dose, administered intranasally, ranges from about 80% to about 125% of about 18000 pg/mL, 18500 pg/mL, 19000 pg/mL, 19250 pg/mL, 19500 pg/mL, 19750 pg/mL, 20000 pg/mL, 20250 pg/mL, 20500 pg/mL, 20750 pg/mL, 21000 pg/mL, 21250 pg/mL, 21500 pg/mL, 21750 pg/mL, 22000 pg/mL, 22250 pg/mL, 22500 pg/mL, 22750 pg/mL, 23000 pg/mL, 23250 pg/mL, 23500 pg/mL, 23750 pg/mL, or 24000 pg/mL.

In other embodiments, the $C_{max}$ for a 80 mg betahistine dose, administered intranasally, ranges from about 80% to about 125% of about 18000 to about 25000 pg/mL, about 18000 to about 24500 pg/mL, about 18000 to about 24000 pg/mL, about 18000 to about 23750 pg/mL, about 18000 to about 23500 pg/mL, about 18000 to about 23250 pg/mL, about 18000 to about 23000 pg/mL, about 18000 to about 22750 pg/mL, about 18000 to about 22500 pg/mL, about 18000 to about 22250 pg/mL, about 18000 to about 22000 pg/mL, about 18500 to about 25000 pg/mL, about 18500 to about 24500 pg/mL, about 18500 to about 24000 pg/mL, about 18500 to about 23750 pg/mL, about 18500 to about 23500 pg/mL, about 18500 to about 23250 pg/mL, about 18500 to about 23000 pg/mL, about 18500 to about 22750 pg/mL, about 18500 to about 22500 pg/mL, about 18500 to about 22250 pg/mL, about 18500 to about 22000 pg/mL, about 19000 to about 25000 pg/mL, about 19000 to about 24500 pg/mL, about 19000 to about 24250 pg/mL, about 19000 to about 24000 pg/mL, about 19000 to about 23750 pg/mL, about 19000 to about 23500 pg/mL, about 19000 to about 23250 pg/mL, about 19000 to about 23000 pg/mL, about 19000 to about 22750 pg/mL, about 19000 to about 22500 pg/mL, about 19000 to about 22250 pg/mL, about 19000 to about 22000 pg/mL, about 19500 to about 24500 pg/mL, about 19500 to about 24250 pg/mL, about 19500 to about 24000 pg/mL, about 19500 to about 23750 pg/mL, about 19500 to about 23500 pg/mL, about 19500 to about 23250 pg/mL, about 19500 to about 23000 pg/mL, about 19500 to about 22750 pg/mL, about 19500 to about 22500 pg/mL, about 19500 to about 22250 pg/mL, or about 19500 to about 22000 pg/mL.

In one embodiment, the $C_{max}$ of betahistine in human plasma concentration after single dose administration of the intranasal pharmaceutical composition of the present disclosure is at least about 0.2 ng/mL or at least about 0.5 ng/mL. In one embodiment, the $C_{max}$ of betahistine in human plasma concentration after single dose administration of the intranasal pharmaceutical composition of the present disclosure is at least about 0.2 ng/mL, at least about 0.3 ng/mL, at least about 0.4 ng/mL, at least about 0.5 ng/mL, at least about 0.6 ng/mL, at least about 0.7 ng/mL, at least about 0.8 ng/mL, at least about 0.9 ng/mL, at least about 1 ng/mL, at least about 1.5 ng/mL, at least about 2 ng/mL, at least about 2.5 ng/mL, at least about 3 ng/mL, at least about 3.5 ng/mL, at least about 4 ng/mL, at least about 4.5 ng/mL, at least about 5 ng/mL, at least about 5.5 ng/mL, at least about 6 ng/mL, at least about 7.5 ng/mL, at least about 8 ng/mL, at least about 8.5 ng/mL, at least about 9 ng/mL, at least about 9.5 ng/mL, or at least about 10 ng/mL.

In one embodiment, the $C_{max}$ of betahistine in human plasma concentration after single dose administration of the intranasal pharmaceutical composition of the present disclosure is at least about 10 ng/mL, at least about 11 ng/mL, at least about 12 ng/mL, at least about 13 ng/mL, at least about 14 ng/mL, at least about 15 ng/mL, at least about 16 ng/mL, at least about 17 ng/mL, at least about 18 ng/mL, at least about 19 ng/mL, at least about 20 ng/mL, at least about 21 ng/mL, at least about 22 ng/mL, at least about 23 ng/mL, at least about 24 ng/mL, at least about 25 ng/mL, at least about 26 ng/mL, at least about 27 ng/mL, at least about 28 ng/mL, at least about 29 ng/mL, or at least about 30 ng/mL, In one embodiment, the $C_{max}$ of betahistine in human plasma concentration after single dose administration of the intranasal pharmaceutical composition of the present disclosure is at least about 3.5 ng/mL. In one embodiment, the $C_{max}$ of betahistine in human plasma concentration is measured after single dose administration of the intranasal pharmaceutical composition comprising about 1 mg to about 200 mg of betahistine or a pharmaceutically acceptable salt. In one embodiment, the $C_{max}$ is measured after a single intranasal dose administration of about 5 mg, 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg, of betahistine or a pharmaceutically acceptable salt.

In one embodiment, the $C_{max}$ is measured after a single intranasal dose administration of about 20 mg or about 40 mg of betahistine or a pharmaceutically acceptable salt. In another embodiment, the $C_{max}$ is measured after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the intranasal pharmaceutical composition of the present disclosure demonstrates good tolerance and a dose-dependent increase in betahistine plasma concentrations, higher than what can be detected after oral betahistine administration.

In one embodiment, the pharmaceutical composition of the present disclosure provides a $t_{max}$ of betahistine in human plasma concentration after single dose administration of the pharmaceutical composition of the present disclosure. In one embodiment, the $t_{max}$ of betahistine in human plasma concentration after single dose administration of the pharmaceutical composition of the present disclosure is about 0.05 h or greater, 0.06 h or greater, 0.07 h or greater, about 0.08 h or greater, about 0.09 h or greater, about 0.1 h or greater, about 0.11 h or greater, about 0.12 h or greater, about 0.13 h or greater, about 0.14 h or greater, about 0.15 h or greater, about 0.16 h or greater, about 0.17 h or greater, about 0.18 h or greater, about 0.19 h or greater, about 0.2 h or greater, about 0.25 h or greater, or about 0.3 h or greater. In one embodiment, the $t_{max}$ is measured after a single dose administration of about 1 mg to about 250 mg of betahistine or a pharmaceutically acceptable salt. In one embodiment, the $t_{max}$ is measured after a single dose of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the $t_{max}$ of betahistine in human plasma concentration after single dose administration of the intranasal pharmaceutical composition of the present disclosure is about 0.05 h or greater, 0.06 h or greater, 0.07 h or greater, about 0.08 h or greater, about 0.09 h or greater, about 0.1 h or greater, about 0.11 h or greater, about 0.12 h or greater, about 0.13 h or greater, about 0.14 h or greater, about 0.15 h or greater, about 0.16 h or greater, about 0.17 h or greater, about 0.18 h or greater, about 0.19 h or greater, about 0.2 h or greater, about 0.25 h or greater, or about 0.3 h or greater. In one embodiment, the $t_{max}$ of betahistine in human plasma concentration after single dose administration of the intranasal pharmaceutical composition of the present disclosure is about 0.09 h or greater, about 0.1 h or greater, about 0.11 h or greater, or about 0.12 h or greater. In one embodiment, the $t_{max}$ of betahistine in human plasma concentration is determined after single dose administration of the intranasal pharmaceutical composition comprising about 1 mg to about 200 mg of betahistine or a pharmaceutically acceptable salt. In one embodiment, the $t_{max}$ is determined after a single intranasal dose administration of about 5 mg, 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg, of betahistine or a pharmaceutically acceptable salt.

In one embodiment, the $t_{max}$ is determined after a single intranasal dose administration of about 20 mg or about 40 mg of betahistine or a pharmaceutically acceptable salt. In another embodiment, the $t_{max}$ is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the pharmaceutical composition of the present disclosure provides an $AUC_{0-last}$ of betahistine in human plasma concentration after single dose administration of the pharmaceutical composition of the present disclosure of at least about 50 hr*pg/mL, at least about 100 hr*pg/mL, at least about 200 hr*pg/mL, at least about 250 hr*pg/mL, at least about 300 hr*pg/mL, at least about 400 hr*pg/mL, at least about 500 hr*pg/mL, at least about 600 hr*pg/mL, at least about 700 hr*pg/mL, at least about 800 hr*pg/mL, at least about 900 hr*pg/mL, at least about 1000 hr*pg/mL, at least about 1100 hr*pg/mL, at least about 1200 hr*pg/mL, at least about 1300 hr*pg/mL, at least about 1400 hr*pg/mL, at least about 1500 hr*pg/mL, at least about 1600 hr*pg/mL, at least about 1700 hr*pg/mL, at least about 1800 hr*pg/mL, at least about 1900 hr*pg/mL, at least about 2000 hr*pg/mL, at least about 2100 hr*pg/mL, at least about 2200 hr*pg/mL, at least about 2300 hr*pg/mL, at least about 2400 hr*pg/mL, at least about 2500 hr*pg/mL, at least about 2600 hr*pg/mL, at least about 2700 hr*pg/mL, at least about 2800 hr*pg/mL, at least about 2900 hr*pg/mL, at least about 3000 hr*pg/mL, at least about 3100 hr*pg/mL, at least about 3200 hr*pg/mL, at least about 3300 hr*pg/mL, at least about 3400 hr*pg/mL, or at least about 3500 hr*pg/mL. In one embodiment, the $AUC_{0\text{-}last}$ is measured after a single dose administration of about 1 mg to about 250 mg of betahistine or a pharmaceutically acceptable salt.

In one embodiment, the $AUC_{0\text{-}last}$ of betahistine in human plasma concentration after single dose administration of the intranasal pharmaceutical composition of the present disclosure is at least about 0.05 hr*ng/mL, at least about 0.1 hr*ng/mL, at least about 0.2 hr*ng/mL, at least about 0.25 hr*ng/mL, at least about 0.3 hr*ng/mL, at least about 0.4 hr*ng/mL, at least about 0.5 hr*ng/mL, at least about 0.6 hr*ng/mL, at least about 0.7 hr*ng/mL, at least about 0.8 hr*ng/mL, at least about 0.9 hr*ng/mL, at least about 1.0 hr*ng/mL, at least about 1.1 hr*ng/mL, at least about 1.2 hr*ng/mL, at least about 1.3 hr*ng/mL, at least about 1.4 hr*ng/mL, at least about 1.5 hr*ng/mL, at least about 1.6 hr*ng/mL, at least about 1.7 hr*ng/mL, at least about 1.8 hr*ng/mL, at least about 1.9 hr*ng/mL, at least about 2.0 hr*ng/mL, at least about 2.1 hr*ng/mL, at least about 2.2 hr*ng/mL, at least about 2.3 hr*ng/mL, at least about 2.4 hr*ng/mL, at least about 2.5 hr*ng/mL, at least about 2.6 hr*ng/mL, at least about 2.7 hr*ng/mL, at least about 2.8 hr*ng/mL, at least about 2.9 hr*ng/mL, at least about 3.0 hr*ng/mL, at least about 3.1 hr*ng/mL, at least about 3.2 hr*ng/mL, at least about 3.3 hr*ng/mL, at least about 3.4 hr*ng/mL, at least about 3.5 hr*ng/mL, at least about 3.6 hr*ng/mL, at least about 3.7 hr*ng/mL, at least about 3.8 hr*ng/mL, at least about 3.9 hr*ng/mL, at least about 4.0 hr*ng/mL. In one embodiment, the $AUC_{0\text{-}last}$ of betahistine in human plasma concentration after single dose administration of the intranasal pharmaceutical composition of the present disclosure is at least about 1.5 hr*ng/mL or at least about 3.0 hr*ng/mL.

In one embodiment, the $AUC_{0\text{-}last}$ of betahistine in human plasma concentration is determined after single dose administration of the intranasal pharmaceutical composition comprising about 1 mg to about 200 mg of betahistine or a pharmaceutically acceptable salt. In one embodiment, the $AUC_{0\text{-}last}$ is determined after a single intranasal dose of about 5 mg, 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg of betahistine or a pharmaceutically acceptable salt. In one embodiment, the $AUC_{0\text{-}last}$ is determined after a single intranasal dose administration of about 20 mg or about 40 mg of betahistine or a pharmaceutically acceptable salt. In another embodiment, the $AUC_{0\text{-}last}$ is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In various embodiments, the $AUC_{0\text{-}last}$ ranges from about 80%-125% of about 210 pg*hr/mL for a 5 mg betahistine dose administered intranasally; about 80%-125% of about 500 pg*hr/mL for a 10 mg betahistine dose administered intranasally; about 80%-125% of about 1600 pg*hr/mL for a 20 mg betahistine dose administered intranasally; and about 80%-125% of about 3500 pg*hr/mL for a 40 mg betahistine dose administered intranasally.

In some embodiments, the $AUC_{0\text{-}last}$ for a 5 mg betahistine dose, administered intranasally, ranges from about 80% to about 125% of about 200 pg*hr/mL, 300 pg*hr/mL, 400 pg*hr/mL, 500 pg*hr/mL, 600 pg*hr/mL, 700 pg*hr/mL, 800 pg*hr/mL, 900 pg*hr/mL, 1000 pg*hr/mL, 1100 pg*hr/mL, 1200 pg*hr/mL, 1300 pg*hr/mL, 1400 pg*hr/mL, or 1500 pg*hr/mL.

In some other embodiments, the $AUC_{0\text{-}last}$ for a 5 mg betahistine dose, administered intranasally, ranges from about 80% to about 125% of about 200 to about 500 pg*hr/mL, about 200 to about 600 pg*hr/mL, about 300 to about 700 pg*hr/mL, about 400 to about 800 pg*hr/mL, about 500 to about 1000 pg*hr/mL, about 600 to about 1100 pg*hr/mL, about 750 to about 1250 pg*hr/mL, or about 800 to about 1400 pg*hr/mL.

In some embodiments, the $AUC_{0\text{-}last}$ for a 10 mg betahistine dose, administered intranasally, ranges from about 80% to about 125% of about 500 pg*hr/mL, 600 pg*hr/mL, 700 pg*hr/mL, 800 pg*hr/mL, 900 pg*hr/mL, 1000 pg*hr/mL, 1100 pg*hr/mL, 1200 pg*hr/mL, 1300 pg*hr/mL, 1400 pg*hr/mL, or 1500 pg*hr/mL.

In some other embodiments, the $AUC_{0\text{-}last}$ for a 10 mg betahistine dose, administered intranasally, ranges from about 80% to about 125% of about 400 to about 800 pg*hr/mL, about 500 to about 800 pg*hr/mL, about 500 to about 900 pg*hr/mL, about 500 to about 1000 pg*hr/mL, about 500 to about 1200 pg*hr/mL, about 600 to about 1000 pg*hr/mL, about 600 to about 1100 pg*hr/mL, about 600 to about 1200 pg*hr/mL, about 700 to about 1100 pg*hr/mL, about 700 to about 1200 pg*hr/mL, about 800 to about 1300 pg*hr/mL, about 800 to about 1200 pg*hr/mL, or about 900 to about 1200 pg*hr/mL.

In some embodiments, the $AUC_{0\text{-}last}$ for a 20 mg betahistine dose, administered intranasally, ranges from about 80% to about 125% of about 1500 pg*hr/mL, 1600 pg*hr/mL, 1700 pg*hr/mL, 1800 pg*hr/mL, 1900 pg*hr/mL, 2000 pg*hr/mL, 2100 pg*hr/mL, 2200 pg*hr/mL, 2300 pg*hr/mL, 2400 pg*hr/mL, 2500 pg*hr/mL, 2600 pg*hr/mL, 2700 pg*hr/mL, 2800 pg*hr/mL, 2900 pg*hr/mL, or 3000 pg*hr/mL.

In some other embodiments, the $AUC_{0\text{-}last}$ for a 20 mg betahistine dose, administered intranasally, ranges from about 80% to about 125% of about 1500 to about 2000 pg*hr/mL, about 1500 to about 2200 pg*hr/mL, about 1600 to about 2100 pg*hr/mL, about 1700 to about 2200 pg*hr/mL, about 1700 to about 2400 pg*hr/mL, about 1800 to about 2400 pg*hr/mL, about 1900 to about 2500 pg*hr/mL, about 2000 to about 2500 pg*hr/mL, about 2100 to about 2700 pg*hr/mL, or about 2200 to about 2900 pg*hr/mL.

In some embodiments, the $AUC_{0-last}$ for a 40 mg betahistine dose, administered intranasally, ranges from about 80% to about 125% of about 3300 pg*hr/mL, 3400 pg*hr/mL, 3500 pg*hr/mL, 3600 pg*hr/mL, 3700 pg*hr/mL, 3800 pg*hr/mL, 3900 pg*hr/mL, 4000 pg*hr/mL, 4100 pg*hr/mL, 4250 pg*hr/mL, 4500 pg*hr/mL, 4750 pg*hr/mL, 5000 pg*hr/mL, 5250 pg*hr/mL, 5500 pg*hr/mL, 5750 pg*hr/mL, 6000 pg*hr/mL, 6250 pg*hr/mL, 6500 pg*hr/mL, or 7000 pg*hr/mL.

In some other embodiments, the $AUC_{0-last}$ for a 40 mg betahistine dose, administered intranasally, ranges from about 80% to about 125% of about 3300 to about 3800 pg*hr/mL, about 3300 to about 4000 pg*hr/mL, about 3300 to about 4200 pg*hr/mL, about 3300 to about 4500 pg*hr/mL, about 3500 to about 4000 pg*hr/mL, about 3500 to about 4200 pg*hr/mL, about 3500 to about 4500 pg*hr/mL, about 3750 to about 4250 pg*hr/mL, about 3750 to about 4500 pg*hr/mL, about 3750 to about 4750 pg*hr/mL, about 4000 to about 5000 pg*hr/mL, or about 4000 to about 5500 pg*hr/mL.

In some embodiments, the $AUC_{0-last}$ for a 60 mg betahistine dose, administered intranasally, ranges from about 80% to about 125% of about 5300 pg*hr/mL, 5400 pg*hr/mL, 5500 pg*hr/mL, about 5750 pg*hr/mL, 6000 pg*hr/mL, 6250 pg*hr/mL, 6500 pg*hr/mL, 6750 pg*hr/mL, 7000 pg*hr/mL, 7250 pg*hr/mL, 7500 pg*hr/mL, 7750 pg*hr/mL, or about 8000 pg*hr/mL.

In some other embodiments, the $AUC_{0-last}$ for a 60 mg betahistine dose, administered intranasally, ranges from about 80% to about 125% of about 5300 to about 5800 pg*hr/mL, about 5400 to about 5900 pg*hr/mL, about 5500 to about 6000 pg*hr/mL, about 5400 to about 6200 pg*hr/mL, about 5500 to about 6400 pg*hr/mL, about 5500 to about 6700 pg*hr/mL, about 5500 to about 6900 pg*hr/mL, about 5700 to about 6300 pg*hr/mL, about 5700 to about 6500 pg*hr/mL, about 5700 to about 6700 pg*hr/mL, about 5900 to about 6500 pg*hr/mL, about 5900 to about 6700 pg*hr/mL, about 6000 to about 7250 pg*hr/mL, about 6000 to about 7000 pg*hr/mL, about 6000 to about 7500 pg*hr/mL.

In some embodiments, the $AUC_{0-last}$ for a 80 mg betahistine dose, administered intranasally, ranges from about 80% to about 125% of about 7500 pg*hr/mL, 7750 pg*hr/mL, 8000 pg*hr/mL, 8250 pg*hr/mL, 8500 pg*hr/mL, 8750 pg*hr/mL, 9000 pg*hr/mL, 9250 pg*hr/mL, 9500 pg*hr/mL, 9750 pg*hr/mL, or 10000 pg*hr/mL.

In some other embodiments, the $AUC_{0-last}$ for a 80 mg betahistine dose, administered intranasally, ranges from about 80% to about 125% of about 7300 to about 8000 pg*hr/mL, about 7500 to about 8200 pg*hr/mL, about 7500 to about 8000 pg*hr/mL, about 7500 to about 8500 pg*hr/mL, about 7750 to about 8500 pg*hr/mL, about 7750 to about 8750 pg*hr/mL, about 8000 to about 8500 pg*hr/mL, about 8000 to about 8750 pg*hr/mL, about 8000 to about 9000 pg*hr/mL, about 8250 to about 9000 pg*hr/mL, about 8250 to about 8750 pg*hr/mL, about 8250 to about 9250 pg*hr/mL, about 8500 to about 9500 pg*hr/mL, or about 8500 to about 9000 pg*hr/mL.

In one embodiment, the pharmaceutical composition of the present disclosure provides an $AUC_{0-inf}$ of betahistine in human plasma concentration after single dose administration of the pharmaceutical composition of the present disclosure of at least about 100 hr*pg/mL, at least about 200 hr*pg/mL, at least about 250 hr*pg/mL, at least about 300 hr*pg/mL, at least about 400 hr*pg/mL, at least about 500 hr*pg/mL, at least about 600 hr*pg/mL, at least about 700 hr*pg/mL, at least about 800 hr*pg/mL, at least about 900 hr*pg/mL, at least about 1000 hr*pg/mL, at least about 1100 hr*pg/mL, at least about 1200 hr*pg/mL, at least about 1300 hr*pg/mL, at least about 1400 hr*pg/mL, at least about 1500 hr*pg/mL, at least about 1600 hr*pg/mL, at least about 1700 hr*pg/mL, at least about 1800 hr*pg/mL, at least about 1900 hr*pg/mL, at least about 2000 hr*pg/mL, at least about 2100 hr*pg/mL, at least about 2200 hr*pg/mL, at least about 2300 hr*pg/mL, at least about 2400 hr*pg/mL, at least about 2500 hr*pg/mL, at least about 2600 hr*pg/mL, at least about 2700 hr*pg/mL, at least about 2800 hr*pg/mL, at least about 2900 hr*pg/mL, at least about 3000 hr*pg/mL, at least about 3100 hr*pg/mL, at least about 3200 hr*pg/mL, at least about 3300 hr*pg/mL, at least about 3400 hr*pg/mL, or at least about 3500 hr*pg/mL. In one embodiment, the $AUC_{0-inf}$ is measured after a single dose administration of about 1 mg to about 250 mg of betahistine or a pharmaceutically acceptable salt.

In one embodiment, the $AUC_{0-inf}$ of betahistine in human plasma concentration after single dose administration of the intranasal pharmaceutical composition of the present disclosure is at least about 0.1 hr*ng/mL, at least about 0.2 hr*ng/mL, at least about 0.25 hr*ng/mL, at least about 0.3 hr*ng/mL, at least about 0.4 hr*ng/mL, at least about 0.5 hr*ng/mL, at least about 0.6 hr*ng/mL, at least about 0.7 hr*ng/mL, at least about 0.8 hr*ng/mL, at least about 0.9 hr*ng/mL, at least about 1.0 hr*ng/mL, at least about 1.1 hr*ng/mL, at least about 1.2 hr*ng/mL, at least about 1.3 hr*ng/mL, at least about 1.4 hr*ng/mL, at least about 1.5 hr*ng/mL, at least about 1.6 hr*ng/mL, at least about 1.7 hr*ng/mL, at least about 1.8 hr*ng/mL, at least about 1.9 hr*ng/mL, at least about 2.0 hr*ng/mL, at least about 2.1 hr*ng/mL, at least about 2.2 hr*ng/mL, at least about 2.3 hr*ng/mL, at least about 2.4 hr*ng/mL, at least about 2.5 hr*ng/mL, at least about 2.6 hr*ng/mL, at least about 2.7 hr*ng/mL, at least about 2.8 hr*ng/mL, at least about 2.9 hr*ng/mL, at least about 3.0 hr*ng/mL, at least about 3.1 hr*ng/mL, at least about 3.2 hr*ng/mL, at least about 3.3 hr*ng/mL, at least about 3.4 hr*ng/mL, at least about 3.5 hr*ng/mL, at least about 3.6 hr*ng/mL, at least about 3.7 hr*ng/mL, at least about 3.8 hr*ng/mL, at least about 3.9 hr*ng/mL, at least about 4.0 hr*ng/mL. In one embodiment, the $AUC_{0-inf}$ of betahistine in human plasma concentration after single dose administration of the intranasal pharmaceutical composition of the present disclosure is at least about 1.5 hr*ng/mL or at least about 3.0 hr*ng/mL.

In one embodiment, the $AUC_{0-inf}$ of betahistine in human plasma concentration is determined after single dose administration of the intranasal pharmaceutical composition comprising about 1 mg to about 200 mg of betahistine or a pharmaceutically acceptable salt. In one embodiment, the $AUC_{0-inf}$ is determined after a single intranasal dose of about 5 mg, 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg of betahistine or a pharmaceutically acceptable salt. In one embodiment, $AUC_{0-inf}$ is determined after a single intranasal dose administration of about 20 mg or about 40 mg of betahistine or a pharmaceutically acceptable salt. In another embodiment, the $AUC_{0-inf}$ is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In various embodiments, the $AUC_{0-inf}$ of betahistine ranges from about 80%-125% of about 275 pg*hr/mL for a 5 mg betahistine dose administered intranasally; about 80%-125% of about 700 pg*hr/mL for a 10 mg betahistine dose administered intranasally; about 80%-125% of about 1630 pg*hr/mL for a 20 mg betahistine dose administered intranasally; and about 80%-125% of about 2940 pg*hr/mL for a 40 mg betahistine dose administered intranasally.

In some embodiments, the $AUC_{0-inf}$ for a 5 mg betahistine dose, administered intranasally, ranges from about 80% to about 125% of about 250 pg*hr/mL, 275 pg*hr/mL, 300 pg*hr/mL, 350 pg*hr/mL, 400 pg*hr/mL, 450 pg*hr/mL, 500 pg*hr/mL, 600 pg*hr/mL, 700 pg*hr/mL, 800 pg*hr/mL, 900 pg*hr/mL, or 1000 pg*hr/mL.

In some other embodiments, the $AUC_{0-inf}$ for a 5 mg betahistine dose, administered intranasally, ranges from about 80% to about 125% of about 250 to about 350 pg*hr/mL, about 250 to about 500 pg*hr/mL, about 275 to about 375 pg*hr/mL, about 275 to about 475 pg*hr/mL, about 275 to about 575 pg*hr/mL, about 250 to 850 pg*hr/mL, about 300 to about 800 pg*hr/mL, about 300 to about 700 pg*hr/mL, about 400 to about 800 pg*hr/mL, about 500 to about 1000 pg*hr/mL, about 750 to about 1250 pg*hr/mL, or about 750 to about 1500 pg*hr/mL.

In some embodiments, the $AUC_{0-inf}$ for a 10 mg betahistine dose, administered intranasally, ranges from about 80% to about 125% of about 650 pg*hr/mL, about 700 pg*hr/mL, about 800 pg*hr/mL, about 900 pg*hr/mL, about 1000 pg*hr/mL, about 1250 pg*hr/mL, about about 1500 pg*hr/mL, about 1750 pg*hr/mL, or about 2000 pg*hr/mL.

In some other embodiments, the $AUC_{0-inf}$ for a 10 mg betahistine dose, administered intranasally, ranges from about 80% to about 125% of about 650 to about 1000 pg*hr/mL, about 650 to about 1250 pg*hr/mL, about 700 to about 1400 pg*hr/mL, about 700 to about 1200 pg*hr/mL, about 700 to 1000 pg*hr/mL, about 800 to about 1200 pg*hr/mL, about 800 to about 1400 pg*hr/mL, about 800 to about 1600 pg*hr/mL, about 1000 to about 1500 pg*hr/mL, or about 1000 to about 2000 pg*hr/mL.

In some embodiments, the $AUC_{0-inf}$ for a 20 mg betahistine dose, administered intranasally, ranges from about 80% to about 125% of about 1600 pg*hr/mL, about 1700 pg*hr/mL, about 1800 pg*hr/mL, about 1900 pg*hr/mL, about 2000 pg*hr/mL, about 2250 pg*hr/mL, about 2500 pg*hr/mL, about 2750 pg*hr/mL, about 3000 pg*hr/mL, or about 3500 pg*hr/mL.

In some other embodiments, the $AUC_{0-inf}$ for a 20 mg betahistine dose, administered intranasally, ranges from about 80% to about 125% of about 1600 to about 2000 pg*hr/mL, about 1600 to about 2200 pg*hr/mL, about 1600 to about 2400 pg*hr/mL, about 1600 to about 2600 pg*hr/mL, about 1800 to about 2400 pg*hr/mL, about 1800 to about 2600 pg*hr/mL, about 1800 to about 2800 pg*hr/mL, about 2000 to about 3000 pg*hr/mL, about 2000 to about 2500 pg*hr/mL, about 2000 to about 2800 pg*hr/mL, about 2250 to about 3250 pg*hr/mL, about 2250 to about 3000 pg*hr/mL, about 2500 to about 3500 pg*hr/mL, or about 2500 to about 3000 pg*hr/mL.

In some embodiments, the $AUC_{0-inf}$ for a 40 mg betahistine dose, administered intranasally, ranges from about 80% to about 125% of about 2800 pg*hr/mL, about 2900 pg*hr/mL, about 2950 pg*hr/mL, about 3000 pg*hr/mL, about 3100 pg*hr/mL, about 3200 pg*hr/mL, about 3300 pg*hr/mL, about 3400 pg*hr/mL, about 3500 pg*hr/mL, about 3600 pg*hr/mL, about 3700 pg*hr/mL, about 3800 pg*hr/mL, about 3900 pg*hr/mL, about 4000 pg*hr/mL, about 4250 pg*hr/mL, about 4500 pg*hr/mL, about 4750 pg*hr/mL, about 5000 pg*hr/mL, about 5250 pg*hr/mL, about 5500 pg*hr/mL, about 5750 pg*hr/mL, or about 6000 pg*hr/mL.

In some other embodiments, the $AUC_{0-inf}$ for a 40 mg betahistine dose, administered intranasally, ranges from about 80% to about 125% of about 2800 to about 3300 pg*hr/mL, about 2800 to about 3500 pg*hr/mL, about 2800 to about 3800 pg*hr/mL, about 3000 to about 3500 pg*hr/mL, about 3500 to about 3750 pg*hr/mL, about 3000 to about 4000 pg*hr/mL, about 3250 to about 4250 pg*hr/mL, about 3250 to about 4500 pg*hr/mL, about 3500 to about 4500 pg*hr/mL, about 3500 to about 4000 pg*hr/mL, about 3750 to about 4750 pg*hr/mL, about 3750 to about 4500 pg*hr/mL, about 4000 to about 5000 pg*hr/mL, about 4500 to about 5500 pg*hr/mL, or about 5000 to about 6000 pg*hr/mL.

In some embodiments, the $AUC_{0-inf}$ for a 60 mg betahistine dose, administered intranasally, ranges from about 80% to about 125% of about 5300 pg*hr/mL, 5400 pg*hr/mL, 5500 pg*hr/mL, about 5750 pg*hr/mL, 6000 pg*hr/mL, 6250 pg*hr/mL, 6500 pg*hr/mL, 6750 pg*hr/mL, 7000 pg*hr/mL, 7250 pg*hr/mL, 7500 pg*hr/mL, 7750 pg*hr/mL, or about 8000 pg*hr/mL.

In some other embodiments, the $AUC_{0-inf}$ for a 60 mg betahistine dose, administered intranasally, ranges from about 80% to about 125% of about 5300 to about 5800 pg*hr/mL, about 5400 to about 5900 pg*hr/mL, about 5500 to about 6000 pg*hr/mL, about 5400 to about 6200 pg*hr/mL, about 5500 to about 6400 pg*hr/mL, about 5500 to about 6700 pg*hr/mL, about 5500 to about 6900 pg*hr/mL, about 5700 to about 6300 pg*hr/mL, about 5700 to about 6500 pg*hr/mL, about 5700 to about 6700 pg*hr/mL, about 5900 to about 6500 pg*hr/mL, about 5900 to about 6700 pg*hr/mL, about 6000 to about 7250 pg*hr/mL, about 6000 to about 7000 pg*hr/mL, about 6000 to about 7500 pg*hr/mL.

In some embodiments, the $AUC_{0-inf}$ for a 80 mg betahistine dose, administered intranasally, ranges from about 80% to about 125% of about 7500 pg*hr/mL, 7750 pg*hr/mL, 8000 pg*hr/mL, 8250 pg*hr/mL, 8500 pg*hr/mL, 8750 pg*hr/mL, 9000 pg*hr/mL, 9250 pg*hr/mL, 9500 pg*hr/mL, 9750 pg*hr/mL, or 10000 pg*hr/mL.

In some other embodiments, the $AUC_{0-inf}$ for a 80 mg betahistine dose, administered intranasally, ranges from about 80% to about 125% of about 7300 to about 8000 pg*hr/mL, about 7500 to about 8200 pg*hr/mL, about 7500 to about 8000 pg*hr/mL, about 7500 to about 8500 pg*hr/mL, about 7750 to about 8500 pg*hr/mL, about 7750 to about 8750 pg*hr/mL, about 8000 to about 8500 pg*hr/mL, about 8000 to about 8750 pg*hr/mL, about 8000 to about 9000 pg*hr/mL, about 8250 to about 9000 pg*hr/mL, about 8250 to about 8750 pg*hr/mL, about 8250 to about 9250 pg*hr/mL, about 8500 to about 9500 pg*hr/mL, or about 8500 to about 9000 pg*hr/mL.

In one embodiment, absolute bioavailability (% F) of betahistine administered intranasally is about 10%, 15%, 20%, 25%, 30%, 35%, 40%, 45%, 50%, 55%, 60%, 65%, 70%, 75%, 80%, 85%, or 90%. In one embodiment, absolute bioavailability (% F) of betahistine administered intranasally is about 30-80%, about 25-75%, about 20-60%, about 10-50%, about 30-60%, about 40-60%, about 40-70%, about 40-80%, or about 50-80%.

In one embodiment, the relative bioavailability ($F_{rel}$) for 5 mg betahistine administered intranasally is about 10, 11, 12, 13, 14, 15, 16, 17, 18, 19, 20, 21, 22, 23, 24, or 25 times the oral bioavailability. In one embodiment, the relative bioavailability for 10 mg betahistine administered intranasally is about 15, 16, 17, 18, 19, 20, 21, 22, 23, 24, 25, 26, 27, 28, or 29 times the oral bioavailability. In one embodiment, the relative bioavailability for 20 mg betahistine administered intranasally is about 27, 28, 29, 30, 31, 32, 33, 34, 35, 36, 37, 38, 39, 40, 41, or 42 times the oral bioavailability. In one embodiment, the relative bioavailability for 40 mg betahistine administered intranasally is about 36, 37, 38, 39, 40, 41, 42, 43, 44, 45, or 46 times the oral bioavailability. In one embodiment, the relative bioavailability for 60 mg betahistine administered intranasally is about 45, 46, 47, 48, 49, 50, 51, 52, 53, 54, 55, 56, 57, 58, 59, 60, 61, 62, 63, 64, 65, 66, 67, 68, 69, or 70 times the oral bioavailability. In one embodiment, the relative bioavailability for 80 mg betahistine administered intranasally is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 times the oral bioavailability. In one embodiment, the relative bioavailability for 100 mg betahistine administered intranasally is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times the oral bioavailability.

In one embodiment, the relative bioavailability for betahistine administered intranasally is up to about 10-25, about 15-30, about 20-40, about 20-30, about 20-50, about 25-40, about 25-45, about 25-50, about 15-45, about 30-60 times the oral bioavailability.

In one embodiment, the $t_{1/2}$ (apparent half-life) of betahistine determined based on a single dose administration of the pharmaceutical composition of the present disclosure is about 0.07 h or greater, about 0.08 h or greater, about 0.09 h or greater, about 0.1 h or greater, about 0.2 h or greater, about 0.3 h or greater, about 0.4 h or greater, about 0.5 h or greater, about 0.6 h or greater, about 0.6 h or greater, about 0.8 h or greater, about 0.9 h or greater, or about 1.0 h or greater. In one embodiment, the $t_{1/2}$ is determined based on a single dose administration of about 1 mg to about 250 mg of betahistine or a pharmaceutically acceptable salt. In one embodiment, the $t_{1/2}$ is determined based on a single dose administration of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the $t_{1/2}$ (apparent half-life) of betahistine determined based on a single dose administration of the intranasal pharmaceutical composition of the present disclosure is about 0.07 h or greater, about 0.08 h or greater, about 0.09 h or greater, about 0.1 h or greater, about 0.2 h or greater, about 0.3 h or greater, about 0.4 h or greater, about 0.5 h or greater, about 0.6 h or greater, about 0.6 h or greater, about 0.8 h or greater, about 0.9 h or greater, or about 1.0 h or greater. In one embodiment, the $t_{1/2}$ of betahistine determined based on a single dose administration of the intranasal pharmaceutical composition of the present disclosure is about 0.4 h or greater or about 0.8 h or greater. In one embodiment, the $t_{1/2}$ of betahistine determined based on a single dose of the intranasal pharmaceutical composition of the present disclosure is about 0.5 h or about 0.9 h.

In one embodiment, the $t_{1/2}$ is determined based on a single intranasal dose administration of about 1 mg to about 200 mg of betahistine or a pharmaceutically acceptable salt. In one embodiment, the $t_{1/2}$ is determined based on a single intranasal dose administration of about 5 mg, 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg of betahistine or a pharmaceutically acceptable salt. In one embodiment, the $t_{1/2}$ is determined based on a single intranasal dose administration of about 20 mg or about 40 mg of betahistine or a pharmaceutically acceptable salt. In another embodiment, the $t_{1/2}$ is determined based on a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the pharmaceutical composition of the present disclosure provides a detectable $C_{max}$ of 2-PAA (2-pyridylacetic acid) in human plasma concentration after single dose administration of the pharmaceutical composition of the present disclosure. In one embodiment, the $C_{max}$ of 2-PAA in human plasma concentration after single dose administration of the pharmaceutical composition of the present disclosure is at least about 15 ng/mL or at least about 50 ng/mL. In one embodiment, the $C_{max}$ of 2-PAA is measured after a single dose administration of about 1 mg to about 250 mg of betahistine or a pharmaceutically acceptable salt. In one embodiment, the $C_{max}$ of 2-PAA is measured after a single dose administration of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt. In other embodiments, the $C_{max}$ of 2-PAA for a 5 mg betahistine dose, administered intranasally, ranges from about 80% to about 125% of about 65 ng/ml; about 80% to about 125% of about 150 ng/ml for a 10 mg betahistine dose, administered intranasally; about 80% to about 125% of about 370 ng/ml for a 20 mg betahistine dose, administered intranasally; and about 80% to about 125% of about 520 ng/ml for a 40 mg betahistine days, administered intranasally. In other embodiments, the $C_{max}$ of 2-PAA for a 5 mg betahistine dose, administered intranasally, ranges from about 80% to about 125% of about 16 to about 95 ng/ml; about 80% to about 125% of about 115 ng/ml to about 175 ng/ml for a 10 mg betahistine dose, administered intranasally; about 80% to about 125% of about 250 to about 430 g/ml for a 20 mg betahistine dose, administered intranasally; and about 80% to about 125% of about 290 to about 690 ng/ml for a 40 mg betahistine days, administered intranasally.

In one embodiment, the $C_{max}$ of 2-PAA in human plasma concentration after single dose administration of the intranasal pharmaceutical composition of the present disclosure is at least about 15 ng/mL or at least about 50 ng/mL. In one embodiment, the $C_{max}$ of 2-PAA in human plasma concentration after single dose administration of the intranasal pharmaceutical composition of the present disclosure is at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 150 ng/mL, at least about 200 ng/mL, at least about 250 ng/mL, at least about 300 ng/mL, at least about 400 ng/mL, at least about 450 ng/mL, at least about 500 ng/mL, or at least about 550 ng/mL.

In one embodiment, the $C_{max}$ of 2-PAA in human plasma concentration after single dose administration of the intranasal pharmaceutical composition of the present disclosure is at least about 60 ng/mL. In one embodiment, the $C_{max}$ of 2-PAA in human plasma concentration is measured after single dose administration of the intranasal pharmaceutical composition comprising about 1 mg to about 200 mg of betahistine or a pharmaceutically acceptable salt. In one embodiment, the $C_{max}$ of 2-PAA is measured after a single intranasal dose administration of about 5 mg to about 100 mg of betahistine or a pharmaceutically acceptable salt. In one embodiment, the $C_{max}$ of 2-PAA is measured after a single intranasal dose administration of about 20 mg or about 40 mg of betahistine or a pharmaceutically acceptable salt. In another embodiment, the $C_{max}$ of 2-PAA is measured after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the pharmaceutical composition of the present disclosure provides a $t_{max}$ of 2-PAA in human plasma concentration after single dose administration of the pharmaceutical composition of the present disclosure. In one embodiment, the $t_{max}$ of 2-PAA in human plasma concentration after single dose administration of the pharmaceutical composition of the present disclosure is about 0.6 h or greater, about 0.7 h or greater, about 0.8 h or greater, about 0.9 h or greater, about 1 h or greater, about 1.1 h or greater, about 1.2 h or greater, about 1.25 h or greater, about 1.3 h or greater, about 1.4 h or greater, or about 1.5 h or greater. In one embodiment, the $t_{max}$ is measured after a single dose administration of about 1 mg to about 250 mg of betahistine or a pharmaceutically acceptable salt. In one embodiment, the $t_{max}$ is measured after a single dose of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the $t_{max}$ of 2-PAA in human plasma concentration after single dose administration of the intranasal pharmaceutical composition of the present disclosure is about 1.0 h. In one embodiment, the $t_{max}$ of 2-PAA in human plasma concentration after single dose administration of the intranasal pharmaceutical composition of the present disclosure is about 0.9 h or greater, about 1.0 h or greater, about 1.1 h or greater, or about 1.2 h or greater. In one embodiment, the $t_{max}$ of 2-PAA in human plasma concentration is determined after single dose administration of the intranasal pharmaceutical composition comprising about 1 mg to about 200 mg of betahistine or a pharmaceutically acceptable salt. In one embodiment, the $t_{max}$ of 2-PAA is determined after a single intranasal dose administration of about 5 mg to about 100 mg, of betahistine or a pharmaceutically acceptable salt. In one embodiment, the $t_{max}$ of 2-PAA is determined after a single intranasal dose administration of about 20 mg or about 40 mg of betahistine or a pharmaceutically acceptable salt. In another embodiment, the $t_{max}$ of 2-PAA is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the pharmaceutical composition of the present disclosure provides an $AUC_{0\text{-}last}$ of 2-PAA in human plasma concentration after single dose administration of the pharmaceutical composition of the present disclosure of at least about 100 hr*ng/mL, at least about 200 hr*ng/mL, at least about 250 hr*ng/mL, at least about 300 hr*ng/mL, at least about 400 hr*ng/mL, at least about 500 hr*ng/mL, at least about 600 hr*ng/mL, at least about 700 hr*ng/mL, at least about 800 hr*ng/mL, at least about 900 hr*ng/mL, at least about 1000 hr*ng/mL, at least about 1100 hr*ng/mL, at least about 1200 hr*ng/mL, at least about 1300 hr*ng/mL, at least about 1400 hr*ng/mL, at least about 1500 hr*ng/mL, at least about 1600 hr*ng/mL, at least about 1700 hr*ng/mL, at least about 1800 hr*ng/mL, at least about 1900 hr*ng/mL, at least about 2000 hr*ng/mL, at least about 2100 hr*ng/mL, at least about 2200 hr*ng/mL, at least about 2300 hr*ng/mL, at least about 2400 hr*ng/mL, at least about 2500 hr*ng/mL, at least about 2600 hr*ng/mL, at least about 2700 hr*ng/mL, at least about 2800 hr*ng/mL, at least about 2900 hr*ng/mL, or at least about 3000 hr*ng/mL, at least about 3100 hr*ng/mL, at least about 3200 hr*ng/mL, at least about 3300 hr*ng/mL, at least about 3400 hr*ng/mL, or at least about 3500 hr*ng/mL. In one embodiment, the $AUC_{0\text{-}last}$ of 2-PAA is measured after a single dose administration of about 1 mg to about 200 mg of betahistine or a pharmaceutically acceptable salt.

In one embodiment, the $AUC_{0\text{-}last}$ of 2-PAA in human plasma concentration is determined after single dose administration of the intranasal pharmaceutical composition comprising about 1 mg to about 200 mg of betahistine or a pharmaceutically acceptable salt. In one embodiment, the $AUC_{0\text{-}last}$ of 2-PAA is determined after a single intranasal dose of about 5 mg to about 100 mg of betahistine or a pharmaceutically acceptable salt. In one embodiment, the $AUC_{0\text{-}last}$ of 2-PAA is determined after a single intranasal dose administration of about 20 mg or about 40 mg of betahistine or a pharmaceutically acceptable salt. In another embodiment, the $AUC_{0\text{-}last}$ of 2-PAA is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In various embodiments, the $AUC_{0\text{-}last}$ of 2-PAA ranges from about 80%-125% of about 390 ng·hr/mL for a 5 mg betahistine dose administered intranasally; about 80%-125% of about 730 ng·hr/mL for a 10 mg betahistine dose administered intranasally; about 80%-125% of about 2000 ng·hr/mL for a 20 mg betahistine dose administered intranasally; and about 80%-125% of about 2800 ng·hr/mL for a 40 mg betahistine dose administered intranasally.

In one embodiment, the pharmaceutical composition of the present disclosure provides an $AUC_{0\text{-}inf}$ of 2-PAA in human plasma concentration after single dose administration of the pharmaceutical composition of the present disclosure of at least about 100 hr*ng/mL, at least about 200 hr*ng/mL, at least about 250 hr*ng/mL, at least about 300 hr*ng/mL, at least about 400 hr*ng/mL, at least about 500 hr*ng/mL, at least about 600 hr*ng/mL, at least about 700 hr*ng/mL, at least about 800 hr*ng/mL, at least about 900 hr*ng/mL, at least about 1000 hr*ng/mL, at least about 1100 hr*ng/mL, at least about 1200 hr*ng/mL, at least about 1300 hr*ng/mL, at least about 1400 hr*ng/mL, at least about 1500 hr*ng/mL, at least about 1600 hr*ng/mL, at least about 1700 hr*ng/mL, at least about 1800 hr*ng/mL, at least about 1900 hr*ng/mL, at least about 2000 hr*ng/mL, at least about 2100 hr*ng/mL, at least about 2200 hr*ng/mL, at least about 2300 hr*ng/mL, at least about 2400 hr*ng/mL, at least about 2500 hr*ng/mL, at least about 2600 hr*ng/mL, at least about 2700 hr*ng/mL, at least about 2800 hr*ng/mL, at least about 2900 hr*ng/mL, at least about 3000 hr*ng/mL, at least about 3100 hr*ng/mL, at least about 3200 hr*ng/mL, at least about 3300 hr*ng/mL, at least about 3400 hr*ng/mL, or at least about 3500 hr*ng/mL. In one embodiment, the $AUC_{0\text{-}inf}$ of 2-PAA is measured after a single dose administration of about 1 mg to about 200 mg of betahistine or a pharmaceutically acceptable salt.

In one embodiment, the $AUC_{0\text{-}inf}$ of 2-PAA in human plasma concentration is determined after single dose administration of the intranasal pharmaceutical composition comprising about 1 mg to about 200 mg of betahistine or a pharmaceutically acceptable salt. In one embodiment, the $AUC_{0\text{-}inf}$ of 2-PAA is determined after a single intranasal dose of about 5 mg to about 100 mg of betahistine or a pharmaceutically acceptable salt. In one embodiment, the $AUC_{0\text{-}inf}$ of 2-PAA is determined after a single intranasal dose administration of about 20 mg or about 40 mg of betahistine or a pharmaceutically acceptable salt. In another embodiment, the $AUC_{0\text{-}inf}$ of 2-PAA is determined after a single intranasal dose administration of about 5 mg, about 10 mg, about 15 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In various embodiments, the $AUC_{0\text{-}inf}$ of 2-PAA ranges from about 80%-125% of about 430 ng·hr/mL for a 5 mg betahistine dose administered intranasally; about 80%-125% of about 760 ng·hr/mL for a 10 mg betahistine dose administered intranasally; about 80%-125% of about 2000 ng·hr/mL for a 20 mg betahistine dose administered intranasally; and about 80%-125% of about 2900 ng·hr/mL for a 40 mg betahistine dose administered intranasally.

In one embodiment, the $t_{1/2}$ (apparent half-life) of 2-PAA determined based on a single dose administration of the pharmaceutical composition of the present disclosure is about 2.5 h or greater, about 2.6 h or greater, about 2.7 h or greater, about 2.8 h or greater, about 2.9 h or greater, about 3.0 h or greater, about 3.1 h or greater, about 3.2 h or greater, about 3.3 h or greater, about 3.4 h or greater, about 3.5 h or greater, about 3.6 h or greater, about 3.7 h or greater, about 3.8 h or greater, about 3.9 h or greater, about 4.0 h or greater, about 4.1 h or greater, about 4.2 h or greater, about 4.3 h or greater, about 4.4 h or greater, or about 4.5 h or greater. In one embodiment, the $t_{1/2}$ of 2-PAA is determined based on a single dose administration of about 1 mg to about 200 mg of betahistine or a pharmaceutically acceptable salt. In one embodiment, the $t_{1/2}$ is of 2-PAA determined based on a single dose administration of about 5 mg, about 10 mg, about 20 mg, about 30 mg, about 40 mg, about 50 mg, about 60 mg, about 70 mg, about 80 mg, about 90 mg, about 100 mg, about 150 mg, or about 200 mg of betahistine or a pharmaceutically acceptable salt.

In one embodiment, the pharmaceutical composition of the present disclosure can be useful in methods for use in treatment or prophylaxis of vestibular disorders. In another embodiment, the pharmaceutical composition of the present disclosure can be useful in methods for use in treatment or prophylaxis of neurotological disorders. In some embodiments, the pharmaceutical composition of the present disclosure can be useful in methods for use in treatment or prophylaxis of otological and/or neurological disorders.

In one embodiment, the pharmaceutical composition of the present disclosure can be useful in methods for use in the treatment or prophylaxis of inner ear dysfunction or inner ear disorder. In one embodiment, inner ear disorders include tinnitus, vestibular vertigo, Meniere's disease, inner ear inflammation or infection, autoimmune ear disorder, or hearing loss. In one embodiment, the pharmaceutical composition of the present disclosure can be useful in methods for use in treatment or prophylaxis of tinnitus, vestibular vertigo, Meniere's disease, and hearing loss. In one embodiment, the pharmaceutical composition of the present disclosure can be useful for treating vestibular vertigo. In another embodiment, the pharmaceutical composition of the present disclosure can be useful for treating Meniere's disease. In one embodiment, vestibular vertigo can include benign paroxysmal positional vertigo, vestibular neuritis and other peripheral vestibular vertigo.

In one embodiment, the pharmaceutical composition of the present disclosure can be useful in methods for use in treatment or prophylaxis or prevention of vertigo, vestibular vertigo, and/or vertigo attacks. In another embodiment, the pharmaceutical composition of the present disclosure can be useful for reducing or reducing the symptoms of vertigo, vestibular vertigo, and/or vertigo attacks.

In one embodiment, the pharmaceutical composition of the present disclosure can be useful in methods for use in the treatment or prophylaxis of Eustachian tube dysfunction.

In one embodiment, the pharmaceutical composition of the present disclosure can be useful for treating or alleviating symptoms of inner ear disorder. In one embodiment, inner ear dysfunction and/or symptoms of inner ear disorder includes hearing loss (including acute hearing loss), tinnitus, nausea and dizziness. In one embodiment, the pharmaceutical composition of the present disclosure can be useful for treating hearing loss. In another embodiment, the pharmaceutical composition of the present disclosure can be useful for treating acute hearing loss.

In one embodiment, the pharmaceutical composition of the present disclosure can be useful as a part of a vestibular therapy. In some embodiments, the vestibular therapy is vestibular rehabilitation.

In one embodiment, the pharmaceutical composition of the present disclosure can be useful for vestibular rehabilitation. In one embodiment, the pharmaceutical composition of the present disclosure can be useful for treating inner ear disorder or symptoms thereof with or in addition to vestibular rehabilitation. In one embodiment, the pharmaceutical composition of the present disclosure can be useful for treating inner ear disorder or symptoms thereof to facilitate vestibular rehabilitation.

Without being bound to any theory, betahistine or a pharmaceutically acceptable salt thereof is believed to act as a partial H1 receptor (H1R) agonist and/or reverse H3 receptor (H3R) antagonist. H1R and H3R together with H2 receptor (H2R) and H4 receptor (H4R) are G-protein-coupled receptor subtypes of histamine receptors, i.e. receptors binding histamine.

Without being bound to any theory, the pharmaceutical composition of the present disclosure can contribute to increase in inner ear blood flow, such as cochlear and vestibular blood flow, and/or cerebral blood flow. In another embodiment, the pharmaceutical composition of the present disclosure can increase histamine turnover and enhance histamine release in the central nervous system (CNS), which may rebalance the neuronal activity of the vestibular nuclei complexes on both sides of the vestibular system. In one embodiment, the pharmaceutical compositions of the present disclosure can inhibit neuronal firing in the vestibular nuclei. In another embodiment, the pharmaceutical composition of the present disclosure can contribute in up-regulation of histamine, which induces general brain arousal favoring sensorimotor activity. In one embodiment, the pharmaceutical compositions of the present disclosure can facilitate vestibular compensation and/or central vestibular compensation.

In one embodiment, the pharmaceutical compositions of the present disclosure can be useful in treating histamine modulated diseases or conditions. In another embodiment, the pharmaceutical composition of the present disclosure can be useful in treating H1R modulated diseases or conditions. In some embodiments, the pharmaceutical compositions of the present disclosure can be useful in treating H3R modulated diseases or conditions.

In one embodiment, the pharmaceutical compositions of the present disclosure can be useful in treating obesity, eating disorders, cognitive disorders, attention deficit disorders, memory processes, dementia and cognition disorders such as Alzheimer's disease and attention-deficit hyperactivity disorder, bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy, vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction, cancer such as cutaneous carcinoma, medullary thyroid carcinoma and melanoma; respiratory disorders such as asthma, gastrointestinal disorders, inflammation, and septic shock, diabetes, type II diabetes, insulin resistance syndrome, metabolic syndrome, polycystic ovary syndrome, Syndrome X, and the like.

In one embodiment, the pharmaceutical compositions of the present disclosure can be useful in treating obesity, attention deficit hyperactivity disorder, cerebrovascular disease, dementia, narcolepsy, sleep disorders, Parkinson, addiction, schizophrenia, Gilles de la Tourette syndrome, and/or Alzheimer's disease.

In one embodiment, the pharmaceutical compositions of the present disclosure can be useful in treating or reducing weight gain. In some embodiments, undesired weight gain may be triggered by administration of certain drugs. For example, antipsychotic drugs acting on histamine receptors, such as olanzapine, can trigger weight gain (Barak et al. *Journal of Psychopharmacology*, 2016, Vol. 30(3) 237-241; which is incorporated by reference herein in its entirety). Accordingly, in one embodiment, the present disclosure provides a method for reducing weight gain induced by antipsychotic drugs acting on histamine receptors, comprising intranasally administering the pharmaceutical composition of the present disclosure.

In one embodiment of the present disclosure, the betahistine or a pharmaceutically acceptable salt thereof can be administered to a subject in need thereof by pathways including nasally (e.g., solution, spray, drops, aerosol, gels), orally (e.g., tablets, capsules, granules, syrups, elixirs, or powders) sublingually, buccally, parenterally (e.g., subcutaneous, intravenous, intramuscular, intrathecal, or intracisternal injection), or infusion techniques (e.g., as sterile injectable aqueous or non-aqueous solutions or suspensions), topically (e.g., drug-releasing skin patch, cream or ointment), intravaginally, by drench, transdermally, intradermally, pulmonary, by intra-uterine, by the use of an aerosol, or rectally (e.g., suppositories, in dosage unit formulations containing nontoxic, pharmaceutically acceptable vehicles or diluents). In one embodiment, the betahistine or a pharmaceutically acceptable salt thereof is administered nasally. In one embodiment, the betahistine or a pharmaceutically acceptable salt thereof is administered by intranasal delivery.

In one embodiment, intranasal delivery of the pharmaceutical composition of the present disclosure is advantageous for allowing non-invasive systemic delivery. In another embodiment, the intranasal delivery of the pharmaceutical composition of the present disclosure avoids or reduces the first pass metabolism of betahistine (compared to oral betahistine). In one embodiment, the intranasal delivery of the pharmaceutical composition of the present disclosure avoids or reduces the gastric side effects (compared to oral betahistine). In another embodiment, the intranasal delivery of the pharmaceutical composition of the present disclosure is advantageous for achieving rapid onset of betahistine's action.

In one embodiment, the pharmaceutical composition of the present disclosure is administered nasally in drops, spray, gel, ointment, cream, powder or suspension. In one embodiment, the pharmaceutical composition of the present disclosure is administered nasally using a dispenser or a device (for example a single-dose ampoule, metered spray, an atomizer, a nebulizer, a pump, a nasal pad, a nasal sponge or a hard gelatin capsule) or any other method of nasal administration which is known in the pharmaceutical literature.

In one embodiment, devices for nasal administration of liquid pharmaceutical compositions of the present disclosure include a pipette (e.g. unit dose pipettes); a dropper including multi-dose droppers; rhinyle catheter; a vapor inhaler; mechanical spray pumps, including squeeze bottles, multi-dose metered-dose spray pumps, single or duo-dose spray pumps, bi-directional multi-dose spray pumps; gas driven spray systems/atomizers and electrically powered nebulizers/atomizers. In one embodiment, devices for nasal administration of powder pharmaceutical compositions of the present disclosure include mechanical powder sprayers, breath actuated inhalers, and insufflators, including breath powered bi-directional delivery devices. These devices are briefly summarized in a review by Djupesland (Drug Deliv. and Transl. Res. (2013) 3:42-62), which is incorporated by reference herein in its entirety.

In one embodiment, the pharmaceutical composition of the present disclosure is administered to the nasal cavity in metered doses. In one embodiment, a metered dose nasal spray can be used to administer the pharmaceutical composition of the present disclosure. In another embodiment, a metered nasal pump spray can be used to administer the pharmaceutical composition of the present disclosure in metered doses. In one embodiment, a metered atomizing spray pump can be used to administer the pharmaceutical composition of the present disclosure in metered doses.

In one embodiment, a nasal pressurized metered-dose inhaler (pMDI) can be used to administer the pharmaceutical composition of the present disclosure in metered doses. In one embodiment, pressurized nasal formulation of the present disclosure can be an aerosol formulation. Such aerosol formulation, in one embodiment, includes betahistine or a pharmaceutically acceptable salt thereof in a pressurized pack with a suitable propellant such as a hydrofluoroalkanes (HFAs), carbon dioxide, or other suitable propellant known in the art. The aerosol can, in one embodiment, also contain a surfactant such as lecithin. The dose of betahistine or a pharmaceutically acceptable salt thereof can be controlled by provision of a metered valve.

In another embodiment, the pharmaceutical composition of the present disclosure is administered to the nasal cavity by conventional means, e.g., with a dropper, pipette or spray.

In one embodiment, a topical pharmaceutical composition of the present disclosure can be provided in the form of a dry powder, for example a powder mix of the compound in a suitable powder base such as lactose, starch, starch derivatives such as hydroxypropylmethyl cellulose and polyvinylpyrrolidone (PVP). In one embodiment, the powder carrier will form a gel in the nasal cavity. The powder composition can be presented in unit dose form for example in capsules or cartridges of, for example, gelatin, or blister packs from which the powder can be administered by means of an inhaler.

In formulations intended for administration to the respiratory tract, including intranasal formulations, particle size of the pharmaceutical composition, when applied, should be less than 100 micron, less than 50 micron, less than 25 micron, less than 20 micron, less than 15 micron, or less than 10 micron. In one embodiment, the particle size of the nasal pharmaceutical composition is less than 10 micron when applied. In one embodiment, $D_{50}$ of the particle size of the nasal pharmaceutical composition is less than 10 micron when applied. In one embodiment, $D_{90}$ of the particle size of the nasal pharmaceutical composition is less than 10 micron when applied.

In one embodiment, the intranasal pharmaceutical compositions of the present disclosure in spray form provide a droplet size distribution Dv(50) of about 150 μm to about 300 μm, including about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm or about 300 μm, inclusive of all ranges between any of these values, when tested at a firing distance of about 20 mm to about 50 mm at firing force of about 5 kg, about 6 kg, or about 7 kg.

In one embodiment, the intranasal pharmaceutical compositions of the present disclosure in spray form provide a droplet size distribution Dv(90) of about 380 μm to about 650 μm, including about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm, about 610 μm, about 620 μm, about 630 μm, about 640 μm, about 650 μm, inclusive of all ranges between any of these values, when tested at a firing distance of about 20 mm to about 50 mm at firing force of about 5 kg, about 6 kg, or about 7 kg.

In one embodiment, the pharmaceutical compositions of the present disclosure are administered 1, 2, 3, 4, 5, 6, 7 8, 9, or 10 times a day. In one embodiment, the pharmaceutical compositions of the present disclosure are administered one or more times a day, where each dose administers a controlled, metered, or set amount of the betahistine or a pharmaceutically acceptable salt thereof.

In one embodiment, the pharmaceutical compositions of the present disclosure are administered to the nasal cavity in a unit dose containing about 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, 31, 32, 33, 34, 35, 36, 37, 38, 39, 40, 41, 42, 43, 44, 45, 46, 47, 48, 49, or 50 mg of betahistine or a pharmaceutically acceptable salt thereof. For example, if a metered nasal spray is used, one spray dose contains about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg of betahistine or a pharmaceutically acceptable salt thereof. In another embodiment, the present disclosure is administered to the nasal cavity in a unit dose containing about 10, 15, 20, 25, 30, 35, 40, 45, or 50 mg of betahistine or a pharmaceutically acceptable salt thereof. In one embodiment, the present disclosure is administered to the nasal cavity in a unit dose containing about 20 mg of betahistine or a pharmaceutically acceptable salt thereof.

In one embodiment, the pharmaceutical compositions of the present disclosure are administered to the nasal cavity in a unit dose containing about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of betahistine or a pharmaceutically acceptable salt thereof.

In one embodiment, the pharmaceutical compositions of the present disclosure are administered to the nasal cavity in a unit dose or a metered dose which provides dose content uniformity with relative standard deviation of less than 5.0%, less than 4.5%, less than 4.0%, less than 3.5%, less than 2.0%, less than 1.5%, less than 1.0%, or less than 0.5%.

In one embodiment, the intranasal pharmaceutical compositions of the present disclosure are administered 1, 2, 3, 4, 5, 6, 7 8, 9, or 10 times a day. In one embodiment, the intranasal pharmaceutical compositions of the present disclosure are administered once a day, twice a day, three times a day, four times a day, five times a day, or six times a day where each dose administers a controlled, metered, or set amount of the betahistine or a pharmaceutically acceptable salt thereof. In some embodiments, the intranasal pharmaceutical composition of the present disclosure is administered three times a day. In some embodiments, the intranasal pharmaceutical compositions of the present disclosure are administered up to six times a day.

In one embodiment, the intranasal pharmaceutical composition of the present disclosure is administered to provide daily dose of betahistine or a pharmaceutically acceptable salt thereof in about 0.01 mg/kg to about 20 mg/kg bodyweight of a human patient, including about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.12 mg/kg, about 0.14 mg/kg, about 0.16 mg/kg, about 0.18 mg/kg, about 0.2 mg/kg, about 0.22 mg/kg, about 0.24 mg/kg, about 0.26 mg/kg, about 0.28 mg/kg, about 0.3 mg/kg, about 0.32 mg/kg, about 0.34 mg/kg, about 0.36 mg/kg, about 0.38 mg/kg, about 0.4 mg/kg, about 0.42 mg/kg, about 0.44 mg/kg, about 0.46 mg/kg, about 0.48 mg/kg, about 0.5 mg/kg, about 0.52 mg/kg, about 0.54 mg/kg, about 0.56 mg/kg, about 0.58 mg/kg, about 0.6 mg/kg, about 0.62 mg/kg, about 0.64 mg/kg, about 0.66 mg/kg, about 0.68 mg/kg, about 0.7 mg/kg, about 0.72 mg/kg, about 0.74 mg/kg, about 0.76 mg/kg, about 0.78 mg/kg, about 0.8 mg/kg, about 0.82 mg/kg, about 0.84 mg/kg, about 0.86 mg/kg, about 0.88 mg/kg, about 0.9 mg/kg, about 0.92 mg/kg, about 0.94 mg/kg, about 0.96 mg/kg, about 0.98 mg/kg, about 1.0 mg/kg, about 1.1 mg/kg, about 1.2 mg/kg, about 1.3 mg/kg, about 1.4, mg/kg about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10 mg/kg, about 11.1 mg/kg, about 11.2 mg/kg, about 11.3 mg/kg, about 11.4, mg/kg about 11.5 mg/kg, about 11.6 mg/kg, about 11.7 mg/kg, about 11.8 mg/kg, about 11.9 mg/kg, about 12 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, about 15.9 mg/kg, about 16 mg/kg, about 16.1 mg/kg, about 16.2 mg/kg, about 16.3 mg/kg, about 16.4 mg/kg, about 16.5 mg/kg, about 16.6 mg/kg, about 16.7 mg/kg, about 16.8 mg/kg, about 16.9 mg/kg, about 17 mg/kg, about 17.1 mg/kg, about 17.2 mg/kg, about 17.3 mg/kg, about 17.4 mg/kg, about 17.5 mg/kg, about 17.6 mg/kg, about 17.7 mg/kg, about 17.8 mg/kg, about 17.9 mg/kg, about 18 mg/kg, about 18.1 mg/kg, about 18.2 mg/kg, about 18.3 mg/kg, about 18.4 mg/kg, about 18.5 mg/kg, about 18.6 mg/kg, about 18.7 mg/kg, about 18.8 mg/kg, about 18.9 mg/kg, about 19 mg/kg, about 19.1 mg/kg, about 19.2 mg/kg, about 19.3 mg/kg, about 19.4 mg/kg, about 19.5 mg/kg, about 19.6 mg/kg, about 19.7 mg/kg, about 19.8 mg/kg, about 19.9 mg/kg, or about 20 mg/kg, inclusive of all ranges between any of these values.

In one embodiment, the intranasal pharmaceutical compositions of the present disclosure are administered to provide a daily dose of betahistine or a pharmaceutically acceptable salt thereof in about 1 mg to about 200 mg per patient. In another embodiment, an intranasal pharmaceutical composition of the present disclosure is administered to provide a daily dose of betahistine or a pharmaceutically acceptable salt thereof in about 5 mg to about 100 mg.

In one embodiment, the intranasal pharmaceutical compositions of the present disclosure comprise betahistine or a pharmaceutically acceptable salt thereof in a concentration of about 1 mg/mL to about 1000 mg/mL. In another embodiment, the intranasal pharmaceutical composition of the present disclosure comprises betahistine or a pharmaceutically acceptable salt thereof in about 10 mg/mL to about 400 mg/mL, including about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, about 280 mg/mL, about 285 mg/mL, about 290 mg/mL, about 295 mg/mL, about 300 mg/mL, about 305 mg/mL, about 310 mg/mL, about 315 mg/mL, about 320 mg/mL, about 325 mg/mL, about 330 mg/mL, about 335 mg/mL, about 340 mg/mL, about 345 mg/mL, about 350 mg/mL, about 355 mg/mL, about 360 mg/mL, about 365 mg/mL, about 370 mg/mL, about 375 mg/mL, about 380 mg/mL, about 385 mg/mL, about 390 mg/mL, about 395 mg/mL, or about 400 mg/mL, including all ranges between any of these values.

In one embodiment, the intranasal pharmaceutical compositions of the present disclosure comprise betahistine or a pharmaceutically acceptable salt thereof in administered in a unit dose or metered dose of about 1 µL to about 1000 µL, including about 1 µL, about 10 µL, about 20 µL, about 30 µL, about 40 µL, about 50 µL, about 60 µL, about 70 µL, about 80 µL, about 90 µL, about 100 µL, about 110 µL, about 120 µL, about 130 µL, about 140 µL, about 150 µL, about 160 µL, about 170 µL, about 180 µL, about 190 µL, about 200 µL, about 210 µL, about 220 µL, about 230 µL, about 240 µL, about 250 µL, about 260 µL, about 270 µL, about 280 µL, about 290 µL, about 300 µL, about 310 µL, about 320 µL, about 330 µL, about 340 µL, about 350 µL, about 360 µL, about 370 µL, about 380 µL, about 390 µL, about 400 µL, about 410 µL, about 420 µL, about 430 µL, about 440 µL, about 450 µL, about 460 µL, about 470 µL, about 480 µL, about 490 µL, about 500 µL, about 510 µL, about 520 µL, about 530 µL, about 545 µL, about 550 µL, about 560 µL, about 570 µL, about 580 µL, about 590 µL, about 600 µL, about 610 µL, about 620 µL, about 630 µL, about 640 µL, about 650 µL, about 660 µL, about 670 µL, about 680 µL, about 690 µL, about 700 µL, about 710 µL, about 720 µL, about 730 µL, about 740 µL, about 750 µL, about 760 µL, about 770 µL, about 780 µL, about 790 µL, about 800 µL, about 810 µL, about 820 µL, about 830 µL, about 840 µL, about 850 µL, about 860 µL, about 870 µL, about 880 µL, about 890 µL, about 900 µL, about 910 µL, about 920 µL, about 930 µL, about 940 µL, about 950 µL, about 960 µL, about 970 µL, about 980 µL, about 990 µL, or about 1000 µL, including all ranges between any of these values. In some embodiments, the intranasal pharmaceutical compositions of the present disclosure comprise betahistine or a pharmaceutically acceptable salt thereof in administered in a unit dose or metered dose of about 10 µL to about 200 µL. In another embodiment, the intranasal pharmaceutical composition of the present disclosure comprises betahistine or a pharmaceutically acceptable salt thereof in administered in a unit dose or metered dose of about 10 µL to about 100 µL.

In one embodiment, a unit dose or a metered dose of an intranasal pharmaceutical composition of the present disclosure comprising betahistine or a pharmaceutically acceptable can be administered in one unit or metered dose at a time, two unit or metered doses at a time, three unit or metered doses at a time, or four unit or metered doses at a time.

In one embodiment, a treatment cycle with the pharmaceutical composition of the present disclosure can be about 1 day to about 7 days, about 1 week to about 5 weeks, or about 1 month to about 12 months. In one embodiment, a treatment cycle with the intranasal pharmaceutical composition can be about 1 day to about 7 days, about 1 week to about 5 weeks, or about 1 month to about 12 months. In one embodiment, a treatment cycle with the intranasal pharmaceutical composition can be about 1 month, about 2 months, about 3 months, about 4 months, about 5 months, about 6 months, about 7 months, about 8 months, about 9 months, about 10 months, about 11 months, or about 12 months. In one embodiment, a treatment cycle with the intranasal pharmaceutical composition can be about 3 month or about 6 months. In one embodiment, a treatment cycle with an intranasal pharmaceutical composition of the present disclosure can be more than one year. In another embodiment, the treatment cycle can be more than one year, more than 1.5 years, more than 2 years, more than 2.5 years, more than 3 years, more than 4 years, or more than 5 years. The appropriate length of a treatment with the pharmaceutical composition of the present disclosure can be determined by a patient's physician and used as directed.

In one embodiment, a pharmaceutical composition of the present disclosure is a solution, suspension, powder, or aerosol. In one embodiment, the pharmaceutical composition of the present disclosure is an aqueous solution.

In one embodiment, the pharmaceutical compositions of the present disclosure can be administered in combination with at least one of enzyme inhibitors or absorption promoters. In one embodiment, at least one enzyme inhibitor is selected from betastatin, amastatin, boroleucin, borvovaline, aprotinin, trypsin inhibitors, fusidic acids, and bile salts. In another embodiment, at least one absorption promoter is selected from β-cyclodextrin, fusidic acid derivatives (sodium taurodihydrofusidate), microspheres, liposomes, bile salts, lauareth-9, saponins, BL-9, glycolate, chitosan, dideanoyl-L-phosphatidylcholine, and lysophosphatidylcholine.

In one embodiment, the pharmaceutical compositions of the present disclosure can further comprise at least one additional pharmaceutically active agent. In some embodiments, at least one additional pharmaceutically active agent is a drug that treats vestibular disorders, neurotological disorders, otological and/or neurological disorders. In some embodiments, at least one additional pharmaceutically active agent is a drug that treats inner ear dysfunctions or inner ear disorders and/or a drug that treats or alleviates symptoms of inner ear disorders and dysfunctions.

In one embodiment, the at least one additional pharmaceutically active agent is selected from a group of glutamate receptor modulators. Non limiting examples of glutamate receptor modulators include glutamate receptor antagonists, AMPA (α-amino-3-hydroxy-5-methyl-4-isoxazolepropionic acid) receptor antagonists, and NMDA (N-methyl-D-aspartate) receptor antagonists. In one embodiment, an AMPA receptor antagonist is selected from 6-cyano-7-nitroquinoxaline-2,3-dione, 2,3-dihydroxy-6-nitro-7-sulfamoyl-benzo[f]quinoxaline-2,3-dione), 6,7-dinitroquinoxaline-2,3-dione, kynurenic acid, 2,3-dihydroxy-6-nitro-7-sulfamoyl-benzo-[f]quinoxaline, or a combination thereof.

In one embodiment, a glutamate receptor antagonist, including NMDA receptor antagonist, is selected from 1-aminoadamantane; dextromethorphan; dextrorphan; ibogaine; ifenprodil; (S)-ketamine; (R)-ketamine; memantine; dizocilpine; gacyclidine; traxoprodil; D-2-amino-5-phosphonopentanoic acid; 3-((±)2-carboxypiperazin-4-yl)-propyl-1-phosphonic acid; conantokin; 7-chlorokynurenate; licostinel; nitrous oxide; phencyclidine; riluzole; tiletamine; aptiganel; remacimide; 5,7-dichlorokynurenic acid; kynurenic acid; 1-aminocyclopropanecarboxylic acid; 2-amino-7-phosphonoheptanoic acid; R-2-amino-5-phosphonopentanoate; 3-[(R)-2-carboxypiperazin-4-yl]-prop-2-enyl-1-phosphonic acid; (+)-(1S,2S)-1-(4-hydroxy-phenyl)-2-(4-hydroxy-4-phenylpiperidino)-1-propanol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*,2R*)-1-(4-hydroxy-3-methylphenyl)-2-(4-(4-fluoro-phenyl)-4-hydroxypiperidin-1-yl)-propan-1-ol-mesylate; or combinations thereof.

EXAMPLES

Example 1: Sample Formulation

Intranasal delivery formulations of the pharmaceutical compositions in accordance with the present disclosure comprising betahistine dihydrochloride were supplied by Otifex Therapeutics and stored in a desiccator at ambient conditions until required.

Formulations with 10, 50 or 200 mg/mL betahistine were prepared as follows:

10 mg/mL Betahistine formulation. 20 mg of benzalkonium chloride (heated to approximately 65° C. to aid transfer) and 20 mg of edetate disodium were added into the same beaker and dissolved in approximately 10 mL of water for injection using a stirrer. 1 g of betahistine dihydrochloride was put into a sterile plastic bottle and 97.5 mg of sodium phosphate dibasic and 552.5 mg of sodium phosphate monobasic were added thereto. Approximately 25 mL of water for injection was added to the bottle and the resulting solution was mixed thoroughly. Then, 100 mg of glycerin, 1.25 g of polyvinyl pyrrolidone, 3.75 g of polyethylene glycol 400 and 2 g of propylene glycol were added (using small amounts of water for transfer). To the resulting mixture, the prepared benzalkonium chloride and edetate disodium solution was added, using approximately 10 mL of water for injection.

The pH of the resulting solution was adjusted to pH 5.0 by adding 3.88 mL of 1M sodium hydroxide. The pH of the solution was checked before quantitatively transferring it into a 100 mL volumetric flank using small amount of water for injection.

Water for injection was added to obtain 100 mL of formulation. The pH was re-checked/adjusted to 5.0 and the formulation was stored at 2-8° C. until required.

The 10 mg/mL betahistine intranasal formulation thus prepared contained the following constituents (all concentrations provided as weight/weight, unless otherwise indicated): 1.0% betahistine dihydrochloride as active substance, 0.1% glycerin, 3.75% polyethylene glycol 400 and 2% propylene glycol as moisturizing agents, 1.25% polyvinyl pyrrolidone for viscosity and to increase nasal ciliary clearance, 0.02% edetate disodium as preservative/stabilizer, 0.02% benzalkonium chloride as preservative, 0.0975% sodium phosphate dibasic and 0.5525% sodium phosphate monobasic as buffer, 1 M sodium hydroxide 3.88 mL for pH adjustment to 5.0, and water for injection q.s. to 100 mL as solvent.

50 and 200 mg/mL Betahistine formulation. The concentration of betahistine dihydrochloride required was 5.0 and 20.0%, respectively, and the amount of 5 M sodium hydroxide 4.38 mL and of 10 M sodium hydroxide 9.3 mL, respectively.

TABLE 2

Sample Formulation Prepared by Example 1

| Constituent | Amount | Concentration (mg/mL) | Function |
|---|---|---|---|
| Betahistine Dihydrochloride | 1 g<br>5 g<br>20 g | 10.0<br>50.0<br>200.0 | Active Substance |
| Benzalkonium Chloride | 20 mg | 0.2 | Preservative |
| Glycerin | 100 mg | 1.0 | Moisturizing Agent |
| Edetate Disodium | 20 mg | 0.2 | Preservative/Stabilizer |
| Polyvinyl Pyrrolidone | 1.25 g | 12.5 | Viscosity/Nasal Ciliary Clearance |
| Polyethylene Glycol 400 | 3.75 g | 37.5 | Moisturizing Agent |
| Propylene Glycol | 2 g | 20 | Moisturizing Agent |
| Sodium Phosphate Dibasic | 97.5 mg | 0.975 | Buffer |
| Sodium Phosphate Monobasic | 552.5 mg | 5.525 | Buffer |
| 1M Sodium Hydroxide | 3.88 mL<br>4.38 mL<br>9.3 mL | | pH adjustment to 5.0 |
| Water | to 100 mL | | Solvent |

Example 2: Safety and Pharmacokinetic Profile Evaluation in Dogs

The safety and pharmacokinetic profile of intranasal betahistine was first evaluated in a single dose toxicology study in male and female beagle dogs (14-21 months of age, weight 8.2-11.8 kg). Both the vehicle and test article were delivered in a single dose via a nasal spray pump (Aptar Classic Line) with a delivery volume of 100 μL into both nostrils at total dose levels of 0 (vehicle), 4, 20 or 80 mg of betahistine dihydrochloride. Each treatment group was made up of 1 dog/sex. Animals were observed for 7 days, then allowed a 3-day washout period prior to being used for a repeat-dose study, where they received for 14 consecutive days daily in three doses separated by approximately 4 hours 0 (vehicle), 12, 60 or 240 mg of betahistine dihydrochloride.

For toxicokinetic assessments blood samples were collected as follows: prior to dosing and approximately 5, 15 and 30 minutes, 1, 2, 6, 24 and 168 hours following dosing in the single-dose phase and prior to the first dose on study days 1, 8 and 14 as well as 2 hours following the third dose of the day on study days 1 and 14 as well as on study day 15, prior to necropsy. Plasma concentrations were measured with liquid chromatographic tandem mass spectrometry (LC-MS/MS; SCIEX API 5000 for betahistine and SCIEX API 4000 for 2-pyridylacetic acid (2-PAA)) with a validated method. Betahistine-$^{13}$CD$_3$ dihydrochloride and 2-PAA-D$_4$ hydrochloride served as internal standards. The standard calibration range—using a plasma sample volume of 0.05 mL—for betahistine was 0.05 to 50 ng/mL and for 2-PAA it was 1 to 1000 ng/mL. The limit of quantitation was 0.05 ng/mL for betahistine and 1.0 ng/mL for 2-PAA.

In case of betahistine, the method involved a liquid-liquid extraction; in case of 2-PAA it involved protein precipitation. For betahistine, plasma samples were extracted under basic conditions with an organic solvent; the organic phase was dried and reconstituted in reconstitution solvent. Approximately 0.1 mL of the aqueous layer was transferred into polypropylene vials for LC-MS/MS analysis. For 2-PAA, plasma samples were precipitated with a mixture of organic solvents, supernatant was diluted and 0.12 mL was transferred into polypropylene vials for LC-MS/MS analysis. Sample analysis was conducted using reversed phase chromatography.

Intranasal betahistine was well tolerated. Test article-related clinical signs consisting of mild to moderate salivation were noted following intranasal delivery of 80 mg of the test article in both the single dose and the repeated-dose (240 mg/day) phase of the study. Salivation after betahistine treatment was previously reported to occur in dogs, it was transient in nature in the present study and resolved quickly. Body weights, clinical pathology and gross necropsy findings were unremarkable. No adverse treatment-related microscopic findings were noted in the study.

Figure 2:
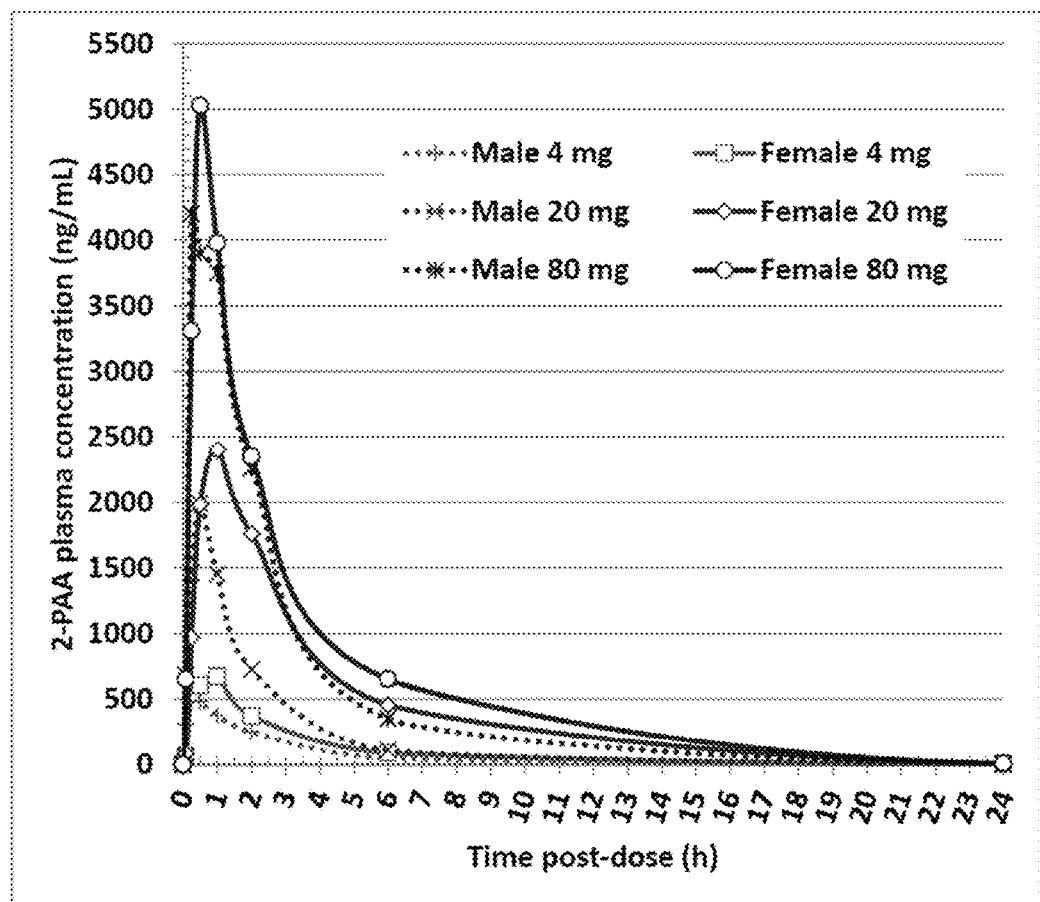
FIG. 2 shows the concentration of 2-pyridylacetic acid (2-PAA) in plasma from 6 beagle dogs following intranasal administration of a single dose of betahistine dihydrochloride 4, 20 or 80 mg over time.

Betahistine was rapidly absorbed following single dose intranasal administration, with the peak concentration observed at the 5-minute time point ($T_{max}$) (FIG. 1). Without being bound to any theory, the $T_{max}$ of 5 minutes post-dose suggests rapid onset of betahistine's pharmacological activity. The increase in $C_{max}$ was linear to the dose administered, but not proportional—$C_{max}$ amounted to 26, 81 and 248 ng/mL for the 4, 20 and 80 mg groups (average for male and female animals). Concentrations declined rapidly by more than 90% at the 1-hour time-point. Quantifiable plasma concentrations were no longer observable after the 2- or 6-hour time-points in the 4 and 20 mg dose groups, but were observed out to the 24-hour time-point in the 80 mg dose group. The 2-PAA metabolite, like its parent, appeared rapidly by the 5-minute time-point, indicating rapid formation at similar rates across the dose levels evaluated (FIG. 2). 2-PAA reached peak concentrations of 606, 2195 and 4615 ng/mL for the 4, 20 and 80 mg groups (average for male and female animals) at times ranging between 15 minutes and 1 hour. The increases in $C_{max}$ were roughly dose-proportional between 4 and 20 mg dose groups and less than proportional between the 20 and 80 mg dose groups, indicating a saturation of the elimination process above the 20 mg dose level. Following the peak levels, 2-PAA declined rapidly and approximately linearly, in general with the last measurable values at 24 hours post-dose.

In the repeated-dose evaluation, there were measurable levels of betahistine and 2-PAA in all collected samples in the 20 and 80 mg dose groups, and in most samples of the 4 mg dose group. The increases in betahistine concentration across dose levels were less than proportional at comparable plasma sampling times. Although overall betahistine was rapidly eliminated, small plasma concentration levels could still be observed in trough samples from study days 8 and 14, suggesting maintenance of some, albeit low basal level.

The results from the single-dose and repeated-dose toxicology study show that intranasal betahistine is feasible and results in rapid and meaningful systemic exposure. The treatment was well tolerated in dogs.

Example 3: Safety and Pharmacokinetic Profile Evaluation in Humans

The safety and pharmacokinetic profile of intranasal betahistine was further evaluated in a double-blind, randomized, placebo-controlled, single ascending-dose clinical trial involving a total of 32 healthy male and female volunteers. The main inclusion criteria were that subjects had to be aged 18-45 years and show a body mass index within the range of 18-30 kg/m². Subjects were required to fast for 8 hours prior to study drug administration and for 2 hours post-dose. Water was withheld from 1 hour prior to study drug administration and for 1 hour post-dose.

Betahistine dihydrochloride was tested in four dose cohorts at 5, 10, 20 and 40 mg; in each cohort 6 subjects received the active drug and 2 subjects received matching placebo. The betahistine was supplied as a 50 and 200 mg/mL solution in a HDPE bottle and spray pump pack (Aptar Classic Line) that delivers an accurate 100 μL per actuation. The study drug was delivered into the right nostril of subjects while they were in a supine position. For the 5 and 20 mg doses, one application of 50 and 200 mg/mL, respectively, was needed, whereas for the 10 and 40 mg doses, two applications of 50 and 200 mg/mL were required.

Serial blood samples were collected through 24 hours, following dosing on Day 1, at Day 4 and Day 7 to determine concentrations of betahistine and its main metabolite, 2-PAA in plasma. Plasma samples were assayed for BH content using validated procedures and methods. Blood samples (6 mL) were collected into tubes containing $K_2$EDTA and were centrifuged at approximately 2000 g for 10 minutes at +4° C. and the resultant plasma transferred into 2 clean, labelled 2 mL cryovials. All plasma samples were stored at −70° C. or below until all samples had been collected and sent as a single batch for analysis. Aliquot 1 and 2 were sent as separate shipments. Concentrations were determined using liquid chromatographic tandem mass spectrometry (LC-MS/MS; SCIEX API 5000 for betahistine and SCIEX API 4000 for 2-PAA) with a validated method. Betahistine-$^{13}CD_3$ dihydrochloride and 2-PAA-$D_4$ hydrochloride served as internal standards. The standard calibration range—using a plasma sample volume of 0.2 and 0.1 mL, respectively—for betahistine was 10 to 800 pg/mL and for 2-PAA it was 2 to 2000 ng/mL. The limit of quantitation was 10 pg/mL for betahistine and 2.0 ng/mL for 2-PAA.

In case of betahistine, the method involved a liquid-liquid extraction; in case of 2-PAA it involved protein precipitation. For betahistine, plasma samples were extracted under basic conditions with an organic solvent; the organic phase was dried and reconstituted in reconstitution solvent. Approximately 0.120 mL of the aqueous layer was transferred into polypropylene vials for LC-MS/MS analysis. For 2-PAA plasma samples were precipitated with a mixture of organic solvents, supernatant was diluted and 0.120 mL was transferred into polypropylene vials for LC-MS/MS analysis. Sample analysis was conducted using reversed phase chromatography.

Figure 3:
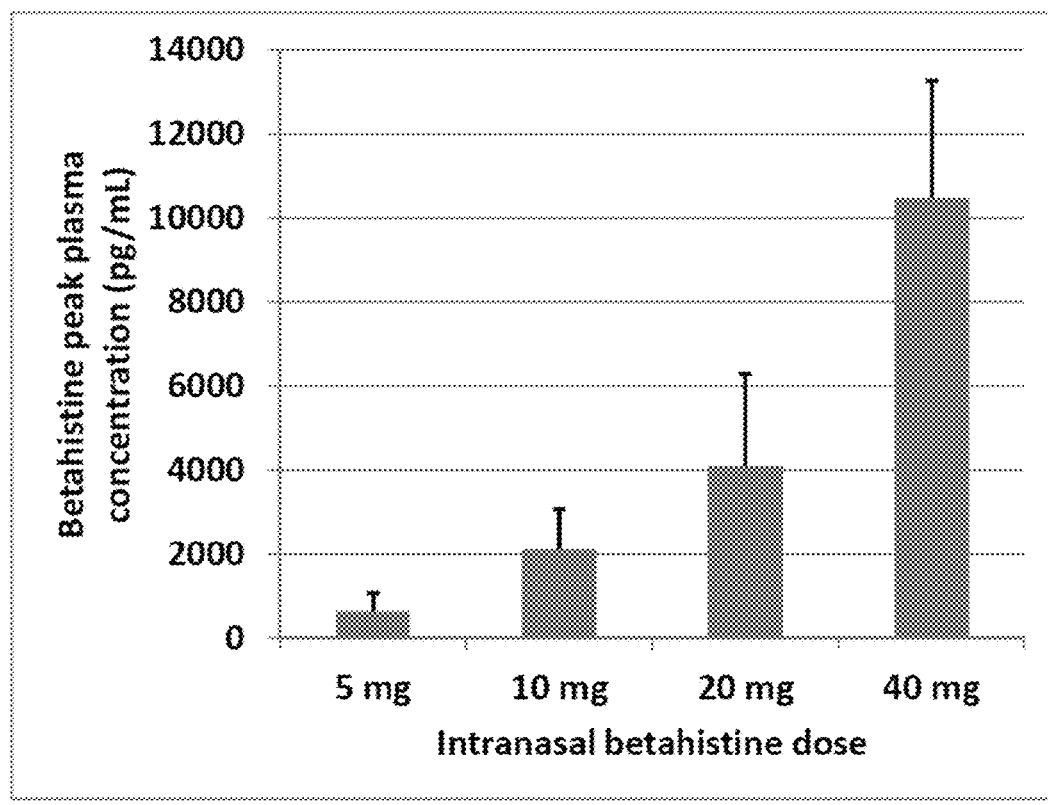
FIG. 3 shows the peak concentration $C_{max}$ of betahistine in plasma from 24 healthy volunteers following intranasal administration of a single dose of betahistine dihydrochloride 5, 10, 20 or 40 mg (whiskers=standard deviation).
Figure 4:
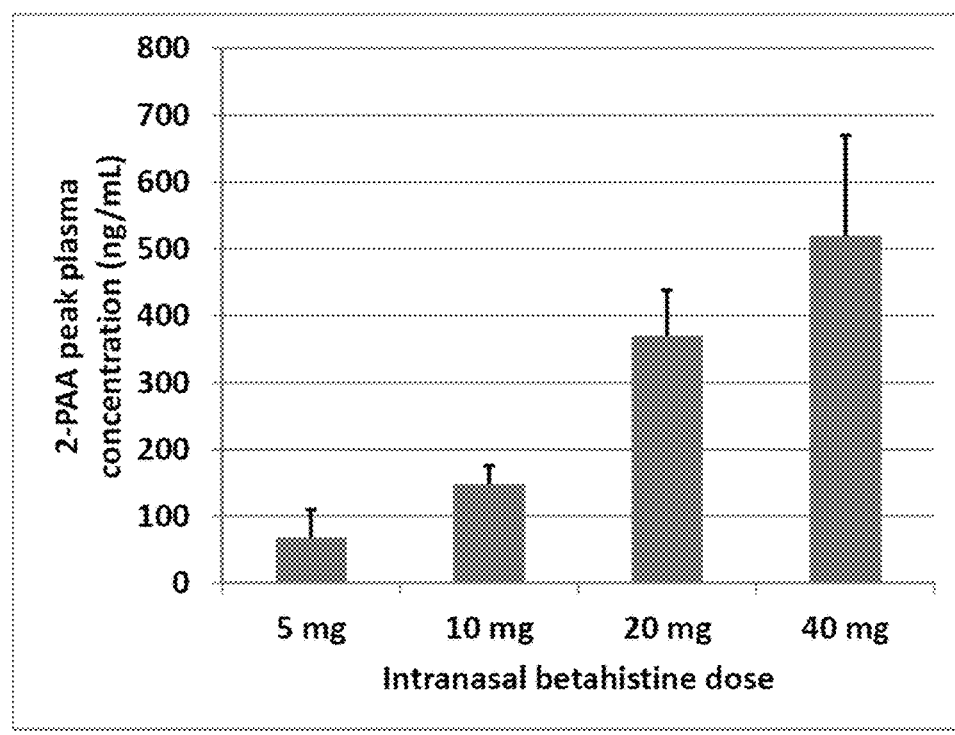
FIG. 4 shows the peak concentration $C_{max}$ of 2-pyridylacetic acid (2-PAA) in plasma 24 from healthy volunteers following intranasal administration of a single dose of betahistine dihydrochloride 5, 10, 20 or 40 mg (whiskers=standard deviation).

The treatment with betahistine at the tested doses of 5, 10, 20 and 40 mg was well tolerated. There were no differences in hematology, biochemistry, urinalysis, vital signs and electrocardiogram assessments between active- and placebo-treated subjects. The incidence of treatment-emergent adverse events was also similar for both groups of subjects, and there was no apparent dose-related trend in the incidence of adverse events for active-treated subjects. Pharmacokinetic parameters of systemic exposure of betahistine and 2-PAA increased with dose level. For betahistine, peak concentrations in plasma were 4.1 and 10.5 ng/mL for the two highest doses (FIG. 3), which is markedly higher than the $C_{max}$ of <0.5 ng/mL reported by Chen et al. (Xenobiotica, 2003, 3(12)3, 1261) following oral administration of betahistine 24 mg. The peak was achieved at approximately 10 minutes post-dose. For the metabolite 2-PAA peak concentrations were 370 and 519 ng/mL for the two highest doses (FIG. 4), which is similar to the level re-ported by Val et al. (*Arzneimittelforschung*, 2010, 60(7), 440) following oral administration of betahistine 16 mg (522 ng/mL). $T_{max}$ was reached after 1.2 hours, which is also similar to results from studies with oral administration of betahistine 16 or 50 mg, reported by Chen et al. (2003) at 1 hour and Moorthy et al. (*Biopharm. Drug Dispos.*, 2015, 36(12), 429) at 1.5 hours.

For each subject who completed the study, plasma concentration-time data of betahistine and 2-PAA were used for the calculation of the following pharmacokinetic parameters:

$C_{max}$ Maximum observed plasma concentration obtained directly from the data.

$t_{max}$ Time to maximum observed concentration, taken directly from the data. If the maximum plasma concentration occurred at more than one time point, the first was chosen.

$AUC_{0-last}$ Area under the plasma concentration versus time curve, calculated using the linear trapezoidal rule from time 0 to time t, where t is the time of last quantifiable concentration.

$\lambda_z$ Terminal elimination rate constant obtained from the slope of the line, fitted by linear least squares regression through the terminal points of the logarithmic concentration-time profiles (sometimes also referred to as $k_{el}$).

$AUC_{0-inf}$ Area under the plasma concentration versus time curve from zero to infinity, calculated as $(AUC_{0-t}+C_t/\lambda_z)$, where $C_t$ is the last quantifiable concentration.

t½ Apparent terminal half-life, calculated as $t\frac{1}{2}=\ln(2)/\lambda_z$.

Dose normalized parameters $C_{max}$/Dose and AUC/Dose were also calculated.

A summary of the determined pharmacokinetic parameters of betahistine by treatment is given in Tables 3-4.

TABLE 3

Summary of Pharmacokinetic Parameters of Betahistine

| Cohort* | Dose (mg) | N | Mean (CV %) | | | | |
|---|---|---|---|---|---|---|---|
| | | | $C_{max}$ (pg/mL) | $AUC_{0\text{-}last}$ (hr*pg/mL) | $AUC_{0\text{-}inf}$ (hr*pg/mL) | $t_{1/2}$ (hr) | Median (range) $t_{max}$ (hr) |
| Cohort 1 Linear | 5 mg | 6 | 638 (67%) | 209 (75%) | 277[a] (60%) | 0.208[a] (83%) | 0.208 (0.08-0.33) |
| Cohort 2 Linear | 10 mg | 6 | 2112 (46%) | 533 (45%) | 697[a] (39%) | 0.883[a] (140%) | 0.167 (0.08-0.17) |
| Cohort 3 Linear | 20 mg | 6 | 4105 (53%) | 1608 (65%) | 1626 (65%) | 0.519 (116%) | 0.167 (0.08-0.33) |
| Cohort 4 Linear | 40 mg | 6 | 10490 (26%) | 3531 (31%) | 2941[b] (2.3%) | 0.926[b] (108%) | 0.125 (0.08-0.27) |

Key:
[a] n = 3;
[b] n = 2;
NA = Not applicable (n = 0)
*Linear—conducted at Linear Clinical Research.

TABLE 4

Additional Pharmacokinetic Parameters of Betahistine

| Pharmacokinetic Parameter | Cohort | Dose (mg) | N | Mean | CV (%) |
|---|---|---|---|---|---|
| Kel (1/hr) | 1 L | 5 | 3 | 5.09 | 68% |
| Kel (1/hr) | 2 L | 10 | 3 | 2.83 | 78% |
| Kel (1/hr) | 3 L | 20 | 6 | 2.27 | 48% |
| Kel (1/hr) | 4 L | 40 | 2 | 1.79 | 108% |

A summary of the determined pharmacokinetic parameters of 2-PAA is given in Tables 5-6.

TABLE 5

Summary of Pharmacokinetic Parameters of 2-PAA

| Cohort* | Dose (mg) | N | Mean (CV %) | | | | |
|---|---|---|---|---|---|---|---|
| | | | $C_{max}$ (pg/mL) | $AUC_{0\text{-}last}$ (hr*pg/mL) | $AUC_{0\text{-}inf}$ (hr*pg/mL) | $t_{1/2}$ (hr) | Median (range) $t_{max}$ (hr) |
| Cohort 1 Linear | 5 mg | 6 | 67.8 (61%) | 387 (57%) | 427 (54%) | 4.36 (41%) | 1.008 (1.00-1.50) |
| Cohort 2 Linear | 10 mg | 6 | 148 (19%) | 736 (13%) | 768 (13%) | 3.76 (29%) | 1.250 (0.55-2.00) |
| Cohort 3 Linear | 20 mg | 6 | 370 (18%) | 2000 (20%) | 2029 (19%) | 3.49 (15%) | 1.250 (0.50-1.50) |
| Cohort 4 Linear | 40 mg | 6 | 519 (29%) | 2828 (24%) | 2901 (24%) | 3.93 (23%) | 1.000 (1.00-1.50) |

Key:
[a] n = 3;
[b] n = 2;
NA = Not applicable (n = 0)
*Linear—conducted at Linear Clinical Research.

TABLE 6

Additional Pharmacokinetics parameters of 2-PAA

| Pharmacokinetic Parameter | Cohort | Dose (mg) | N | Mean | CV(%) |
|---|---|---|---|---|---|
| Kel (1/hr) | 1 L | 5 | 6 | 0.180 | 36% |
| Kel (1/hr) | 2 L | 10 | 6 | 0.199 | 30% |
| Kel (1/hr) | 3 L | 20 | 6 | 0.203 | 18% |
| Kel (1/hr) | 4 L | 40 | 6 | 0.187 | 32% |

The above data in Tables 3-6 indicate that pharmacokinetic parameters of systemic exposure of betahistine and 2-PAA increased with dose level. Graphical presentation of the dose response suggests that the exposure of betahistine is dose proportional across the betahistine dose range in this study of 5 to 40 mg. For betahistine, peak concentrations are achieved at 5 to 20 minutes, and the apparent half-life is less than 1 hour. For the metabolite 2-PAA, peak concentrations are achieved at approximately 1-1.25 hours post-dose (range 20 minutes to 2 hours), and the apparent half-life is approximately 4 hours.

In summary, the results from this study show that intranasal betahistine is well tolerated and—unlike oral administration—provides for quantifiable and meaningful plasma concentrations of the active parent compound. The peak concentration is reached about 10 minutes post-dose and without being bound to any theory, suggests a rapid onset of action, which can be of particular therapeutic utility e.g. in case of acute medical need. The experiment shows for the first time that betahistine can be effectively and safely administered systemically in a non-invasive way by the intranasal route.

Example 4: Dose Content Uniformity

Formulations with 10 and 200 mg/mL betahistine were prepared according to Example 1 and Table 2 with the exception of adjustment of pH value to 5.5.

Formulations were filled into 100 µL Aptar Classic Line pump sprays and then fired into an appropriate volumetric flask, made to volume with diluent. Tables 7-8 show dose content uniformity.

TABLE 7

Dose Content Uniformity of 10 mg/mL Formulation

| Prep | Assay µg | % Mean |
|---|---|---|
| 1 | 1.02443 | 103.2 |
| 2 | 1.00160 | 100.9 |
| 3 | 0.97018 | 97.8 |
| 4 | 0.99444 | 100.2 |
| 5 | 0.96749 | 97.5 |
| 6 | 1.02161 | 102.9 |
| 7 | 0.99941 | 100.7 |
| 8 | 0.94260 | 95.0 |
| 9 | 1.01197 | 102.0 |
| 10 | 0.99125 | 99.9 |
| Average | 0.99 | |
| % RSD | 2.60 | |

TABLE 8

Dose Content Uniformity of 200 mg/mL Formulation

| Prep | Assay µg | % Mean |
|---|---|---|
| 1 | 20.51925 | 99.3 |
| 2 | 20.45679 | 99.0 |

TABLE 8-continued

Dose Content Uniformity of 200 mg/mL Formulation

| Prep | Assay μg | % Mean |
|---|---|---|
| 3 | 20.66933 | 100.0 |
| 4 | 20.87421 | 101.0 |
| 5 | 20.83816 | 100.8 |
| 6 | 20.32822 | 98.4 |
| 7 | 20.54321 | 99.4 |
| 8 | 20.43937 | 98.9 |
| 9 | 20.91649 | 101.2 |
| 10 | 21.05841 | 101.9 |
| Average | 20.66 | |
| % RSD | 1.18 | |

Example 5: Pharmacokinetic Profile Evaluation in Dogs

In this study, the pharmacokinetic profile of betahistine was evaluated after a single dose administration of betahistine in male and female beagle dogs (age 5-7 months; weight of 5-11 kg, within a range of 3 kg for each sex) for three routes of administration: oral, intranasal, and intravenous.

On Day 1 of the study, betahistine (BH) was delivered orally at a dose of 12 mg/kg, 24 mg/kg, or 48 mg/kg. Each treatment group comprised 8 animals (4 males and 4 females). For pharmacokinetic assessment, plasma samples were collected prior to dosing, and then at 5, 10, 20 and 30 min, 1, 2, 3, 6, 24 hours after dosing.

On Day 8 of the study, the animals that received oral BH at a dose of 12 mg/kg were administered the test betahistine composition intranasally at a dose of 40 mg betahistine dihydrochloride; the animals that received oral BH at a dose of 24 mg/kg were administered the test betahistine composition intranasally at a dose of 80 mg betahistine dihydrochloride; and the animals that received oral BH at a dose of 48 mg/kg were administered the test betahistine composition intranasally at a dose of 120 mg betahistine dihydrochloride. The test betahistine composition was delivered intranasally in a single dose via an Aptar nasal spray pump device at a total dose level of 40, 80 and 120 mg of betahistine dihydrochloride. Plasma samples were collected prior to dosing, and then at 5, 10, 20 and 30 min, 1, 2, 3, 6, 24 hours after dosing.

On Day 15 of the study, the animals that received oral BH at a dose of 12 mg/kg and the test betahistine composition intranasally at a dose of 40 mg betahistine dihydrochloride were administered a bolus intravenous injection of betahistine at a dose of 0.44 mg/kg. Plasma samples were collected prior to dosing, and then at 5, 10, 20 and 30 min, 1, 2, 3, 6, 24 hours after dosing.

Plasma concentrations were measured with liquid chromatographic tandem mass spectrometric method (LC-MS/MS; SCIEX API 5000 for betahistine, SCIEX API 4000 for 2-Pyridylacetic Acid (2-PAA)) with validated methods. Betahistine 13CD3 dihydrochloride and 2-pyridylacetic acid-D4 hydrochloride were used as respective internal standards. The calibration range for betahistine was 0.05-250 ng/mL and for 2-PAA 2.00-3000 ng/mL using a plasma sample volume of 0.50 mL.

For determination of betahistine, the method involved liquid-liquid extraction, for 2-PAA, the method involved protein precipitation. Plasma samples were prepared for betahistine by extraction under basic conditions with an organic solvent, then the organic phase was dried, reconstituted and transferred for LC/MS-MS analysis. For 2-PAA, plasma samples were precipitated with a mixture of organic solvents, the supernatant dried, reconstituted and transferred for LC/MS-MS analysis. Sample analysis was performed using reversed phase chromatography.

Intranasal administration of betahistine was well tolerated in the dogs. In the highest concentration betahistine group salivation was noted in most animals and sneezing occurred in 2/8 animals at that dose level.

Plasma levels of betahistine and 2-PAA in the study animals were as shown in the Tables 9-17.

TABLE 9

Plasma levels of betahistine following intranasal administration of test betahistine composition at a total dose of 40, 80, and 120 mg of betahistine dihydrochloride (values for male and female animals shown separately)

| | Betahistine Plasma Concentration (pg/mL) | | | | | |
|---|---|---|---|---|---|---|
| Time (h) | Male 40 mg | Female 40 mg | Male 80 mg | Female 80 mg | Male 120 mg | Female 120 mg |
| 0 | 0 | 54.25 | 29.25 | 0 | 90 | 25.5 |
| 0.08333333 | 469250 | 733750 | 606500 | 1639750 | 661750 | 1144000 |
| 0.167 | 440300 | 457750 | 619750 | 1178000 | 515250 | 825250 |
| 0.333 | 333883 | 295950 | 179300 | 605000 | 295000 | 244750 |
| 0.5 | 52123 | 15475 | 14540 | 50450 | 27175 | 31200 |
| 1 | 9045 | 5088 | 12143 | 20975 | 13060 | 16510 |
| 2 | 2319 | 879 | 546 | 8680 | 3718 | 5010 |
| 3 | 453 | 850 | 252 | 2078 | 945 | 1894 |
| 6 | 244 | 361 | 340 | 712 | 266 | 1118 |
| 24 | 221 | 96 | 67 | 189 | 288 | 314 |

TABLE 10

Plasma levels of betahistine following intranasal administration of test betahistine composition at a total dose of 40, 80, and 120 mg of betahistine dihydrochloride (values for male and female animals pooled)

| | Betahistine Plasma Concentration (pg/mL) | | |
|---|---|---|---|
| Time (h) | 40 mg | 80 mg | 120 mg |
| 0 | 27 | 15 | 58 |
| 0.08333333 | 601500 | 1123125 | 902875 |
| 0.167 | 449025 | 898875 | 670250 |
| 0.333 | 314916 | 392150 | 269875 |
| 0.5 | 33799 | 32495 | 29188 |
| 1 | 7066 | 16559 | 14785 |
| 2 | 1599 | 4613 | 4364 |
| 3 | 652 | 1165 | 1419 |

TABLE 10-continued

Plasma levels of betahistine following intranasal administration of test betahistine composition at a total dose of 40, 80, and 120 mg of betahistine dihydrochloride (values for male and female animals pooled)

| | Betahistine Plasma Concentration (pg/mL) | | |
|---|---|---|---|
| Time (h) | 40 mg | 80 mg | 120 mg |
| 6 | 303 | 526 | 692 |
| 24 | 158 | 128 | 301 |

TABLE 11

Plasma levels of betahistine following oral administration of betahistine at a dose of 12 mg/kg, 24 mg/kg, and 48 mg/kg (values for male and female animals shown separately)

| | Betahistine Plasma Concentration (pg/mL) | | | | | |
|---|---|---|---|---|---|---|
| Time (h) | Male 12 mg/kg | Female 12 mg/kg | Male 24 mg/kg | Female 24 mg/kg | Male 48 mg/kg | Female 48 mg/kg |
| 0 | 0 | 0 | 0 | 0 | 0 | 0 |
| 0.08333333 | 1.35 | 2588 | 4690 | 5316 | 14328 | 9873 |
| 0.167 | 2728 | 6465 | 5055 | 5238 | 35703 | 9243 |
| 0.333 | 5800 | 10113 | 23903 | 7133 | 14330 | 11483 |
| 0.5 | 18915 | 7798 | 17840 | 11983 | 33700 | 19350 |
| 1 | 5653 | 14058 | 26880 | 36825 | 80150 | 32825 |
| 2 | 457 | 263 | 2079 | 3578 | 21680 | 21325 |
| 3 | 36 | 0 | 611 | 1710 | 2997 | 10138 |
| 6 | 16 | 0 | 78 | 342 | 238 | 640 |
| 24 | 21 | 0 | 0 | 0 | 0 | 0 |

TABLE 12

Plasma levels of betahistine following oral administration of betahistine at a dose of 12 mg/kg, 24 mg/kg, and 48 mg/kg (values for male and female animals pooled)

| | Betahistine Plasma Concentration (pg/mL) | | |
|---|---|---|---|
| Time (h) | 12 mg/kg | 24 mg/kg | 48 mg/kg |
| 0 | 0 | 0 | 0 |
| 0.08333333 | 1969 | 5002.875 | 12100 |
| 0.167 | 4596.25 | 5146.25 | 22472.5 |
| 0.333 | 7956.25 | 15517.5 | 12906.25 |
| 0.5 | 13356.25 | 14911.25 | 26525 |
| 1 | 9855 | 31852.5 | 56487.5 |
| 2 | 359.88 | 2828 | 21503 |
| 3 | 18.1 | 1160.6 | 6567.1 |
| 6 | 7.975 | 210.1 | 438.99 |
| 24 | 10.4625 | 0 | 0 |

TABLE 13

Plasma levels of betahistine following intravenous administration of betahistine at a dose of 0.44 mg/kg (values for male and female animals shown separately)

| | Betahistine Plasma Concentration (pg/mL) | |
|---|---|---|
| Time (h) | Male 0.44 mg/kg | Female 0.44 mg/kg |
| 0 | 110 | 55.05 |
| 0.08333333 | 58175 | 43700 |
| 0.167 | 29100 | 14825 |
| 0.333 | 8063 | 5995 |
| 0.5 | 5568 | 4063 |
| 1 | 349 | 268 |

TABLE 13-continued

Plasma levels of betahistine following intravenous administration of betahistine at a dose of 0.44 mg/kg (values for male and female animals shown separately)

| | Betahistine Plasma Concentration (pg/mL) | |
|---|---|---|
| Time (h) | Male 0.44 mg/kg | Female 0.44 mg/kg |
| 2 | 993 | 274 |
| 3 | 81 | 95 |

TABLE 13-continued

Plasma levels of betahistine following intravenous administration of betahistine at a dose of 0.44 mg/kg (values for male and female animals shown separately)

| | Betahistine Plasma Concentration (pg/mL) | |
|---|---|---|
| Time (h) | Male 0.44 mg/kg | Female 0.44 mg/kg |
| 6 | 1051 | 648 |
| 24 | 0 | 405 |

TABLE 14

Plasma levels of betahistine following intravenous administration of betahistine at a dose of 0.44 mg/kg (values for male and female animals pooled)

| Time (h) | Betahistine Plasma Concentration (pg/mL) 0.44 mg/kg |
|---|---|
| 0 | 82.525 |
| 0.08333333 | 50937.5 |
| 0.167 | 21962.5 |
| 0.333 | 7028.75 |
| 0.5 | 4815 |
| 1 | 308.375 |
| 2 | 633.34 |
| 3 | 87.75 |
| 6 | 849.25 |
| 24 | 202.25 |

TABLE 15

Plasma levels of 2-PAA following intranasal administration of test betahistine composition at a total dose of 40, 80, and 120 mg of betahistine dihydrochloride (values for male and female animals pooled)

| | 2-PAA Plasma Concentration (ng/mL) | | |
|---|---|---|---|
| Time (h) | 40 mg | 80 mg | 120 mg |
| 0 | 1 | 3 | 3 |
| 0.08333333 | 350 | 422 | 482 |
| 0.167 | 1436 | 1414 | 1356 |
| 0.333 | 3242 | 2996 | 2424 |
| 0.5 | 4231 | 3531 | 2715 |
| 1 | 4101 | 5163 | 3835 |
| 2 | 2937 | 3345 | 2494 |
| 3 | 1676 | 2073 | 1499 |
| 6 | 382 | 424 | 318 |
| 24 | 8 | 13 | 15 |

TABLE 16

Plasma levels of 2-PAA following oral administration of betahistine at a dose of 12 mg/kg, 24 mg/kg, and 48 mg/kg (values for male and female animals pooled)

| | 2-PAA Plasma Concentration (ng/mL) | | |
|---|---|---|---|
| Time (h) | 12 mg/kg | 24 mg/kg | 48 mg/kg |
| 0 | 0 | 0 | 0 |
| 0.08333333 | 186.31625 | 266.46 | 233.64875 |
| 0.167 | 720.45 | 528.7875 | 694.2125 |
| 0.333 | 2492.75 | 2619.25 | 2298.75 |
| 0.5 | 5722.5 | 5121.25 | 5175 |
| 1 | 13236.3 | 17751.3 | 25963.8 |
| 2 | 11664 | 21963 | 39113 |
| 3 | 6443.8 | 14701 | 33845 |
| 6 | 1611.5 | 3966.3 | 10266 |
| 24 | 7.73125 | 13.7863 | 35.675 |

TABLE 17

Plasma levels of 2-PAA following intravenous administration at a dose of 0.44 mg/kg (values for male and female animals pooled)

| | 2-PAA Plasma Concentration (ng/mL) |
|---|---|
| Time (h) | 0.44 mg/kg |
| 0 | 0.6088 |
| 0.08333333 | 652.875 |
| 0.167 | 709.875 |
| 0.333 | 633.375 |
| 0.5 | 583.75 |
| 1 | 513 |
| 2 | 286.13 |
| 3 | 164.75 |
| 6 | 36.475 |
| 24 | 2.1475 |

Figure 5:
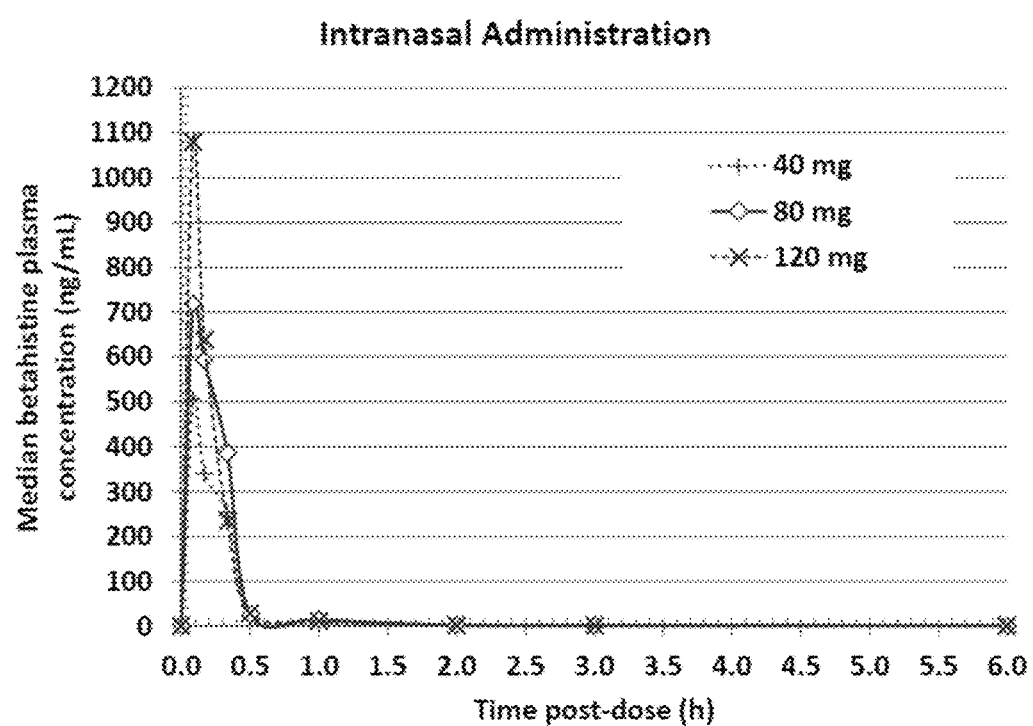
FIG. 5 shows the median betahistine concentration in plasma over time from 8 beagle dogs following intranasal administration of a single dose of betahistine dihydrochloride at a dose of 40, 80, or 120 mg.
Figure 6:
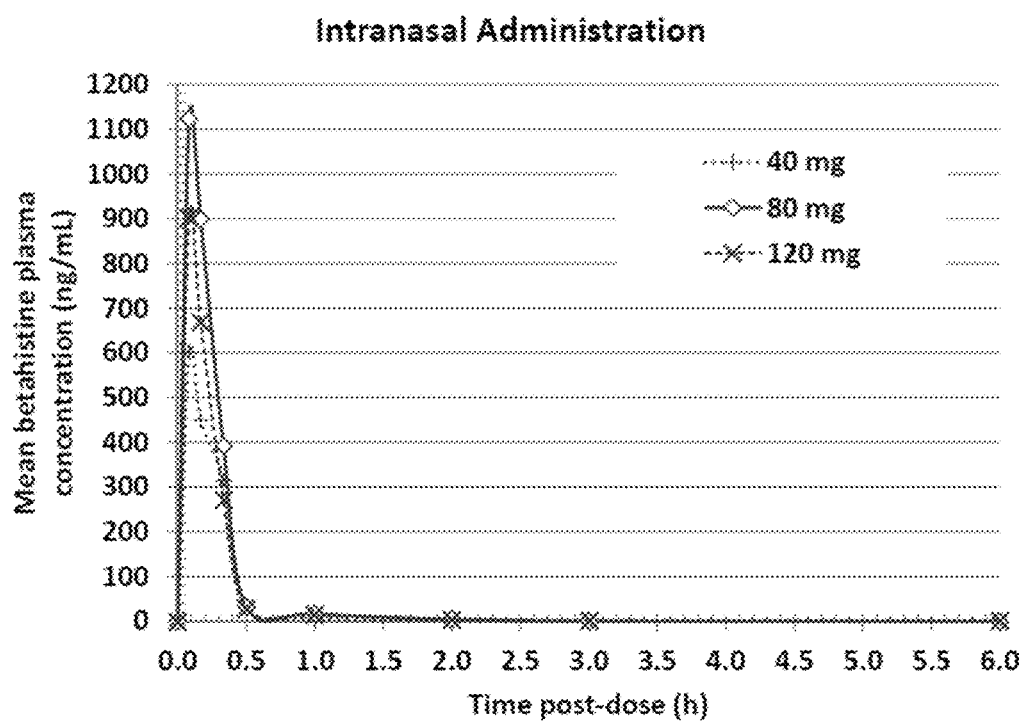
FIG. 6 shows the mean betahistine concentration in plasma over time from 8 beagle dogs following intranasal administration of a single dose of betahistine dihydrochloride at a dose of 40, 80, or 120 mg.

FIGS. 5 and 6 are graphs showing the median (FIG. 5) and mean (FIG. 6) betahistine plasma concentrations following intranasal administration of betahistine dihydrochloride at a total dose of 40, 80, and 120 mg over time, with values for male and female animals pooled. The graph based on the median values, FIG. 5, shows a dose-dependent increase in the betahistine plasma concentration. In the graph based on the mean values (FIG. 6), the mean Cmax for the 80 mg dose appears to be higher than the mean $C_{max}$ for the 120 mg dose. This discrepancy is due to certain outlier values.

Figure 7:
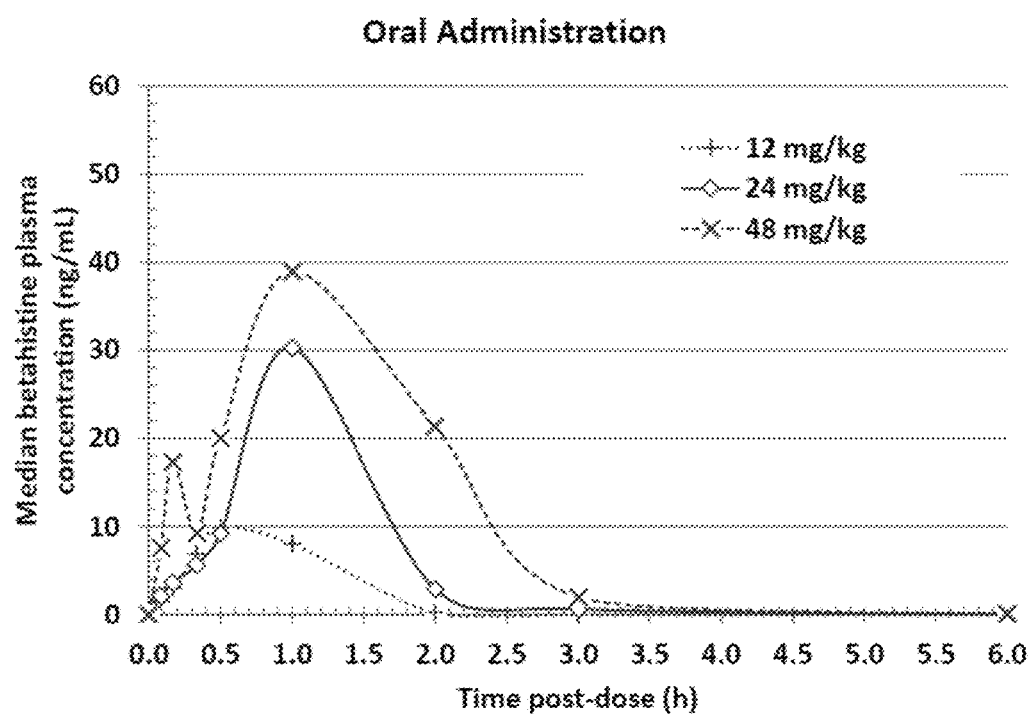
FIG. 7 shows the median betahistine concentration in plasma over time from 8 beagle dogs following oral administration of betahistine.
Figure 8:
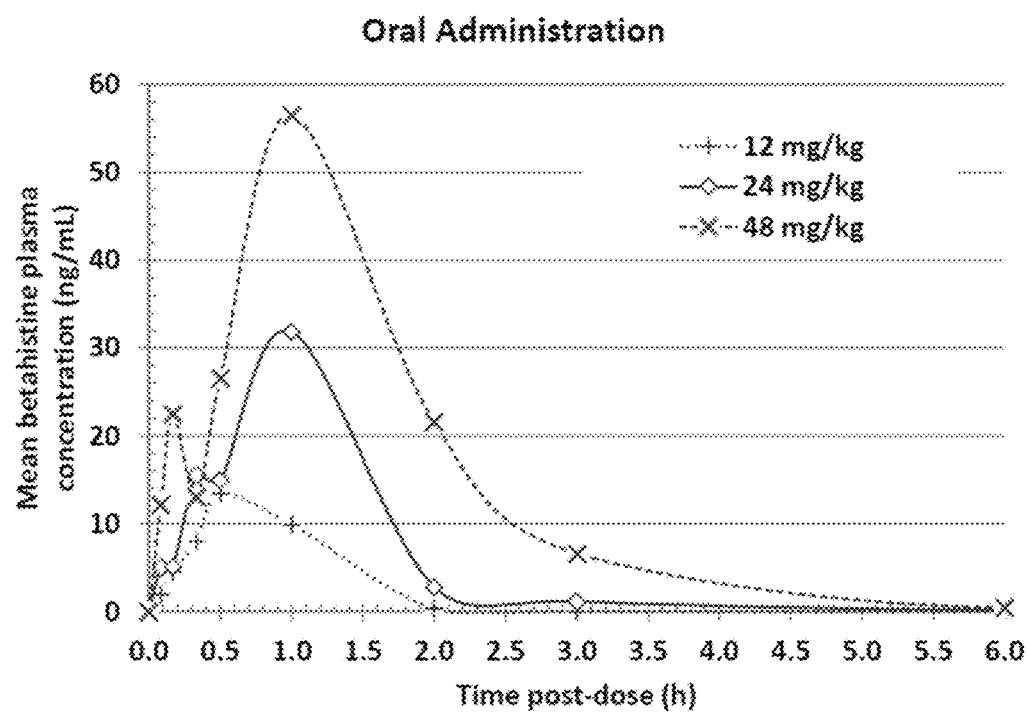
FIG. 8 shows the mean betahistine concentration in plasma over time from 8 beagle dogs following oral administration of betahistine.

FIGS. 7 and 8 are graphs showing the median (FIG. 7) and mean (FIG. 8) betahistine plasma concentrations, with values for male and female animals pooled, following oral administration of betahistine over time.

Figure 9:
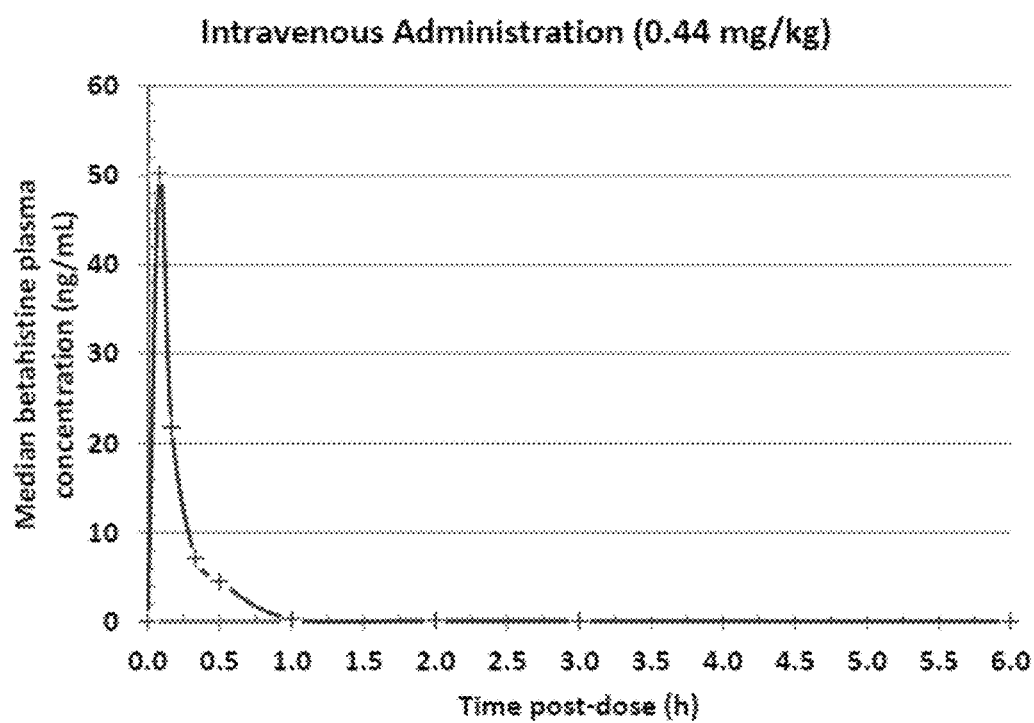
FIG. 9 shows the median betahistine concentration in plasma over time from 8 beagle dogs following intravenous administration of betahistine.
Figure 10:
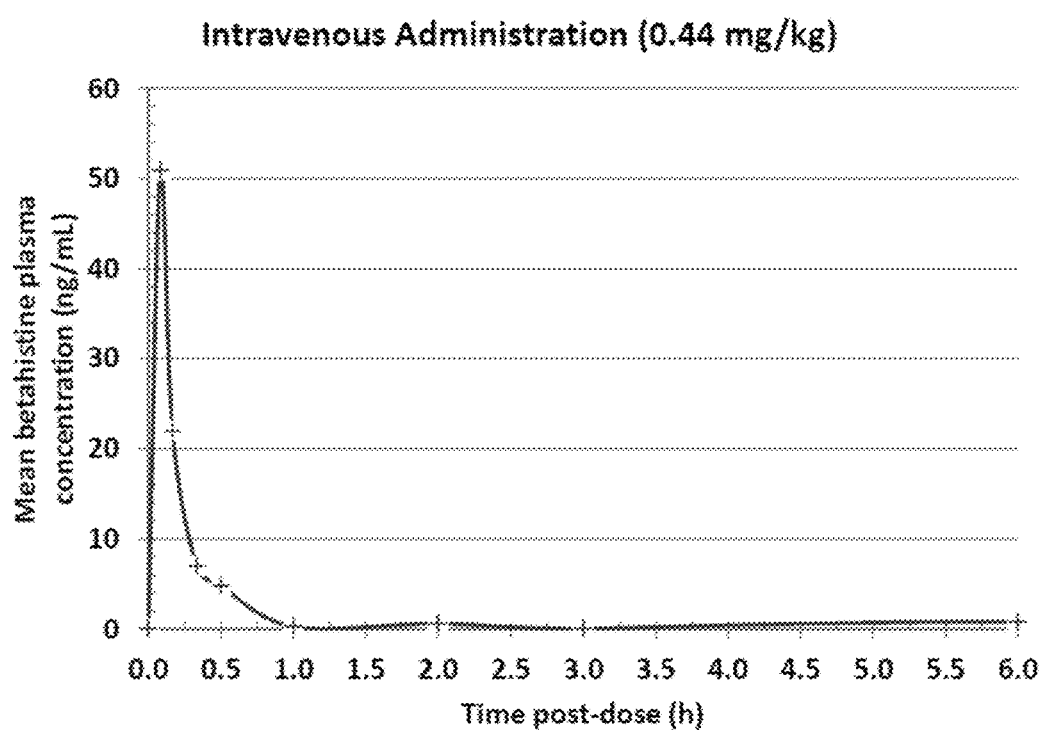
FIG. 10 shows the mean betahistine concentration in plasma over time from 8 beagle dogs following intravenous administration of betahistine.

FIGS. 9 and 10 are graphs showing the median (FIG. 9) and mean (FIG. 10) betahistine plasma concentrations, with values for male and female animals pooled, following intravenous administration of betahistine over time.

Tables 18-20 show a summary of pharmacokinetic parameters for betahistine (BH) following oral, intranasal, and intravenous administration. Tables 21-23 show a summary of pharmacokinetic parameters for 2-PAA following oral, intranasal, and intravenous administration of betahistine.

TABLE 18

Summary (Mean ± SD) BH Pharmacokinetics Parameters in Beagle Dog Plasma Following Oral Administration of BH on Day 1

| Day | Analyte | Route | Gender | Dose (mg/kg) | $T_{max}{}^a$ (hr) | $C_{max}$ (ng/mL) | $C_{max}$/D (ng/mL/ (mg/kg)) | $AUC_{(0-6)}$ (hr*ng/mL) | $AUC_{(0-t)}$ (hr*ng/mL) | $AUC_{(0-t)}$/D (hr*ng/mL/ (mg/kg)) | $AUC_{(0-inf)}$ (hr*ng/mL) | $T_{1/2}$ (hr) |
|---|---|---|---|---|---|---|---|---|---|---|---|---|
| 1 | BH | Oral | Male | 12 | 0.5 (0.5-0.5) | 18.9 ± 9.99 | 1.58 ± 0.833 | 13.0 ± 2.23 | 12.5 ± 2.02 | 1.04 ± 0.168 | 13.3 ± ID | 0.313 ± ID |
| | | | | 24 | 1 (0.33-1) | 38.3 ± 28.1 | 1.60 ± 1.17 | 34.5 ± 17.2 | 34.5 ± 17.1 | 1.44 ± 0.714 | 34.6 ± 17.1 | 0.785 ± 0.388 |
| | | | | 48 | 1 (1-1) | 102 ± 30.2 | 2.13 ± 0.628 | 131 ± 28.3 | 131 ± 28.3 | 2.73 ± 0.590 | 133 ± ID | 0.522 ± ID |
| | | | Female | 12 | 1 (0.5-1) | 14.7 ± 4.56 | 1.22 ± 0.380 | NC | 15.9 ± 5.80 | 1.33 ± 0.483 | NC | NC |
| | | | | 24 | 1 (0.33-1) | 38.0 ± 26.1 | 1.58 ± 1.09 | 26.2 ± ID | 41.0 ± 17.9 | 1.71 ± 0.748 | 27.7 ± ID | 1.41 ± ID |
| | | | | 48 | 1 (0.08-1) | 33.5 ± 9.11 | 0.697 ± 0.190 | 77.5 ± 25.4 | 77.5 ± 25.4 | 1.61 ± 0.528 | 69.2 ± 23.3 | 0.599 ± 0.0351 |
| | | | Sex-Combined | 12 | 0.5 (0.5-1) | 16.8 ± 7.54 | 1.40 ± 0.628 | 13.0 ± 2.23 | 14.2 ± 4.41 | 1.18 ± 0.368 | 13.3 ± ID | 0.313 ± ID |
| | | | | 24 | 1 (0.33-1) | 38.2 ± 25.1 | 1.59 ± 1.05 | 31.7 ± 14.0 | 37.8 ± 16.6 | 1.57 ± 0.692 | 32.3 ± 13.8 | 0.995 ± 0.458 |
| | | | | 48 | 1 (0.08-1) | 62.9 ± 41.2 | 1.31 ± 0.857 | 100 ± 37.6 | 100 ± 37.6 | 2.09 ± 0.783 | 94.6 ± 43.4 | 0.568 ± 0.0565 |

$^a$Median $T_{max}$ (Min-Max);
NC = Not Calculated;
ID = Insufficient Data.

TABLE 19

Summary (Mean ± SD) BH Pharmacokinetics Parameters in Beagle Dog Plasma Following Intranasal Administration of BH (AM-125) on Day 8

| Day | Analyte | Route | Gender | Nominal Dose (mg) | Dose (mg/kg) | $T_{max}^a$ (hr) | $C_{max}$ (ng/mL) | $C_{max}/D$ (ng/mL/(mg/kg)) | $AUC_{(0-6)}$ (hr*ng/mL) | $AUC_{(0-t)}$ (hr*ng/mL) | $AUC_{(0-t)}/D$ (hr*ng/mL/(mg/kg)) | $AUC_{(0-inf)}$ (hr*ng/mL) | $T_{1/2}$ (hr) |
|---|---|---|---|---|---|---|---|---|---|---|---|---|---|
| 8 | BH | Intranasal | Male | 40 | 5 | 0.17 (0.08-0.33) | 598 ± 451 | 120 ± 90.1 | 178 ± 122 | 182 ± 122 | 36.4 ± 24.4 | 131 ± ID | NM |
|   |   |   |   | 80 | 9.8 | 0.13 (0.08-0.17) | 735 ± 557 | 75.0 ± 56.9 | 168 ± 140 | 172 ± 140 | 17.5 ± 14.3 | 202 ± 156 | NM |
|   |   |   |   | 120 | 15.8 | 0.13 (0.08-0.17) | 765 ± 375 | 48.4 ± 23.7 | 194 ± 79.8 | 199 ± 78.5 | 12.6 ± 4.97 | NC | NC |
|   |   |   | Female | 40 | 6 | 0.08 (0.08-0.17) | 770 ± 253 | 128 ± 42.1 | 180 ± 57.3 | 181 ± 55.8 | 30.2 ± 9.31 | NC | NC |
|   |   |   |   | 80 | 13 | 0.14 (0.08-0.33) | 1790 ± 1320 | 138 ± 102 | 432 ± 281 | 440 ± 283 | 33.8 ± 21.8 | 480 ± 336 | NM |
|   |   |   |   | 120 | 17.7 | 0.08 (0.08-0.17) | 1330 ± 300 | 75.1 ± 17.0 | 277 ± 7.99 | 290 ± 8.47 | 16.4 ± 0.479 | 302 ± ID | NM |

$^a$Median $T_{max}$ (Min-Max);
NM = Not Meaningful;
NC = Not Calculated;
ID = Insufficient Data.

TABLE 20

Summary (Mean ± SD) BH Pharmacokinetics Parameters in Beagle Dog Plasma Following IV Bolus Injection of BH on Day 15

| Day | Analyte | Route | Gender | Dose (mg/kg) | $T_{max}^a$ (hr) | $C_{max}$ (ng/mL) | $C_{max}/D$ (ng/mL/(mg/kg)) | $AUC_{(0-6)}$ (hr*ng/mL) | $AUC_{(0-t)}$ (hr*ng/mL) | $AUC_{(0-t)}/D$ (hr*ng/mL/(mg/kg)) | $AUC_{(0-inf)}$ (hr*ng/mL) | $T_{1/2}$ (hr) | CL (mL/hr/kg) | Vd (mL/kg) |
|---|---|---|---|---|---|---|---|---|---|---|---|---|---|---|
| 15 | BH | IV Bolus | Male | 0.44 | 0.08 (0.08-0.08) | 58.2 ± 7.93 | 132 ± 18.0 | 19.5 ± 5.05 | 19.5 ± 5.06 | 44.3 ± 11.5 | 18.4 ± ID | 0.930 ± ID | 23900 ± ID | 32100 ± ID |
|   |   |   | Female | 0.44 | 0.09 (0.08-0.11) | 43.7 ± 8.84 | 99.3 ± 20.1 | 16.3 ± 6.54 | 26.5 ± 17.6 | 60.3 ± 40.0 | 14.3 ± ID | 0.238 ± ID | 30800 ± ID | 10600 ± ID |
|   |   |   | Sex-Combined | 0.44 | 0.08 (0.08-0.11) | 50.9 ± 11.0 | 116 ± 24.9 | 17.9 ± 5.67 | 23.0 ± 12.6 | 52.3 ± 28.5 | 16.3 ± ID | 0.584 ± ID | 27400 ± ID | 21300 ± ID |

$^a$Median $T_{max}$ (Min-Max);
ID = Insufficient Data.

TABLE 21

Summary (Mean ± SD) 2-PAA Pharmacokinetics Parameters in Beagle Dog Plasma Following Oral Administration of BH on Day 1

| Day | Analyte | Route | Gender | Dose (mg/kg) | $T_{max}^a$ (hr) | $C_{max}$ (ng/mL) | $C_{max}/D$ (ng/mL/(mg/kg)) | $AUC_{(0-6)}$ (hr*ng/mL) | $AUC_{(0-t)}$ (hr*ng/mL) | $AUC_{(0-t)}/D$ (hr*ng/mL/(mg/kg)) | $AUC_{(0-inf)}$ (hr*ng/mL) | $T_{1/2}$ (hr) |
|---|---|---|---|---|---|---|---|---|---|---|---|---|
| 1 | 2-PAA | Oral | Male | 12 | 1.5 (1-2) | 12700 ± 2420 | 1060 ± 202 | 37300 ± 10500 | 50500 ± 21100 | 4210 ± 1760 | 50500 ± 21100 | 2.21 ± 0.160 |
|   |   |   |   | 24 | 1.5 (1-2) | 26400 ± 7520 | 1100 ± 313 | 76400 ± 21100 | 107000 ± 28200 | 4460 ± 1180 | 107000 ± 28200 | 2.04 ± 0.107 |
|   |   |   |   | 48 | 2 (2-2) | 50900 ± 8840 | 1060 ± 184 | 178000 ± 24900 | 286000 ± 39200 | 5950 ± 817 | 286000 ± 39300 | 2.10 ± 0.181 |
|   |   |   | Female | 12 | 1 (1-2) | 14500 ± 1370 | 1210 ± 114 | 41300 ± 5020 | 57200 ± 11300 | 4760 ± 940 | 57200 ± 11300 | 2.12 ± 0.110 |
|   |   |   |   | 24 | 2 (1-2) | 21300 ± 3530 | 885 ± 147 | 69300 ± 7850 | 110000 ± 14300 | 4590 ± 594 | 110000 ± 14300 | 2.14 ± 0.176 |
|   |   |   |   | 48 | 2 (2-3) | 37500 ± 8560 | 781 ± 178 | 144000 ± 35400 | 237000 ± 63500 | 4930 ± 1320 | 208000 ± 35000 | 2.24 ± 0.170 |
|   |   |   | Sex-Combined | 12 | 1 (1-2) | 13600 ± 2060 | 1130 ± 172 | 39300 ± 7930 | 53800 ± 16000 | 4490 ± 1340 | 53900 ± 16100 | 2.17 ± 0.135 |
|   |   |   |   | 24 | 2 (1-2) | 23800 ± 6090 | 992 ± 254 | 72900 ± 15200 | 109000 ± 20800 | 4530 ± 866 | 109000 ± 20800 | 2.09 ± 0.145 |
|   |   |   |   | 48 | 2 (2-3) | 43200 ± 10700 | 901 ± 222 | 158000 ± 34200 | 258000 ± 56700 | 5370 ± 1180 | 247000 ± 53900 | 2.17 ± 0.176 |

$^a$Median $T_{max}$ (Min-Max);

TABLE 22

Summary (Mean ± SD) 2-PAA Pharmacokinetics Parameters in Beagle Dog Plasma Following Intranasal Administration of BH on Day 8

| Day | Analyte | Route | Gender | Nominal Dose (mg) | Dose (mg/kg) | $T_{max}{}^a$ (hr) | $C_{max}$ (ng/mL) | $C_{max}$/D (ng/mL/ (mg/kg)) | $AUC_{(0-6)}$ (hr*ng/mL) | $AUC_{(0-t)}$ (hr*ng/mL) | $AUC_{(0-t)}$/D (hr*ng/mL/ (mg/kg)) | $AUC_{(0-inf)}$ (hr*ng/mL) | $T_{1/2}$ (hr) |
|---|---|---|---|---|---|---|---|---|---|---|---|---|---|
| 8 | 2-PAA | Intranasal | Male | 40 | 5 | 0.5 (0.5-1) | 3480 ± 2270 | 695 ± 454 | 9440 ± 7580 | 12200 ± 10800 | 2440 ± 2160 | 12200 ± 10800 | 2.96 ± 0.536 |
| | | | | 80 | 9.8 | 1 (0.5-1) | 3320 ± 1070 | 339 ± 109 | 8450 ± 2870 | 10400 ± 3600 | 1060 ± 368 | 10400 ± 3610 | 2.86 ± 0.186 |
| | | | | 120 | 15.8 | 1 (0.33-1) | 3930 ± 987 | 249 ± 62.5 | 10200 ± 2640 | 12700 ± 3110 | 806 ± 197 | 12800 ± 3090 | 2.87 ± 0.434 |
| | | | Female | 40 | 6 | 0.75 (0.5-1) | 5570 ± 1290 | 928 ± 215 | 14800 ± 3710 | 19000 ± 4870 | 3170 ± 812 | 19000 ± 4860 | 2.66 ± 0.275 |
| | | | | 80 | 13 | 1 (1-1) | 7030 ± 3020 | 541 ± 232 | 19300 ± 7760 | 25200 ± 10900 | 1940 ± 838 | 25300 ± 10900 | 2.97 ± 0.348 |
| | | | | 120 | 17.7 | 1 (1-2) | 3810 ± 765 | 215 ± 43.2 | 10600 ± 3470 | 14000 ± 5440 | 790 ± 307 | 14100 ± 5470 | 3.46 ± 0.239 |

$^a$Median $T_{max}$ (Min-Max);

TABLE 23

Summary (Mean ± SD) 2-PAA Pharmacokinetics Parameters in Beagle Dog Plasma Following IV Bolus Injection of BH on Day 15

| Day | Analyte | Route | Gender | Dose (mg/kg) | $T_{max}{}^a$ (hr) | $C_{max}$ (ng/mL) | $C_{max}$/D (ng/mL/ (mg/kg)) | $AUC_{(0-6)}$ (hr*ng/mL) | $AUC_{(0-t)}$ (hr*ng/mL) | $AUC_{(0-t)}$/D (hr*ng/mL/ (mg/kg)) | $AUC_{(0-inf)}$ (hr*ng/mL) | $T_{1/2}$ (hr) |
|---|---|---|---|---|---|---|---|---|---|---|---|---|
| 15 | 2-PAA | IV Bolus | Male | 0.44 | 0.13 (0.08-0.33) | 736 ± 53.5 | 1670 ± 121 | 1450 ± 388 | 1740 ± 641 | 3960 ± 1460 | 1760 ± 642 | 2.59 ± 1.07 |
| | | | Female | 0.44 | 0.18 (0.11-0.2) | 722 ± 75.3 | 1640 ± 171 | 1540 ± 101 | 1830 ± 209 | 4160 ± 475 | 1860 ± 188 | 2.78 ± 1.01 |
| | | | Sex-Combined | 0.44 | 0.17 (0.08-0.33) | 729 ± 60.9 | 1660 ± 138 | 1500 ± 267 | 1790 ± 444 | 4060 ± 1010 | 1810 ± 441 | 2.69 ± 0.968 |

$^a$Median $T_{max}$ (Min-Max);

Tables 24 and 25 show the Absolute Bioavailability (% F) of betahistine (BH) in dogs following oral and intranasal administration.

TABLE 24

Absolute Bioavailability (% F) of BH in Beagle Dog Plasma Following Oral Administration of BH

| Route Comparison | Analyte | Gender | Dose (mg/kg) | % F $AUC_{(0-t)}$/D |
|---|---|---|---|---|
| Oral/IV Bolus | BH | Male | 12/0.44 | 2.35 |
| | | | 24/0.44 | 3.24 |
| | | | 48/0.44 | 6.17 |
| | | Female | 12/0.44 | 2.20 |
| | | | 24/0.44 | 2.84 |
| | | | 48/0.44 | 2.68 |
| | | Sex-Combined | 12/0.44 | 2.26 |
| | | | 24/0.44 | 3.01 |
| | | | 48/0.44 | 4.01 |

TABLE 25

Absolute Bioavailability (%) of BH in Beagle Dog Plasma Following Intranasal Administration of BH

| Route Comparison | Analyte | Gender | Dose (mg/kg) | % F $AUC_{(0-t)}$/D |
|---|---|---|---|---|
| Intranasal/IV Bolus | BH | Male | 5/0.44 | 82.1 |
| | | | 9.8/0.44 | 39.5 |
| | | | 15.8/0.44 | 28.4 |
| | | Female | 6/0.44 | 50.2 |
| | | | 13/0.44 | 56.1 |
| | | | 17.7/0.44 | 27.1 |

Table 26 shows the Relative Bioavailability (Frel) of betahistine (BH) administered intranasally relative to the oral administration.

TABLE 26

Bioavailability of betahistine in dogs for intranasal administration relative to oral administration

| | | Intranasal | | Oral | | |
|---|---|---|---|---|---|---|
| Dose (mg) | Dose (mg/kg) | AUC/dose (h · ng/mL)/ (mg/kg) | mg/kg | AUC/dose (h · ng/mL)/ (mg/kg) | Rel. Bioavail. |
| Dogs, male | | | | | | |
| 40 | 5 | 36.4 | 12 | 1.04 | 35.0 |
| 80 | 9.8 | 17.5 | 24 | 1.44 | 12.2 |
| 120 | 15.8 | 12.6 | 48 | 2.73 | 4.6 |

TABLE 26-continued

Bioavailability of betahistine in dogs for intranasal administration relative to oral administration

| Dose (mg) | Intranasal | | | Oral | | Rel. Bioavail. |
|---|---|---|---|---|---|---|
| | Dose (mg/kg) | AUC/dose (h·ng/mL)/ (mg/kg) | mg/kg | AUC/dose (h·ng/mL)/ (mg/kg) | | |
| Dogs, female | | | | | | |
| 40 | 6 | 30.2 | 12 | 1.33 | | 22.7 |
| 80 | 13 | 33.8 | 24 | 1.71 | | 19.8 |
| 120 | 17.7 | 16.4 | 48 | 1.61 | | 10.2 |

Example 6: Relative Bioavailability of Betahistine Via Intranasal Administration Relative to Oral Administration in Humans For the calculation of the relative bioavailability of intranasal betahistine compared to peroral betahistine, the area under the concentration-time curve (AUC) determined in Example 3 was compared to the AUC determined in a study with oral betahistine in healthy volunteers described in Barak et al. (*Journal of Psychopharmacology*, 2016, Vol. 30(3) 237-241). In brief, in this study, forty-eight healthy women were recruited and randomized to receive per os (i.e. orally) either betahistine 144 mg/day (48 mg t.i.d.) or matching placebo for 4 weeks. Their mean weight was 60.2 kg in the active-treated group (n=24) and 59.8 kg in the placebo group (n=24). Study medication (betahistine or matching placebo) was administered at least 30 minutes prior to eating. On Day 8, blood samples of 6 mL each were collected at 8 am, and 30, 60, 150 and 300 minutes theraftor. Plasma concentrations of betahistine and its metabolite 2-PAA were determined by high-performance liquidy chromatography. The AUC$_{(0-5\ h)}$ was 121 pg·h/mL at a dose of approximately 0.8 mg/kg.

For an intranasal dose of 40 mg (or 0.57 mg/kg) in Example 3, an AUC of 3531 pg·h/mL resulted (see Table 3).

Based on the AUC values for oral administration in the Barak et al. study and the AUC values for intranasal administration from Example 3, a relative bioavailability of oral vs. intransal (i.e. bioavailability via oral relative to intranasal) administration comes out to be approximately 2.4% whereas the relative bioavailability of intranasal vs oral (bioavailability via intranasal relative to oral) is summarized in the following table.

TABLE 27

Bioavailability of betahistine via intranasal administration relative to oral administration

| Dose (mg) | Weight (kg) | Dose (mg/kg) | AUC (h*ng/mL) | AUC/ Dose (h·ng/mL)/ (mg/kg) | Rel. Bioavail. |
|---|---|---|---|---|---|
| Barak et al. data (oral) | | | | | |
| 48 | 60.2 | 0.8 | 0.121 | 0.15 | |
| Example 3 data (intranasal) | | | | | |
| 5 | 71.9 | 0.07 | 0.209 | 3.01 | 19.9 |
| 10 | 68.8 | 0.15 | 0.533 | 3.67 | 24.2 |
| 20 | 69.6 | 0.29 | 1.608 | 5.60 | 37.0 |
| 40 | 70.4 | 0.57 | 3.531 | 6.21 | 41.1 |

Table 27 shows that the bioavailability with intranasal administration is 20-40 times higher than with oral administration. When using relative bioavailability at comparable absolute doses—40 mg intranasal vs. 48 mg per os—the fold factor is 41.1×. The 0.8 mg/kg in the Barak et al. study represent the currently approved 48 mg daily dose in one single administration; although patients there received 3×48 mg daily, each dose is considered separate due to the rapid elimination.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A pharmaceutical composition for intranasal delivery to a human patient, comprising a solution or suspension of a therapeutically effective amount of betahistine dihydrochloride, a viscosity enhancing agent, a moisturizing agent, and a buffer, wherein the pH of the pharmaceutical composition is about 4.4 to about 6.4.

2. The pharmaceutical composition of claim 1, wherein the viscosity enhancing agent is selected from the group consisting of polyvinyl pyrrolidone, polyvinyl alcohol, methylcellulose, carboxymethyl cellulose-Na, hydroxyethylcellulose, hydroxypropyl cellulose, hydroxypropyl methylcellulose, polyethylene-oxide, Carbopol, polyethylene glycol, propylene glycol, glycerin, alginates, carrageenan, pectins, maltodextrin, sodium starch glycolate tragacanth gum, gum arabic, microcrystalline cellulose and combinations thereof.

3. The pharmaceutical composition of claim 2, wherein the viscosity enhancing agent is polyvinyl pyrrolidone.

4. The pharmaceutical composition of claim 1, wherein the moisturizing agent is selected from the group consisting of glycerin, ethylene glycol, propylene glycol, propylene glycol 400, hexalene glycol, butylene glycol, dextrose, glyceryl triacetate, polydextrose, glycerol, glyceryl triacetate, sorbitol, mannitol, and combinations thereof.

5. The pharmaceutical composition of claim 4, wherein the moisturizing agent is selected from the group consisting of glycerin, polyethylene glycol 400 and propylene glycol.

6. The pharmaceutical composition of claim 1, wherein the composition comprises betahistine dihydrochloride at a concentration of about 1 mg/mL to about 1000 mg/mL.

7. The pharmaceutical composition of claim 6, wherein the composition comprises betahistine dihydrochloride at a concentration of about 10 mg/mL to about 400 mg/mL.

8. The pharmaceutical composition of claim 1, wherein the composition is in the form of a unit dose comprising the betahistine in an amount of about 5 mg to about 100 mg.

9. The pharmaceutical composition of claim 1, wherein the composition is in the form of a unit dose comprising the betahistine in an amount of about 5 mg, about 10 mg, about 20 mg, about 40 mg, or about 80 mg.

10. The pharmaceutical composition of claim 1, wherein the composition is in the form of a unit dose, comprising about 1 μL to about 1000 μL of the composition per unit dose.

11. The pharmaceutical composition of claim 1, wherein the composition is capable of being administered as a spray or aerosol.

12. The pharmaceutical composition of claim 1, wherein the composition is an aqueous solution.

13. The pharmaceutical composition of claim 1, wherein a single dose of the composition comprises 20 mg or 40 mg of betahistine.

14. The pharmaceutical composition of claim 1, further comprising at least one enzyme inhibitor or absorption promoter.

15. The pharmaceutical composition of claim 1, comprising a preservative.

16. The pharmaceutical composition of claim 15, wherein the preservative is selected from the group consisting of benzethonium chloride, benzoxonium chloride, benzododecinium bromide, alkyltrimethilammonium bromide, cetrimonium bromide, benzalkonium chloride, phenylethyl alcohol, benzoic acid and esters and salts thereof, parabens, potassium sorbate, sorbic acid, calcium sorbate, sodium sorbate, chlorhexidine, boric acids and phenols.

17. A method of treating an inner ear disorder, a vestibular disorder, ADHD, dementia, obesity or weight gain, comprising intranasally administering the pharmaceutical composition of claim 1 to a subject in need thereof.

18. The method of claim 17, wherein the method is for treating a vestibular disorder.

19. The method of claim 18, wherein the vestibular disorder is vestibular vertigo or Meniere's disease.

20. The method of claim 17, wherein the method is for treating an inner ear disorder selected from tinnitus or hearing loss.

* * * * *